(12) United States Patent
Mumby et al.

(10) Patent No.: US 10,130,519 B2
(45) Date of Patent: *Nov. 20, 2018

(54) WOUND DRESSING AND METHOD OF TREATMENT

(71) Applicant: Smith & Nephew PLC, London (GB)

(72) Inventors: Ella Lynn Mumby, Hull (GB); Helene Anne Lecomte, York (GB)

(73) Assignee: Smith & Nephew PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/219,886

(22) Filed: Jul. 26, 2016

(65) Prior Publication Data

US 2016/0331594 A1  Nov. 17, 2016

Related U.S. Application Data

(63) Continuation of application No. 14/232,607, filed as application No. PCT/GB2012/000587 on Jul. 12, 2012.

(30) Foreign Application Priority Data

Jul. 14, 2011 (GB) .................................. 1112084.7
Jun. 22, 2012 (GB) .................................. 1211171.2

(51) Int. Cl.
*A61M 27/00* (2006.01)
*A61M 1/00* (2006.01)
(Continued)

(52) U.S. Cl.
CPC .. *A61F 13/00055* (2013.01); *A61F 13/00029* (2013.01); *A61F 13/00059* (2013.01); *A61F 13/00063* (2013.01); *A61F 13/00068* (2013.01); *A61F 13/00987* (2013.01); *A61F 13/022* (2013.01); *A61F 13/0203* (2013.01); *A61F 13/0206* (2013.01); *A61F 13/0223* (2013.01);
(Continued)

(58) Field of Classification Search
CPC ............ A61F 13/0206; A61F 13/00055; A61F 13/00059; A61F 13/00063; A61F 13/0203; A61F 13/0226; A61F 2013/0028; A61F 2013/000846; A61F 2013/00876
USPC ................................ 604/319, 543, 304, 313
See application file for complete search history.

(56) References Cited

U.S. PATENT DOCUMENTS 2,905,174 A  9/1959  Smith
3,687,136 A  8/1972  Carmody
(Continued)

FOREIGN PATENT DOCUMENTS

CN  101002707 A  7/2007
EP  0 053 936  6/1982
(Continued)

OTHER PUBLICATIONS

U.S. Appl. No. 15/220,204, filed Jul. 26, 2016, Mumby et al.
(Continued)

*Primary Examiner* — Jacqueline Stephens
(74) *Attorney, Agent, or Firm* — Knobbe, Martens, Olson & Bear, LLP

(57) ABSTRACT

A wound dressing, a method of manufacturing a wound dressing, and a method of treating a patient are disclosed. The wound dressing may include an absorbent layer for absorbing wound exudate; and an obscuring element for at least partially obscuring a view of wound exudate absorbed by the absorbent layer in use.

23 Claims, 27 Drawing Sheets

(51) Int. Cl.
*A61F 13/00* (2006.01)
*A61F 13/02* (2006.01)

(52) U.S. Cl.
CPC ...... *A61F 13/0226* (2013.01); *A61F 13/0253* (2013.01); *A61M 1/0088* (2013.01); *A61F 2013/0028* (2013.01); *A61F 2013/00846* (2013.01); *A61F 2013/00876* (2013.01)

(56) References Cited

U.S. PATENT DOCUMENTS

| | | |
|---|---|---|
| 4,798,603 A | 1/1989 | Meyer et al. |
| 4,834,735 A | 5/1989 | Alemany et al. |
| 4,846,164 A | 7/1989 | Martz |
| 4,968,181 A | 11/1990 | Goldman |
| 4,973,325 A | 11/1990 | Sherrod et al. |
| 4,988,344 A | 1/1991 | Reising et al. |
| 4,988,345 A | 1/1991 | Reising |
| 5,018,515 A | 5/1991 | Gilman |
| 5,021,050 A | 6/1991 | Iskra |
| 5,037,409 A | 8/1991 | Chen et al. |
| 5,065,600 A | 11/1991 | Byles |
| 5,115,801 A | 5/1992 | Cartmell et al. |
| 5,124,197 A | 6/1992 | Bernardin et al. |
| 5,149,334 A | 9/1992 | Lahrman et al. |
| 5,151,091 A | 9/1992 | Glaug et al. |
| 5,160,328 A | 11/1992 | Cartmell et al. |
| 5,171,391 A | 12/1992 | Chmielewski et al. |
| 5,175,046 A | 12/1992 | Nguyen |
| 5,197,945 A | 3/1993 | Cole et al. |
| 5,217,445 A | 6/1993 | Young et al. |
| 5,236,427 A | 8/1993 | Hamajima et al. |
| 5,242,435 A | 9/1993 | Murji et al. |
| 5,257,982 A | 11/1993 | Cohen et al. |
| 5,271,987 A | 12/1993 | Iskra |
| 5,281,208 A | 1/1994 | Thompson et al. |
| 5,294,478 A | 3/1994 | Wanek et al. |
| 5,296,290 A | 3/1994 | Brassington |
| 5,314,743 A | 5/1994 | Meirowitz et al. |
| 5,318,554 A | 6/1994 | Young et al. |
| 5,330,456 A | 7/1994 | Robinson |
| 5,336,219 A | 8/1994 | Krantz |
| 5,342,336 A | 8/1994 | Meirowitz et al. |
| 5,348,547 A | 9/1994 | Payne et al. |
| 5,354,261 A | 10/1994 | Clark et al. |
| 5,356,405 A | 10/1994 | Thompson et al. |
| 5,360,420 A | 11/1994 | Cook et al. |
| 5,364,381 A | 11/1994 | Soga et al. |
| 5,364,382 A | 11/1994 | Latimer et al. |
| 5,366,451 A | 11/1994 | Levesque |
| 5,368,909 A | 11/1994 | Langdon et al. |
| 5,368,926 A | 11/1994 | Thompson et al. |
| 5,374,260 A | 12/1994 | Lemay et al. |
| 5,380,294 A | 1/1995 | Persson |
| 5,382,245 A | 1/1995 | Thompson et al. |
| 5,387,208 A | 2/1995 | Ashton et al. |
| 5,397,316 A | 3/1995 | LaVon et al. |
| 5,401,267 A | 3/1995 | Couture-Dorschner et al. |
| 5,425,725 A | 6/1995 | Tanzer et al. |
| 5,431,643 A | 7/1995 | Ouellette et al. |
| 5,447,492 A | 9/1995 | Cartmell et al. |
| 5,454,800 A | 10/1995 | Hirt et al. |
| 5,456,660 A | 10/1995 | Reich et al. |
| 5,465,735 A | 11/1995 | Patel |
| 5,470,326 A | 11/1995 | Dabi et al. |
| H1511 H | 12/1995 | Chappell et al. |
| 5,480,377 A | 1/1996 | Cartmell et al. |
| 5,486,167 A | 1/1996 | Dragoo et al. |
| 5,487,736 A | 1/1996 | Van Phan |
| 5,497,788 A | 3/1996 | Inman et al. |
| 5,500,270 A | 3/1996 | Langdon et al. |
| 5,505,719 A | 4/1996 | Cohen et al. |
| 5,509,914 A | 4/1996 | Osborn, III |
| 5,514,120 A | 5/1996 | Johnston et al. |
| 5,525,407 A | 6/1996 | Yang |
| 5,536,264 A | 7/1996 | Hsueh et al. |
| H1585 H | 8/1996 | Ahr |
| 5,545,155 A | 8/1996 | Hseih et al. |
| 5,549,589 A | 8/1996 | Horney et al. |
| 5,562,107 A | 10/1996 | Lavender et al. |
| 5,562,646 A | 10/1996 | Goldman et al. |
| 5,562,650 A | 10/1996 | Everett et al. |
| 5,579,765 A | 12/1996 | Cox et al. |
| 5,591,148 A | 1/1997 | McFall et al. |
| 5,591,149 A | 1/1997 | Cree et al. |
| 5,593,395 A | 1/1997 | Martz |
| 5,603,707 A | 2/1997 | Trombetta et al. |
| 5,603,946 A | 2/1997 | Constantine |
| 5,609,588 A | 3/1997 | DiPalma et al. |
| 5,613,960 A | 3/1997 | Mizutani |
| 5,614,283 A | 3/1997 | Pontis et al. |
| 5,614,295 A | 3/1997 | Quincy, III et al. |
| 5,628,736 A | 5/1997 | Thompson |
| 5,632,731 A | 5/1997 | Patel |
| H1657 H | 6/1997 | Hammons et al. |
| 5,634,915 A | 6/1997 | Osterdahl |
| 5,637,080 A | 6/1997 | Geng |
| 5,643,238 A | 7/1997 | Baker |
| 5,648,142 A | 7/1997 | Phillips |
| 5,649,915 A | 7/1997 | Chauvette et al. |
| 5,649,916 A | 7/1997 | DiPalma et al. |
| 5,662,599 A | 9/1997 | Reich et al. |
| 5,665,082 A | 9/1997 | Boulanger |
| 5,669,895 A | 9/1997 | Murakami et al. |
| 5,675,079 A | 10/1997 | Gilman et al. |
| 5,700,254 A | 12/1997 | McDowall et al. |
| 5,702,356 A | 12/1997 | Hathman |
| 5,704,905 A | 1/1998 | Jensen et al. |
| 5,713,384 A | 2/1998 | Roach et al. |
| 5,713,842 A | 2/1998 | Kay |
| 5,716,703 A | 2/1998 | Payne |
| 5,728,084 A | 3/1998 | Palumbo et al. |
| 5,728,085 A | 3/1998 | Widlund et al. |
| 5,733,273 A | 3/1998 | Ahr |
| 5,752,945 A | 5/1998 | Mosley et al. |
| 5,762,641 A | 6/1998 | Bewick-Sonntag et al. |
| 5,788,684 A | 8/1998 | Abuto et al. |
| 5,801,107 A | 9/1998 | Everhart et al. |
| 5,810,798 A | 9/1998 | Finch et al. |
| 5,817,081 A | 10/1998 | LaVon et al. |
| 5,827,213 A | 10/1998 | Jensen |
| 5,827,254 A | 10/1998 | Trombetta et al. |
| 5,830,202 A | 11/1998 | Bogdanski et al. |
| 5,837,627 A | 11/1998 | Halabisky et al. |
| 5,840,052 A | 11/1998 | Johns |
| 5,843,064 A | 12/1998 | Koczab |
| 5,855,572 A | 1/1999 | Schmidt |
| 5,865,822 A | 2/1999 | Hamajima et al. |
| 5,865,824 A | 2/1999 | Chen et al. |
| 5,873,867 A | 2/1999 | Coles et al. |
| 5,877,097 A | 3/1999 | West et al. |
| 5,895,379 A | 4/1999 | Litchholt et al. |
| 5,897,541 A | 4/1999 | Uitenbrock et al. |
| 5,981,120 A | 4/1999 | Chmielewski |
| 5,916,507 A | 6/1999 | Dabi et al. |
| 5,925,026 A | 7/1999 | Arteman et al. |
| 5,931,823 A | 8/1999 | Stokes et al. |
| 5,938,995 A | 8/1999 | Koltisko, Jr. et al. |
| 5,941,863 A | 8/1999 | Guidotti et al. |
| 5,947,945 A | 9/1999 | Cree et al. |
| 5,951,535 A | 9/1999 | Fujiwara et al. |
| 5,961,506 A | 10/1999 | Guidotti et al. |
| 5,968,027 A | 10/1999 | Cole et al. |
| 5,989,478 A | 11/1999 | Ouellette et al. |
| 6,022,610 A | 2/2000 | Phan et al. |
| 6,037,518 A | 3/2000 | Guidotti et al. |
| 6,040,493 A | 3/2000 | Cooke et al. |
| 6,060,638 A | 5/2000 | Paul et al. |
| 6,068,620 A | 5/2000 | Chmielewski |
| 6,075,177 A | 6/2000 | Bahia et al. |
| 6,077,526 A | 6/2000 | Scully et al. |
| 6,096,015 A | 8/2000 | Yeo et al. |
| 6,103,953 A | 8/2000 | Cree et al. |
| 6,103,954 A | 8/2000 | Grondin et al. |

(56) References Cited

U.S. PATENT DOCUMENTS

| | | |
|---|---|---|
| 6,107,539 A | 8/2000 | Palumbo et al. |
| 6,117,523 A | 9/2000 | Sugahara |
| 6,124,520 A | 9/2000 | Roberts |
| 6,124,521 A | 9/2000 | Roberts |
| 6,127,595 A | 10/2000 | Makoui et al. |
| 6,168,849 B1 | 1/2001 | Braverman et al. |
| 6,191,340 B1 | 2/2001 | Carlucci et al. |
| 6,206,865 B1 | 3/2001 | Chen et al. |
| 6,235,966 B1 | 5/2001 | Magnusson et al. |
| 6,264,776 B1 | 7/2001 | DiPalma |
| 6,294,710 B1 | 9/2001 | Schmidt et al. |
| 6,344,036 B1 | 2/2002 | Ivansson |
| 6,362,390 B1 | 3/2002 | Carlucci et al. |
| 6,369,292 B1 | 4/2002 | Strack et al. |
| 6,372,952 B1 | 4/2002 | Lash et al. |
| 6,403,857 B1 | 6/2002 | Gross et al. |
| 6,461,339 B1 | 10/2002 | Sugahara |
| 6,468,295 B2 | 10/2002 | Augustine et al. |
| 6,497,689 B1 | 12/2002 | Schmidt et al. |
| 6,506,960 B1 | 1/2003 | Young et al. |
| 6,521,813 B1 | 2/2003 | Chihani |
| 6,528,696 B1 | 3/2003 | Ireland |
| 6,534,149 B1 | 3/2003 | Daley et al. |
| 6,545,194 B1 | 4/2003 | Schmidt et al. |
| 6,551,295 B1 | 4/2003 | Schmidt et al. |
| 6,552,244 B1 | 4/2003 | Jacques et al. |
| 6,570,057 B1 | 5/2003 | Schmidt et al. |
| 6,570,058 B1 | 5/2003 | Fuchs et al. |
| 6,573,424 B1 | 6/2003 | Raidel et al. |
| 6,586,653 B2 | 7/2003 | Graeme, III et al. |
| 6,610,898 B1 | 8/2003 | Magnusson et al. |
| 6,610,903 B1 | 8/2003 | Latimer et al. |
| 6,613,028 B1 | 9/2003 | Daley et al. |
| 6,613,955 B1 | 9/2003 | Lindsay et al. |
| 6,630,611 B1 | 10/2003 | Malowaniec |
| 6,664,439 B1 | 12/2003 | Arndt et al. |
| 6,683,229 B1 | 1/2004 | Ehrnsperger et al. |
| 6,685,681 B2 | 2/2004 | Lockwood et al. |
| 6,706,940 B2 | 3/2004 | Worthley |
| 6,719,742 B1 | 4/2004 | McCormack et al. |
| 6,727,403 B1 | 4/2004 | Ehrnsperger et al. |
| 6,762,337 B2 | 7/2004 | Boukanov et al. |
| 6,776,769 B2 | 8/2004 | Smith |
| 6,783,837 B1 | 8/2004 | Creagan et al. |
| 6,787,682 B2 | 9/2004 | Gilman |
| 6,835,192 B1 | 12/2004 | Guidotti et al. |
| 6,838,589 B2 | 1/2005 | Liedtke et al. |
| 6,841,715 B2 | 1/2005 | Roberts |
| 6,960,181 B2 | 11/2005 | Stevens |
| 6,998,511 B2 | 2/2006 | Worthley |
| 7,049,478 B1 | 5/2006 | Smith et al. |
| 7,112,712 B1 | 9/2006 | Ancell |
| 7,118,545 B2 | 10/2006 | Boyde |
| 7,122,023 B1 | 10/2006 | Hinoki |
| 7,122,712 B2 | 10/2006 | Lutri et al. |
| 7,294,751 B2 | 11/2007 | Propp et al. |
| 7,294,752 B1 | 11/2007 | Propp |
| 7,429,689 B2 | 9/2008 | Chen et al. |
| 7,476,205 B2 | 1/2009 | Erdmann |
| 7,511,187 B2 | 3/2009 | Kelly |
| 7,563,940 B2 | 7/2009 | Kurata |
| 7,569,742 B2 | 8/2009 | Haggstrom et al. |
| 7,576,256 B2 | 8/2009 | Björnberg et al. |
| 7,605,298 B2 | 10/2009 | Bechert et al. |
| 7,622,629 B2 | 11/2009 | Aail |
| 7,676,257 B2 | 3/2010 | Suryanarayanan et al. |
| 7,723,561 B2 | 5/2010 | Propp |
| 7,749,531 B2 | 7/2010 | Booher |
| 7,775,998 B2 | 8/2010 | Riesinger |
| 7,838,719 B2 | 11/2010 | Hilton, Jr. |
| 7,838,723 B1 | 11/2010 | Schmidt et al. |
| 7,922,703 B2 | 4/2011 | Riesinger |
| 7,935,066 B2 | 5/2011 | Shives et al. |
| 7,988,673 B2 | 8/2011 | Wright et al. |
| 8,021,347 B2 | 9/2011 | Vitaris et al. |
| 8,092,436 B2 | 1/2012 | Christensen |
| 8,147,468 B2 | 4/2012 | Barta et al. |
| 8,152,785 B2 | 4/2012 | Vitaris |
| 8,162,907 B2 | 4/2012 | Heagle |
| 8,168,848 B2 | 5/2012 | Lockwood et al. |
| 8,188,331 B2 | 5/2012 | Barta et al. |
| 8,212,101 B2 | 7/2012 | Propp |
| 8,241,261 B2 | 8/2012 | Randolph et al. |
| 8,252,971 B2 | 8/2012 | Aali et al. |
| 8,314,283 B2 | 11/2012 | Kingsford et al. |
| 8,328,858 B2 | 12/2012 | Barsky et al. |
| 8,376,972 B2 | 2/2013 | Fleischmann |
| 8,382,731 B2 | 2/2013 | Johannison |
| 8,403,899 B2 | 3/2013 | Sherman |
| 8,404,921 B2 | 3/2013 | Lee et al. |
| 8,425,478 B2 | 4/2013 | Olson |
| 8,535,296 B2 | 9/2013 | Blott et al. |
| 8,680,360 B2 | 3/2014 | Greener et al. |
| 8,791,316 B2 | 7/2014 | Greener |
| 8,795,247 B2 | 8/2014 | Bennett et al. |
| 8,801,685 B2 | 8/2014 | Armstrong et al. |
| 8,808,274 B2 | 8/2014 | Hartwell |
| 8,814,842 B2 | 8/2014 | Coulthard et al. |
| 8,829,263 B2 | 9/2014 | Haggstrom et al. |
| 8,916,742 B2 | 12/2014 | Smith |
| 9,012,714 B2 | 4/2015 | Fleischmann |
| 9,061,095 B2 | 6/2015 | Adie et al. |
| 9,220,822 B2 | 12/2015 | Hartwell et al. |
| 9,254,353 B2 | 2/2016 | Locke et al. |
| 2001/0000795 A1 | 5/2001 | Bolian, II et al. |
| 2001/0016985 A1 | 8/2001 | Insley et al. |
| 2001/0018308 A1 | 8/2001 | Quick et al. |
| 2001/0027302 A1 | 10/2001 | Glaug et al. |
| 2001/0027305 A1 | 10/2001 | Raidel et al. |
| 2001/0044610 A1 | 11/2001 | Kim et al. |
| 2001/0051178 A1 | 12/2001 | Blatchford et al. |
| 2001/0053904 A1 | 12/2001 | Abuto |
| 2002/0007167 A1 | 1/2002 | Dan et al. |
| 2002/0007169 A1 | 1/2002 | Graef et al. |
| 2002/0019602 A1 | 2/2002 | Geng |
| 2002/0019614 A1 | 2/2002 | Woon et al. |
| 2002/0026166 A1 | 2/2002 | Graef et al. |
| 2002/0034914 A1 | 3/2002 | De Leon et al. |
| 2002/0035354 A1 | 3/2002 | Mirle et al. |
| 2002/0062113 A1 | 5/2002 | Thomas et al. |
| 2002/0064639 A1 | 5/2002 | Rearick et al. |
| 2002/0087136 A1 | 7/2002 | Widlund |
| 2002/0090511 A1 | 7/2002 | Smith et al. |
| 2002/0110672 A1 | 8/2002 | Muratore-Pallatino et al. |
| 2002/0123728 A1 | 9/2002 | Graef et al. |
| 2002/0133132 A1 | 9/2002 | Copat et al. |
| 2002/0150678 A1 | 10/2002 | Cramer et al. |
| 2002/0165509 A1 | 11/2002 | Baer et al. |
| 2002/0169405 A1 | 11/2002 | Roberts |
| 2002/0176964 A1 | 11/2002 | Koslow |
| 2002/0177831 A1 | 11/2002 | Daley et al. |
| 2002/0180092 A1 | 12/2002 | Abba et al. |
| 2002/0183704 A1 | 12/2002 | Fields et al. |
| 2003/0009122 A1 | 1/2003 | Veras |
| 2003/0045707 A1 | 3/2003 | West et al. |
| 2003/0045825 A1 | 3/2003 | Etheredge, III |
| 2003/0050617 A1 | 3/2003 | Chen et al. |
| 2003/0069563 A1 | 4/2003 | Johnson |
| 2003/0070780 A1 | 4/2003 | Chen et al. |
| 2003/0073967 A1 | 4/2003 | Wahlstrom et al. |
| 2003/0088229 A1 | 5/2003 | Baker et al. |
| 2003/0088231 A1 | 5/2003 | Yoshimasa et al. |
| 2003/0093044 A1 | 5/2003 | Wahlstrom et al. |
| 2003/0097101 A1 | 5/2003 | Schmidt et al. |
| 2003/0097105 A1 | 5/2003 | Chen et al. |
| 2003/0097113 A1 | 5/2003 | Molee |
| 2003/0105442 A1 | 6/2003 | Johnston et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0124311 A1 | 7/2003 | Cree et al. |
| 2003/0134559 A1 | 7/2003 | Delzer et al. |

(56) References Cited

U.S. PATENT DOCUMENTS

| | | |
|---|---|---|
| 2003/0135174 A1 | 7/2003 | Benecke et al. |
| 2003/0135177 A1 | 7/2003 | Baker |
| 2003/0150551 A1 | 8/2003 | Baker |
| 2003/0157857 A1 | 8/2003 | Cook et al. |
| 2003/0171729 A1 | 9/2003 | Kaun et al. |
| 2003/0180341 A1 | 9/2003 | Gooch et al. |
| 2003/0199800 A1 | 10/2003 | Levin |
| 2003/0208175 A1 | 11/2003 | Gross et al. |
| 2003/0225383 A1 | 12/2003 | Glaug et al. |
| 2004/0019338 A1 | 1/2004 | Litvay et al. |
| 2004/0019339 A1 | 1/2004 | Ranganathan et al. |
| 2004/0019340 A1 | 1/2004 | McBride |
| 2004/0019342 A1 | 1/2004 | Nagasuna et al. |
| 2004/0024375 A1 | 2/2004 | Litvay |
| 2004/0033750 A1 | 2/2004 | Everett et al. |
| 2004/0049146 A1 | 3/2004 | Kolte et al. |
| 2004/0054343 A1 | 3/2004 | Barnett et al. |
| 2004/0054344 A1 | 3/2004 | Roettger et al. |
| 2004/0065420 A1 | 4/2004 | Graef et al. |
| 2004/0076662 A1 | 4/2004 | Riesinger |
| 2004/0078011 A1 | 4/2004 | Stevens |
| 2004/0078016 A1 | 4/2004 | Baker |
| 2004/0087927 A1 | 5/2004 | Suzuki |
| 2004/0106888 A1 | 6/2004 | Lutri et al. |
| 2004/0111074 A1 | 6/2004 | Eliasson |
| 2004/0127862 A1 | 7/2004 | Bubb et al. |
| 2004/0138602 A1 | 7/2004 | Rossen |
| 2004/0177935 A1 | 9/2004 | Hamed et al. |
| 2004/0181199 A1 | 9/2004 | Moberg-Alehammar et al. |
| 2004/0204696 A1 | 10/2004 | Chen |
| 2004/0230173 A1 | 11/2004 | Barge et al. |
| 2004/0230184 A1 | 11/2004 | Babusik et al. |
| 2004/0243042 A1 | 12/2004 | Lipman |
| 2004/0243080 A1 | 12/2004 | Baer |
| 2004/0243081 A1 | 12/2004 | Suzuki et al. |
| 2004/0253894 A1 | 12/2004 | Fell et al. |
| 2004/0254552 A1 | 12/2004 | Mangold |
| 2005/0008825 A1 | 1/2005 | Casey et al. |
| 2005/0013992 A1 | 1/2005 | Azad et al. |
| 2005/0015036 A1 | 1/2005 | Lutri et al. |
| 2005/0049566 A1 | 3/2005 | Vukos et al. |
| 2005/0079361 A1 | 4/2005 | Hamed et al. |
| 2005/0096616 A1 | 5/2005 | Arora et al. |
| 2005/0112979 A1 | 5/2005 | Sawyer et al. |
| 2005/0119631 A1 | 6/2005 | Giloh et al. |
| 2005/0136773 A1 | 6/2005 | Yahiaoui et al. |
| 2005/0165371 A1 | 7/2005 | Giacometti |
| 2005/0215965 A1 | 9/2005 | Schmidt et al. |
| 2005/0215967 A1 | 9/2005 | Toro et al. |
| 2005/0222547 A1 | 10/2005 | Beruda et al. |
| 2005/0228353 A1 | 10/2005 | Thomas |
| 2005/0261649 A1 | 11/2005 | Cohen |
| 2005/0267429 A1 | 12/2005 | Cohen |
| 2006/0003604 A1 | 1/2006 | Angerpointner |
| 2006/0020250 A1 | 1/2006 | Chester et al. |
| 2006/0058750 A1 | 3/2006 | Di Girolamo et al. |
| 2006/0069366 A1 | 3/2006 | Cole |
| 2006/0069367 A1 | 3/2006 | Waksmundzki et al. |
| 2006/0069375 A1 | 3/2006 | Waksmundzki et al. |
| 2006/0122548 A1 | 6/2006 | Abrams |
| 2006/0122572 A1 | 6/2006 | Suarez |
| 2006/0153904 A1 | 7/2006 | Smith et al. |
| 2006/0161122 A1 | 7/2006 | Erdman et al. |
| 2006/0178650 A1 | 8/2006 | Hakannsson et al. |
| 2006/0184147 A1 | 8/2006 | Hamed |
| 2006/0206073 A1 | 9/2006 | Crane et al. |
| 2006/0206074 A1 | 9/2006 | Bernal et al. |
| 2006/0241542 A1 | 10/2006 | Gudnason et al. |
| 2006/0282028 A1 | 12/2006 | Howard et al. |
| 2007/0073254 A1 | 3/2007 | Ponomarenko et al. |
| 2007/0078467 A1 | 4/2007 | Mullen |
| 2007/0100308 A1 | 5/2007 | Miyairi |
| 2007/0142804 A1 | 6/2007 | Bernard |
| 2007/0167096 A1 | 7/2007 | Scott |
| 2007/0167884 A1 | 7/2007 | Mangrum et al. |
| 2007/0224903 A1 | 9/2007 | Chakravarty et al. |
| 2007/0225663 A1 | 9/2007 | Watt et al. |
| 2007/0254550 A1 | 11/2007 | Hamed et al. |
| 2007/0270070 A1 | 11/2007 | Hamed |
| 2007/0282236 A1 | 12/2007 | LaGreca |
| 2008/0004581 A1 | 1/2008 | Babusik et al. |
| 2008/0015532 A1 | 1/2008 | Waksmundzki |
| 2008/0058691 A1 | 3/2008 | Sorensen |
| 2008/0082075 A1 | 4/2008 | Morrell-Schwartz |
| 2008/0090050 A1 | 4/2008 | Seyler et al. |
| 2008/0091152 A1 | 4/2008 | Asherman |
| 2008/0114317 A1 | 5/2008 | Seyler |
| 2008/0119586 A1 | 5/2008 | Byerly et al. |
| 2008/0147024 A1 | 6/2008 | Potts et al. |
| 2008/0167592 A1 | 7/2008 | Greer |
| 2008/0243100 A1 | 10/2008 | Wu et al. |
| 2008/0255533 A1 | 10/2008 | Wu et al. |
| 2008/0275409 A1 | 11/2008 | Kane et al. |
| 2008/0312621 A1 | 12/2008 | Hundorf et al. |
| 2008/0312622 A1 | 12/2008 | Hundorf et al. |
| 2009/0062760 A1 | 3/2009 | Wright et al. |
| 2009/0076472 A1 | 3/2009 | Goldwasser et al. |
| 2009/0112175 A1 | 4/2009 | Bissah et al. |
| 2009/0126103 A1 | 5/2009 | Dietrich et al. |
| 2009/0204087 A1 | 8/2009 | Herfert et al. |
| 2009/0216168 A1 | 8/2009 | Eckstein et al. |
| 2009/0227935 A1 | 9/2009 | Zanella et al. |
| 2009/0227969 A1 | 9/2009 | Jaeb et al. |
| 2009/0299251 A1 | 12/2009 | Buan |
| 2009/0299255 A1 | 12/2009 | Kazala, Jr. et al. |
| 2010/0010461 A1 | 1/2010 | Herfert et al. |
| 2010/0030171 A1 | 2/2010 | Canada et al. |
| 2010/0036334 A1 | 2/2010 | Heagle et al. |
| 2010/0036342 A1 | 2/2010 | Carlucci et al. |
| 2010/0048072 A1 | 2/2010 | Kauscheke et al. |
| 2010/0055158 A1 | 3/2010 | Vitaris et al. |
| 2010/0069858 A1 | 3/2010 | Olson |
| 2010/0084074 A1 | 4/2010 | McClernon et al. |
| 2010/0087767 A1 | 4/2010 | McNeil |
| 2010/0106120 A1 | 4/2010 | Holm |
| 2010/0106121 A1 | 4/2010 | Holm |
| 2010/0121298 A1 | 5/2010 | Seyler et al. |
| 2010/0125258 A1 | 5/2010 | Coulthard et al. |
| 2010/0168695 A1 | 7/2010 | Robles et al. |
| 2010/0217177 A1 | 8/2010 | Cali et al. |
| 2010/0256545 A1 | 10/2010 | Aali et al. |
| 2010/0256584 A1 | 10/2010 | Litvay |
| 2010/0256586 A1 | 10/2010 | Bergstrom et al. |
| 2010/0262091 A1 | 10/2010 | Larsson |
| 2010/0305526 A1 | 12/2010 | Robinson et al. |
| 2010/0318047 A1 | 12/2010 | Ducker et al. |
| 2010/0318052 A1 | 12/2010 | Ha et al. |
| 2010/0324516 A1 | 12/2010 | Braga et al. |
| 2011/0004172 A1 | 1/2011 | Eckstein et al. |
| 2011/0052664 A1 | 3/2011 | Tennican et al. |
| 2011/0059329 A1 | 3/2011 | Dobrawa et al. |
| 2011/0060303 A1 | 3/2011 | Bissah et al. |
| 2011/0098621 A1 | 4/2011 | Fabo et al. |
| 2011/0125119 A1 | 5/2011 | Weismantel et al. |
| 2011/0152813 A1 | 6/2011 | Ellingson |
| 2011/0178375 A1 | 7/2011 | Forster |
| 2011/0183109 A1 | 7/2011 | Seyler et al. |
| 2011/0184364 A1 | 7/2011 | Biggs et al. |
| 2011/0184370 A1 | 7/2011 | Seyler et al. |
| 2011/0208145 A1 | 8/2011 | Zhang et al. |
| 2011/0213286 A1 | 9/2011 | Riesinger |
| 2011/0223413 A1 | 9/2011 | Herfert et al. |
| 2011/0238026 A1 | 9/2011 | Zhang et al. |
| 2011/0247636 A1 | 10/2011 | Pollack |
| 2011/0257572 A1 | 10/2011 | Locke et al. |
| 2011/0268932 A1 | 11/2011 | Catalan et al. |
| 2012/0004632 A1 | 1/2012 | Zhang et al. |
| 2012/0045639 A1 | 2/2012 | Whitmore et al. |
| 2012/0053547 A1 | 3/2012 | Schroeder et al. |
| 2012/0071848 A1 | 3/2012 | Zhang et al. |
| 2012/0095426 A1 | 4/2012 | Visscher et al. |
| 2012/0101465 A1 | 4/2012 | Mcguire, Jr. |
| 2012/0136329 A1 | 5/2012 | Carney |
| 2012/0143158 A1 | 6/2012 | Yang et al. |

(56) References Cited

U.S. PATENT DOCUMENTS

| | | |
|---|---|---|
| 2012/0197229 A1 | 8/2012 | Buan |
| 2012/0203145 A1 | 8/2012 | Nilsson |
| 2012/0203189 A1 | 8/2012 | Barta et al. |
| 2012/0220968 A1 | 8/2012 | Confalone et al. |
| 2012/0232502 A1 | 9/2012 | Lowing |
| 2012/0238932 A1 | 9/2012 | Atteia et al. |
| 2012/0283529 A1 | 11/2012 | Marchand et al. |
| 2012/0302440 A1 | 11/2012 | Theliander et al. |
| 2012/0308780 A1 | 12/2012 | Rottger et al. |
| 2012/0310186 A1 | 12/2012 | Moghe et al. |
| 2012/0310197 A1 | 12/2012 | Thomas |
| 2012/0330253 A1 | 12/2012 | Robinson et al. |
| 2013/0012902 A1 | 1/2013 | Rovaniemi |
| 2013/0150814 A1 | 6/2013 | Buan |
| 2013/0310781 A1 | 11/2013 | Phillips et al. |
| 2014/0114268 A1 | 4/2014 | Auguste et al. |
| 2014/0249495 A1 | 9/2014 | Mumby |
| 2015/0159066 A1 | 6/2015 | Hartwell et al. |
| 2015/0174304 A1 | 6/2015 | Askem et al. |

FOREIGN PATENT DOCUMENTS

| | | |
|---|---|---|
| EP | 0 541 251 | 5/1993 |
| EP | 0 549 781 | 9/1996 |
| EP | 0 748 894 | 12/1996 |
| EP | 0 599 871 | 4/1997 |
| EP | 0 875 224 | 11/1998 |
| EP | 1 013 290 | 6/2000 |
| EP | 1 048 278 | 11/2000 |
| EP | 1 066 809 | 1/2001 |
| EP | 1 139 951 | 10/2001 |
| EP | 1 312 328 | 5/2003 |
| EP | 1 452 156 | 9/2004 |
| EP | 2 161 011 | 3/2010 |
| EP | 2 263 627 | 12/2010 |
| EP | 2 366 721 | 9/2011 |
| EP | 2 529 767 | 12/2012 |
| GB | 2355228 | 4/2001 |
| GB | 2435422 | 8/2007 |
| GB | 2435423 | 8/2007 |
| GB | 2489947 | 10/2012 |
| JP | S57-119738 | 7/1982 |
| JP | 2001-145655 | 5/2001 |
| JP | 2007-275185 | 10/2007 |
| JP | 2008-119497 | 5/2008 |
| WO | WO 1991/11161 | 8/1991 |
| WO | WO 1991/11162 | 8/1991 |
| WO | WO 1993/01778 | 2/1993 |
| WO | WO 1993/01779 | 2/1993 |
| WO | WO 1993/01780 | 2/1993 |
| WO | WO 1993/01781 | 2/1993 |
| WO | WO 1993/09745 | 5/1993 |
| WO | WO 1993/11726 | 6/1993 |
| WO | WO 1995/13042 | 5/1995 |
| WO | WO 1995/13776 | 5/1995 |
| WO | WO 1995/13779 | 5/1995 |
| WO | WO 1995/14451 | 6/1995 |
| WO | WO 1995/16424 | 6/1995 |
| WO | WO 1996/07783 | 3/1996 |
| WO | WO 1996/21410 | 7/1996 |
| WO | WO 1997/14384 | 4/1997 |
| WO | WO 1998/20916 | 5/1998 |
| WO | WO 1998/22279 | 5/1998 |
| WO | WO 1999/04830 | 2/1999 |
| WO | WO 1999/39671 | 8/1999 |
| WO | WO 1999/45876 | 9/1999 |
| WO | WO 1999/45878 | 9/1999 |
| WO | WO 1999/56687 | 11/1999 |
| WO | WO 2000/00016 | 1/2000 |
| WO | WO 2000/00127 | 1/2000 |
| WO | WO 2000/00129 | 1/2000 |
| WO | WO 2000/00130 | 1/2000 |
| WO | WO 2000/00131 | 1/2000 |
| WO | WO 2000/40190 | 7/2000 |
| WO | WO 2000/59438 | 10/2000 |
| WO | WO 2001/072251 | 10/2001 |
| WO | WO 2001/90465 | 11/2001 |
| WO | WO 2002/24132 | 3/2002 |
| WO | WO 2002/38096 | 5/2002 |
| WO | WO 2002/076379 | 10/2002 |
| WO | WO 2003/073971 | 9/2003 |
| WO | WO 2004/043321 | 5/2004 |
| WO | WO 2004/073566 | 9/2004 |
| WO | WO 2004/098474 | 11/2004 |
| WO | WO 2006/105305 | 10/2006 |
| WO | WO 2007/035038 | 3/2007 |
| WO | WO 2007/040606 | 4/2007 |
| WO | WO 2007/077214 | 7/2007 |
| WO | WO 2007/077216 | 7/2007 |
| WO | WO 2007/116347 | 10/2007 |
| WO | WO 2008/049277 | 5/2008 |
| WO | WO 2008/131895 | 11/2008 |
| WO | WO 2009/146441 | 3/2009 |
| WO | WO 2009/066104 | 5/2009 |
| WO | WO 2009/066105 | 5/2009 |
| WO | WO 2009/152021 | 12/2009 |
| WO | WO 2010/032951 | 3/2010 |
| WO | WO 2010/089448 | 8/2010 |
| WO | WO 2010/139926 | 12/2010 |
| WO | WO 2011/058311 | 5/2011 |
| WO | WO 2011/080427 | 7/2011 |
| WO | WO 2011/113728 | 9/2011 |
| WO | WO 2011/115908 | 9/2011 |
| WO | WO 2011/152368 | 12/2011 |
| WO | WO 2012/009370 | 1/2012 |
| WO | WO 2012/035787 | 3/2012 |
| WO | WO 2012/074512 | 6/2012 |
| WO | WO 2012/146656 | 11/2012 |
| WO | WO 2012/168298 | 12/2012 |
| WO | WO 2013/014317 | 1/2013 |
| WO | WO 2013/029652 | 3/2013 |
| WO | WO 2013/060732 | 5/2013 |
| WO | WO 2013/136181 | 11/2013 |
| ZA | 9605526 | 2/1997 |

OTHER PUBLICATIONS

U.S. Appl. No. 15/261,752, filed Sep. 9, 2016, Mumby et al.
International Search Report and Written Opinion re PCT/GB2012/000587, dated Oct. 8, 2013.
International Preliminary Report on Patentability, re PCT Application No. PCT/GB2012/000587, dated Jan. 23, 2014.

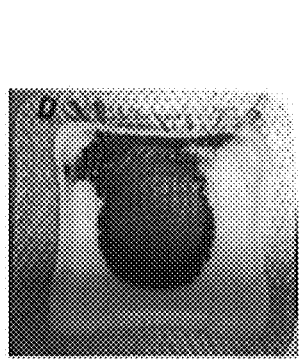 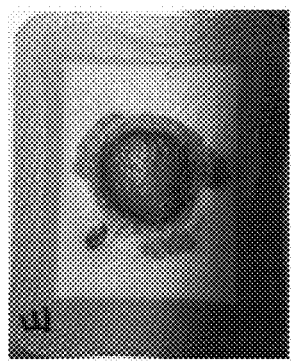 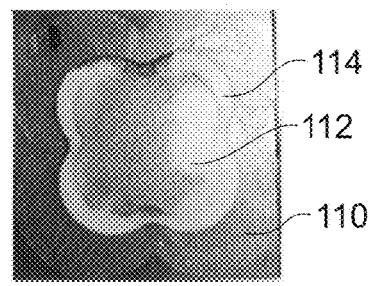
FIG. 3A     FIG. 3B     FIG. 3C
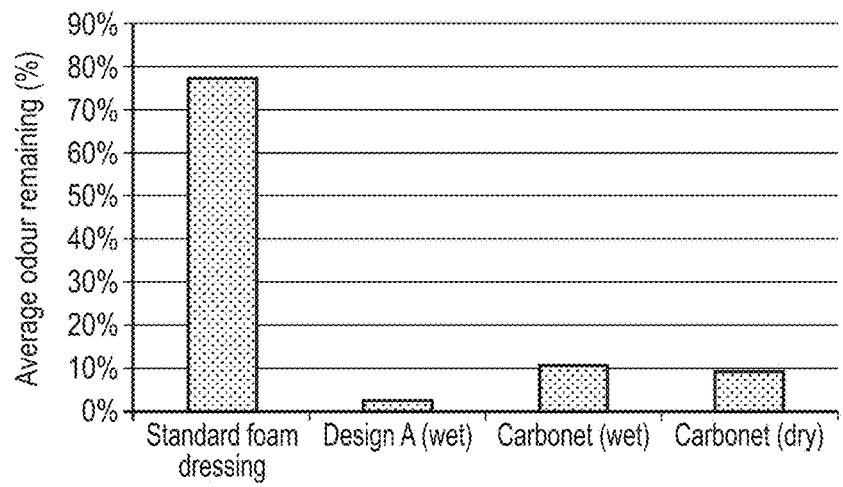
FIG. 4
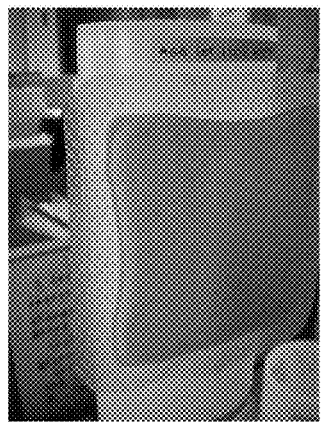 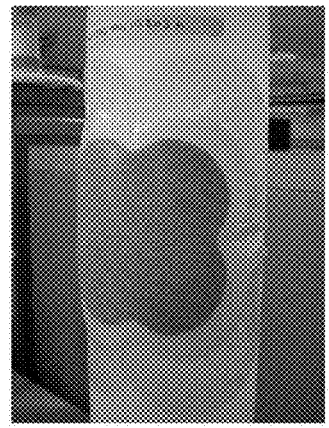
FIG. 5

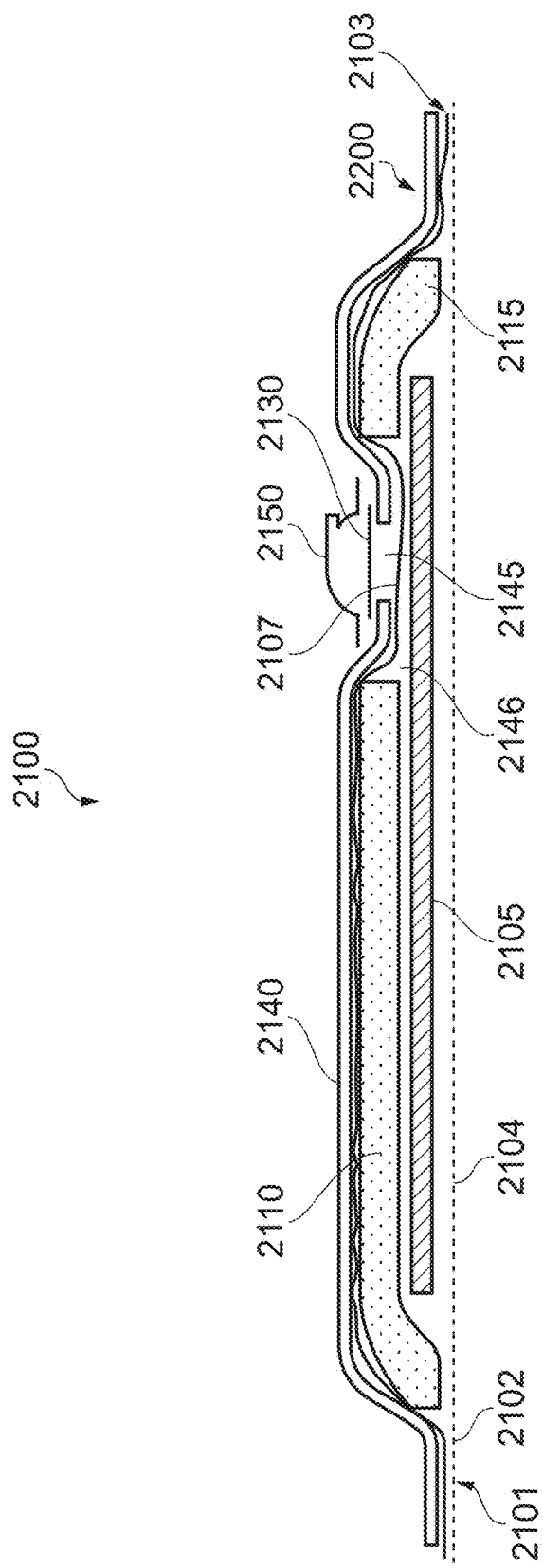

WOUND DRESSING AND METHOD OF TREATMENT

CROSS-REFERENCE TO RELATED APPLICATIONS

This application is continuation of U.S. application Ser. No. 14/232,607, having a 371(c) date of May 21, 2014, which is a U.S. National Phase of the PCT International Application No. PCT/GB2012/000587, filed on Jul. 12, 2012, which claims priority to UK Application Nos. 1112084.7 and 1211171.2, filed on Jul. 14, 2011 and Jun. 22, 2012, respectively.

Some embodiments of the present disclosure relate to a wound dressing and a method of treatment. In particular, but not exclusively, the present disclosure relates to an apparatus and method for providing protection at a wound site, for absorbing wound exudate, and providing a number of benefits to both users and those around them over known techniques.

Patients have to live with chronic or acute wounds for durations ranging from a number of days to a number of years. Their quality of life is unavoidably affected, and even more so if the impact of the wound on patients' daily activities cannot be minimised by the dressing chosen.

Patients often report fear of the dressing leaking, of odour from the wound incommoding their relatives, or of the dressing becoming unsightly as it is being used. As patients move, the dressing may be submitted to stretching and/or bending of the skin, or rubbing from clothes or bed linen. While modern dressings are designed to stretch to some extent, lifting of the dressing borders during everyday activities does occur, and reinforces concerns about leakage and odour. The corresponding worry about stigma, and cleanliness, can limit a patient's activities in a way that is not beneficial to their overall healing.

In addition, when patients are mobile, fear of damaging their wound further through painful knocks is also present.

The every-day life of patients with a wound can be seen as a balance of risks and benefits. The decisions taken by patients can sometimes go against the prescribed treatment or behaviour recommended by clinicians. Addressing some of the patients' concerns about the state of their dressing while they are wearing it could help to steer patient decisions towards concording with the clinician's recommendations.

In summary, the above-mentioned problems have heretofore been approached in the following ways:

Prevention of leaks: wound dressing have resorted to the use of superabsorbers in their construction to try to limit leakage of wound exudates out of the dressing pad. EP1156838 describes a wound dressing which combines a foam layer and an absorbent layer in intimate contact with the foam, and capable of draining the foam. EP0758219 describes a method for producing such an article.

Odour: several odour control dressings exist, including either activated charcoal layers (Carboflex®, Askina Carbosorb®, Sorbsan plus Carbon®, Carbonet®, Lyofoam C®) or cyclodextrins embedded into a hydrocolloid (ExuDerm Odorshield®, Avery Dennison). Where activated charcoal is used, it is most often placed behind a barrier layer, the intent of which is to keep the charcoal as dry as possible to enable it to trap odours. U.S. Pat. No. 6,348,423 describes an odour-control absorbent dressing, which contains a barrier layer between the wound side of the pad and its odour layer. GB2420286 describes the use of activated charcoal to control wound odour. WO0209782 describes the use of cyclodextrins incorporated into a non-adhering wound dressing. No adhering absorbent dressing also containing a means of controlling odour is currently available on the market.

Conformability and movement: some dressings have been designed to be more conformable to the body than a standard square shape. This is the case for example of dressings design especially for the heel area, or for the sacrum area. WO2008/149107 describes a sacrum dressing with preferential folding lines. In such dressings, both the border and the pad of the dressing can be shaped in relationship to the particular area of the body targeted. WO2004/047695 describes a dressing with indentation in its pad in a honeycomb pattern. Further related patent applications describe other beneficial formats of indentations. An existing product, Comfeel Plus® by Coloplast, has a shaped border which is claimed to increase adhesion and conformability. Furthermore, EP0902672 describes a conformable dressing which has a permanent set after application.

Appearance and cleanliness do not seem to be addressed by existing product offerings, or to have been considered an issue for the patient in the published literature.

Protection from shocks and pressure relief: This problem seems to have been tackled in the industry in the light of preventing pressure ulcers from developing or worsening. It is generally accepted that structures containing air bubbles or gel parts will be able to absorb some of the energy put into compressing a dressing, until the force applied leads to the collapse of the dressing thickness. Foam dressings have therefore been used as part of a pressure relief protocol in clinical settings, but in conjunction with other methods.

WO2007/075379 describes a bi-component dressing, where a first part is formed as a wall around the circumference of the wound, and a second, flatter part, is placed on top of the wall. Pressure applied over a wider area than that delimited by the wall, such as under a compression bandage, would be mostly taken up by the shield structure.

WO2006/091735 and US2009/0069737 describe a similar concept, where a layer of material is punctured. EP1164995 builds on this idea, where a pressure-relieving structure surrounds an absorbent part of the dressing, and is in contact with the skin.

WO2011/144888 describes the use of a three-dimensional knit within a dressing.

The inventors have not found a structure described that meets more than one of the patient needs outlined above. However, patient satisfaction with a particular treatment, and therefore the likelihood that they will comply with it, depends on several clinical and social factors.

According to a first aspect of the present disclosure, there is provided a wound dressing for providing protection at a wound site, comprising:
  an absorbent layer for absorbing wound exudate; and
  an obscuring element for at least partially obscuring a view of wound exudate absorbed by the absorbent layer in use.

According to a second aspect of the present disclosure, there is provided a method of manufacturing a wound dressing, comprising:
  providing an absorbent layer for absorbing wound exudate; and
  providing an obscuring element for at least partially obscuring a view of wound exudate absorbed by the absorbent layer in use.

According to a third aspect of the present disclosure, there is provided a wound dressing for providing protection at a wound site, comprising:
  an absorbent layer for absorbing wound exudate; and a shielding layer provided over the absorbent layer, and further from a wound-facing side of the wound dressing than the absorbent layer.

According to a fourth aspect of the present disclosure, there is provided a method of manufacturing a wound dressing, comprising:
providing an absorbent layer for absorbing wound exudate; and
providing a shielding layer over the absorbent layer, and further from a wound-facing side of the wound dressing than the absorbent layer.

According to a fifth aspect of the present disclosure, there is provided a wound dressing for providing protection at a wound site, comprising:
a shielding layer for spreading pressure applied to the wound dressing over an area larger than the area where the pressure is applied; and
a cover layer provided adjacent to and over the shielding layer, on a non-wound facing side of the wound dressing.

According to a sixth aspect of the present disclosure, there is provided a method of manufacturing a wound dressing, comprising
providing a shielding layer for spreading pressure applied to the wound dressing over an area larger than the area where the pressure is applied; and
providing a cover layer provided adjacent to and over the shielding layer, on a non-wound facing side of the wound dressing.

According to a seventh aspect of the present disclosure, there is provided a wound dressing, comprising:
an absorbent layer for absorbing wound exudate;
a fluid transmission layer; and
an odour controlling element between or in the fluid transmission layer and the absorbent layer.

According to an eighth aspect of the present disclosure, there is provided a method of manufacturing a wound dressing, comprising
providing an absorbent layer for absorbing wound exudate;
providing a fluid transmission layer; and
providing an odour controlling element between or in the fluid transmission layer and the absorbent layer.

According to a ninth aspect of the present disclosure, there is provided a wound dressing, comprising: an odour control material and at least one of a foam, an absorbent layer and a shielding layer, wherein the odour control material is incorporated into the at least one other material.

According to a tenth aspect of the present disclosure, there is provided a method of manufacturing a wound dressing, comprising providing an odour control material and at least one of a foam, an absorbent layer and a shielding layer, wherein the odour control material is incorporated into the at least one other material.

According to an eleventh aspect of the present disclosure, there is provided a wound dressing, comprising:
an absorbent layer for absorbing wound exudate,
wherein the dressing is shaped to include sub-areas, wherein the dressing has rotational symmetry, and the sub areas define areas of the dressing that are formable in different directions with respect to each other.

According to a twelfth aspect of the present disclosure, there is provided a method of manufacturing a wound dressing comprising
providing an absorbent layer for absorbing wound exudate,
and shaping the dressing to include sub-areas, wherein the dressing has rotational symmetry, and the sub areas define areas of the dressing that are formable in different directions with respect to each other.

Certain embodiments of the present disclosure provide the advantage that a wound dressing is provided that has a reduced aesthetic impact for users (compared to known dressings) yet allows clinicians to examine and visually assess the wound area, such as assessing presence of blood, infection by-products and/or the extent of exudate spread across the dressing.

Certain embodiments of the present disclosure provide the advantage that a wound dressing is provided that has improved conformability to an area of a patient to which it is attached, particularly for areas that are not flat/planar.

Certain embodiments of the present disclosure provide the advantage that a wound dressing is provided that has improved performance in terms of protecting a user from shocks or pressure.

Certain embodiments of the present disclosure provide the advantage that odour from a wound is controlled.

Some embodiments provide the advantage that the wound dressing can be used to collect wound exudate generated during a negative pressure therapy process. A pump remote from the wound dressing or supported thereby can be connected to the wound dressing and reused (or can be disposable) whilst the wound dressing itself is used to collect wound exudate and may then be disposed of after use. The pump or other source of negative pressure can be connected to the wound dressing through a flexible tubing or conduit. In this arrangement, negative pressure can draw wound exudate and other fluids or secretions away from the wound site.

Any of the embodiments disclosed herein are suitable for use with and, hence, can be used with a negative pressure wound therapy system to aid in wound closure and healing in which wound exudate drawn from a wound site during the therapy is collected and stored in a wound dressing and/or in a collection canister.

It is the aim of some wound dressing embodiments disclosed herein to have an increased capacity for absorbing wound exudate reducing the frequency with which the dressings must be changed. It is further an aim of certain wound dressing embodiments disclosed herein to manage the movement of wound exudate through a dressing to avoid blockages occurring that lead to reduced life of the dressing.

It is an aim of some wound dressing embodiments of the present disclosure to provide a wound dressing having an increased capacity to absorb compressive forces exerted on the wound dressing.

It is an aim of some wound dressing embodiments disclosed herein to provide a wound dressing having an increased capacity to prevent shear forces from an outer surface of a wound dressing from being translated into corresponding shear forces at a wound site.

It is an aim of some wound dressing embodiments disclosed herein to provide a wound dressing which can "give" in a direction perpendicular to and parallel to a wound site surface even when the dressing experiences negative pressure.

It is an aim of some wound dressing embodiments disclosed herein to provide a wound dressing able to be used with topical negative pressure therapy which helps maintain an open flow path so that therapy can be continued unhindered by blockages caused by build-up of solid matter.

It is an aim of some wound dressing embodiments disclosed herein to provide a method and apparatus for treating a wound with topical negative pressure therapy by preventing blockage of a flowpath region of a wound dressing.

Some embodiments disclosed herein are directed toward the treatment of wounds with negative pressure wound therapy. In particular, any of the dressing embodiments disclosed herein can be used for absorbing and storing wound exudate in conjunction with a pump, for example a miniaturized pump. Any of the wound dressing embodiments disclosed herein can further comprise a transmission layer configured to transmit wound exudates to an absorbent layer disposed in the wound dressing. Additionally, any of the wound dressing embodiments disclosed herein can be adapted to provide for a port or other fluidic connector configured to retain wound exudate within the wound dressing while transmitting negative pressure to the wound dressing, though such a feature is not required.

According to an embodiment of the present disclosure there is provided a wound treatment apparatus comprising:
a wound dressing comprising:
    any of the dressing embodiments disclosed herein;
    a pump; and
    a suction port for applying negative pressure to the wound dressing for the application of topical negative pressure at a wound site, the suction port comprising:
        a connector portion for connecting the suction port to the pump;
        a sealing surface for sealing the suction port to the cover layer of the wound dressing; and
        a liquid impermeable gas permeable filter element arranged to prevent a liquid from entering the connector portion.

According to another embodiment of the present disclosure there is provided a method for the treatment of a wound comprising:
    providing a wound dressing comprising any of the features or combination of features of any of the dressing embodiments disclosed herein, and/or:
        a transmission layer comprising a 3D knitted or fabric material;
        an absorbent layer for absorbing wound exudate, the absorbent layer overlying the transmission layer;
        a cover layer overlying the absorbent layer and comprising an orifice, wherein the cover layer is moisture vapor permeable;
    positioning the dressing over a wound site to form a sealed cavity over the wound site; and
    applying negative pressure to the wound site to draw fluid through the transmission layer into the absorbent layer.

According to another embodiment of the present disclosure there is provided a wound dressing for providing protection at a wound site, comprising any of the features or combination of features of any of the dressing embodiments disclosed herein, and/or:
    a transmission layer comprising a first surface and a further surface spaced apart from the first surface by a relax distance in a relaxed mode of operation; and
    a plurality of spacer elements extending between the first and further surfaces and, in a forced mode of operation, locatable whereby the first and further surfaces are spaced apart by a compression distance less than the relax distance.

According to another embodiment of the present disclosure there is provided a method for providing protection at a wound site, comprising:
    locating a wound dressing comprising any of the components or features of any of the wound dressing embodiments disclosed herein, and/or a transmission layer over a wound site; and
    responsive to a force on the wound dressing, displacing a plurality of spacer elements extending between a first surface and a further surface of the transmission layer whereby;
    a distance between the first and further surfaces is reduced as the spacer elements are displaced.

According to another embodiment of the present disclosure there is provided an apparatus for dressing a wound for the application of topical negative pressure at a wound site, comprising a wound dressing comprising any of the components or features of any of the wound dressing embodiments disclosed herein, and/or:
    a liquid and gas permeable transmission layer;
    an absorbent layer for absorbing wound exudate, the absorbent layer overlying the transmission layer;
    a gas impermeable cover layer overlying the absorbent layer and comprising a first orifice, wherein the cover layer is moisture vapor permeable.

According to a further embodiment of the present disclosure there is provided a method of applying TNP at a wound site, comprising:
    applying negative pressure at an orifice of a cover layer of any wound dressing embodiment disclosed herein, a peripheral region around the wound site being sealed with the wound dressing, such that air and wound exudate are drawn towards the orifice;
    collecting wound exudate, drawn from the wound site, through a transmission layer of the wound dressing, in an absorbent layer of the wound dressing; and
    transpiring a water component of the wound exudate collected in the absorbent layer through the cover layer of the wound dressing.

According to an additional embodiment of the present disclosure there is provided apparatus for dressing a wound for the application of topical negative pressure at a wound site, comprising a wound dressing comprising any of the components or features of any wound dressing embodiment disclosed herein, and/or:
    a liquid and gas permeable transmission layer;
    an absorbent layer for absorbing wound exudate;
    a gas impermeable cover layer overlying the absorbent layer and the transmission layer, the cover layer comprising an orifice connected to the transmission layer; and
    at least one element configured to reduce the rate at which wound exudate moves towards the orifice when a negative pressure is applied at the orifice.

According to another embodiment of the present disclosure there is provided a method of applying TNP at a wound site, comprising:
    applying negative pressure at an orifice of a cover layer of a wound dressing comprising any of the components or features of any wound dressing embodiment disclosed herein, a peripheral region around the wound site being sealed with the wound dressing such that air and wound exudate move towards the orifice;
    collecting wound exudate, from the wound site, through a transmission layer of the wound dressing, in an absorbent layer of the wound dressing; and
    reducing the rate at which wound exudate moves towards the orifice.

According to still another embodiment of the present disclosure there is provided an apparatus for dressing a wound for the application of topical negative pressure at a wound site, comprising a wound dressing comprising any of the components or features of any wound dressing embodiment disclosed herein and/or:

an absorbent layer for absorbing wound exudate;
a gas impermeable cover layer overlying the absorbent layer the cover layer comprising at least one orifice configured to allow negative pressure to be communicated through the cover layer in at least two spaced apart regions.

According to an additional embodiment of the present disclosure there is provided a method of applying TNP at a wound site, comprising:

sealing a cover layer of a wound dressing comprising any of the components or features of any wound dressing embodiment disclosed herein around the wound site;
applying negative pressure at at least one orifice in the cover layer, said at least one orifice configured to allow negative pressure to be communicated through the cover layer in at (east two spaced apart regions; and
collecting wound exudate, from the wound site, in an absorbent layer of the wound dressing.

According to another embodiment of the present disclosure there is provided a suction port for applying negative pressure to a wound dressing of any of the embodiments disclosed herein or having any of the components or features of any wound dressing embodiment disclosed herein for the application of topical negative pressure at a wound site, the suction port comprising:

a connector portion for connecting the suction port to a source of negative pressure;
a sealing surface for sealing the suction port to a cover layer of a wound dressing; and
a liquid impermeable gas permeable filter element arranged to prevent a liquid entering the connector portion.

According to an additional embodiment of the present disclosure there is provided a method of communicating negative pressure to comprising a wound dressing of any of the embodiments disclosed herein or having any of the components or features of any wound dressing embodiment disclosed herein for the application of topical negative pressure at a wound site, comprising:

applying negative pressure at a connecting portion of a suction port sealed around a perimeter of an orifice in a cover layer of the wound dressing;
filtering gas drawn from within the wound dressing through a liquid impermeable gas permeable filter element of the suction port.

According to another embodiment of the present disclosure there is provided a method of manufacturing a suction port for applying negative pressure to a wound dressing for the application of topical negative pressure at a wound site, the suction port having a connector portion for connecting the suction port to a source of negative pressure and a sealing surface for sealing the suction port to a cover layer of a wound dressing of any of the embodiments disclosed herein or having any of the components or features of any wound dressing embodiment disclosed herein, the method comprising:

disposing a liquid impermeable gas permeable filter element of the suction port at a location to prevent a liquid entering the connector portion.

According to yet another embodiment of the present disclosure there is provided an apparatus for the application of TNP therapy to a wound site, comprising:

a first layer comprising a plurality of openings each having a first open area;
a further layer spaced apart from the first layer comprising a plurality of further openings each having a further open area; and
an air impermeable, moisture vapor permeable cover layer over the first and further layers; wherein
a region between the first and further layers comprises a portion of a flow path for air and/or wound exudate flowing from a wound site and said first open area is less than said further open area.

According to still another embodiment of the present disclosure there is provided a method of applying TNP therapy to a wound site, comprising:

via a vacuum pump in fluid communication with a wound dressing of any of the embodiments disclosed herein or having any of the components or features of any wound dressing embodiment disclosed herein located over a wound site, applying a negative pressure at the wound site; and
as liquid evaporates through a cover layer of the dressing, preventing blockage of a fluid flowpath region of the wound dressing.

Some embodiments provide a wound dressing of any of the embodiments disclosed herein or having any of the components or features of any wound dressing embodiment disclosed herein which even when under negative pressure conditions is able to provide further "give" to buffer compression forces from harming a wound.

Some embodiments provide a wound dressing of any of the embodiments disclosed herein or having any of the components or features of any wound dressing embodiment disclosed herein able to disconnect shear forces applied to the dressing from the wound site covered by the dressing. As a result damage to the wound can be wholly or at least partially avoided.

Some embodiments provide the advantage that a wound site can be covered with a wound dressing of any of the embodiments disclosed herein or having any of the components or features of any wound dressing embodiment disclosed herein which is simultaneously able to deliver negative pressure wound therapy to a wound site, collect exudate and provide protection from forces operating on the dressing.

Some embodiments provide the advantage that forces operating on a wound dressing of any of the embodiments disclosed herein or having any of the components or features of any wound dressing embodiment disclosed herein can be offset by dissipating loads operating over a relatively small distance on an upper layer of the dressing to a relatively larger area on a lower surface of the dressing. The force is thus dissipated over a larger area thus reducing the effect of the force.

Some embodiments provide the advantage that a wound dressing of any of the embodiments disclosed herein or having any of the components or features of any wound dressing embodiment disclosed herein can be used to collect wound exudate generated during a negative pressure therapy process, whilst extending the useful lifetime of the dressing by transpiring a water component of the wound exudate. A pump remote from the wound dressing can be connected to the wound dressing and reused whilst the wound dressing itself is used to collect wound exudate and may then be disposed of after use.

Some embodiments provide a wound dressing and/or method of applying topical negative pressure in which a flowpath through a wound dressing of any of the embodiments disclosed herein or having any of the components or features of any wound dressing embodiment disclosed herein is kept open so that therapy can be continued for as long as desired by a care giver.

Some embodiments prevent solid material, which may cause a blockage, from entering a flowpath region in a wound dressing of any of the embodiments disclosed herein or having any of the components or features of any wound dressing embodiment disclosed herein by using a layer of the dressing to act as a bar to such material.

Some embodiments prevent build-up of solid material in a flowpath region of a wound dressing of any of the embodiments disclosed herein or having any of the components or features of any wound dressing embodiment disclosed herein by ensuring that any solid material that enters into that flowpath region can always escape into a further region of the dressing.

Some embodiments provide the advantage that the build-up of solid material in a flowpath in a wound dressing of any of the embodiments disclosed herein or having any of the components or features of any wound dressing embodiment disclosed herein is avoided by having an absorbent layer close to the flowpath region store liquid over time. This helps keep the environment of the flowpath region moist which helps avoid crusting.

Some embodiments provide the advantage that a wound dressing of any of the embodiments disclosed herein or having any of the components or features of any wound dressing embodiment disclosed herein can be used to collect wound exudate generated during a negative pressure therapy process, whilst extending the useful lifetime of the dressing by transpiring a water component of the wound exudate. A pump remote from the wound dressing can be connected to the wound dressing and reused whilst the wound dressing itself is used to collect wound exudate and may then be disposed of after use. Embodiments of the present disclosure are further described hereinafter with reference to the accompanying drawings, in which:

FIG. 3 illustrates 2 known dressings (a) and (b) and an embodiment of a dressing (c) of the present disclosure;

FIG. 4 illustrates a graph of odour capture ability of various wound dressings;

FIG. 5 shows photographs of a prior art dressing and an embodiment of a dressing of the present disclosure;

FIG. 15A illustrates an embodiment of a wound dressing;

Figure 29:
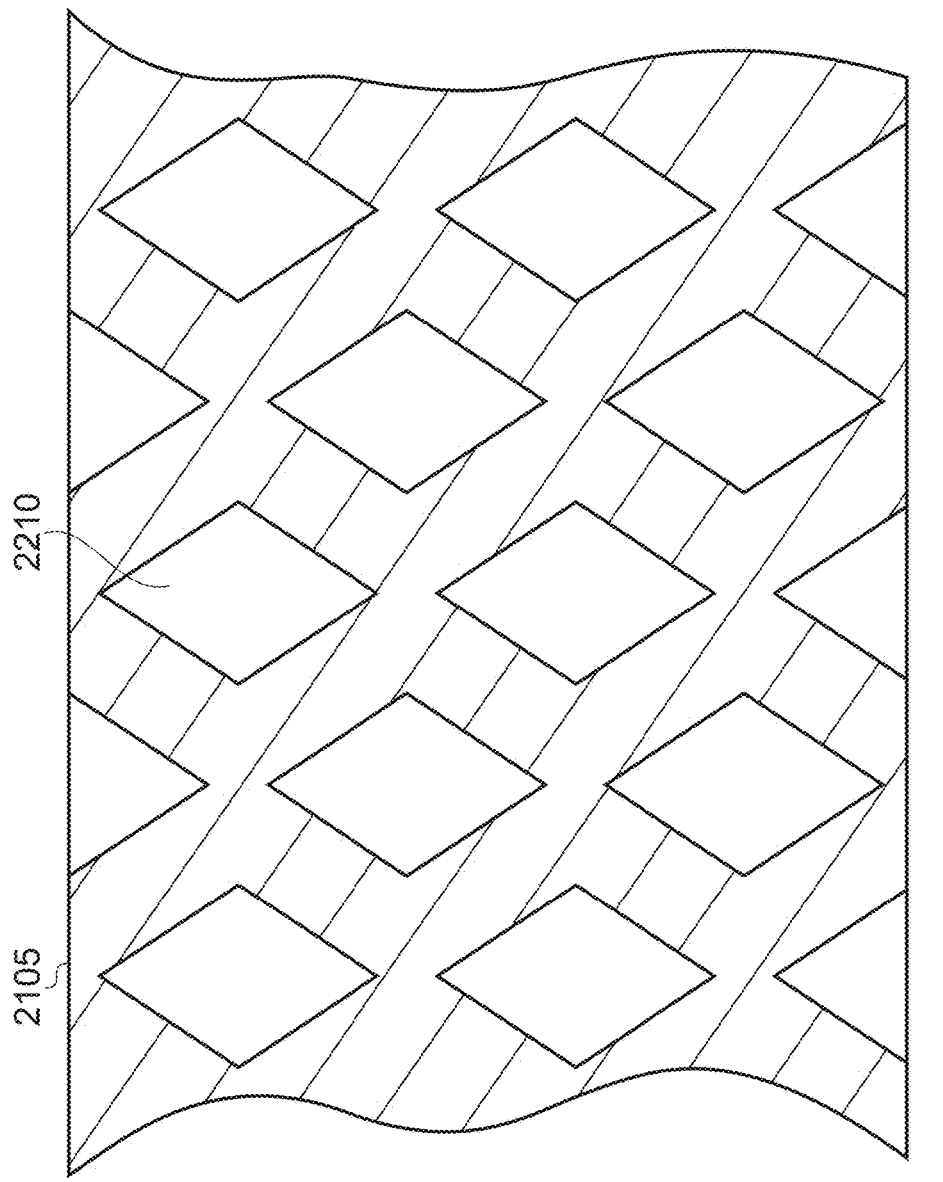
Figure 30:
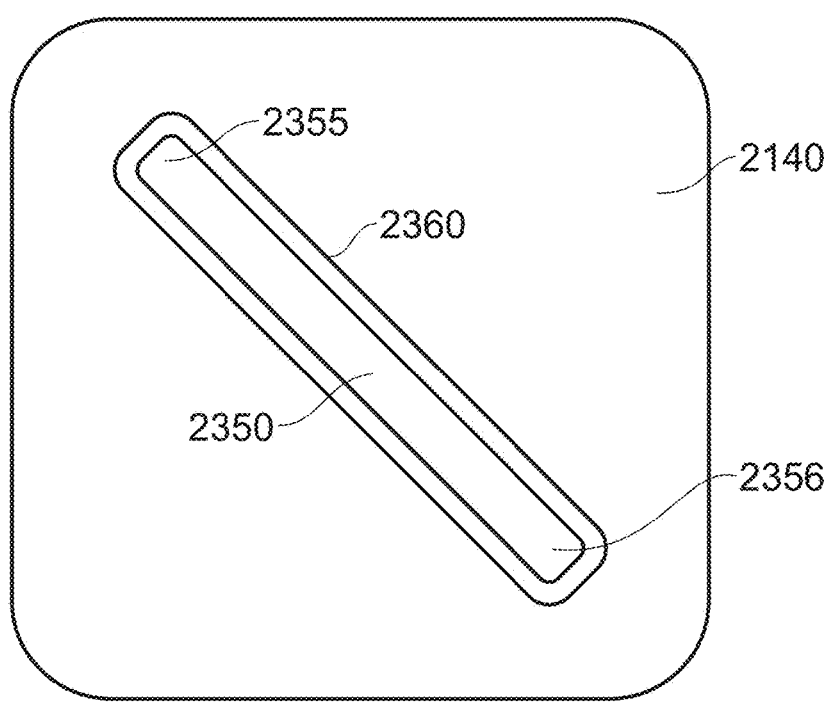
Figure 31:
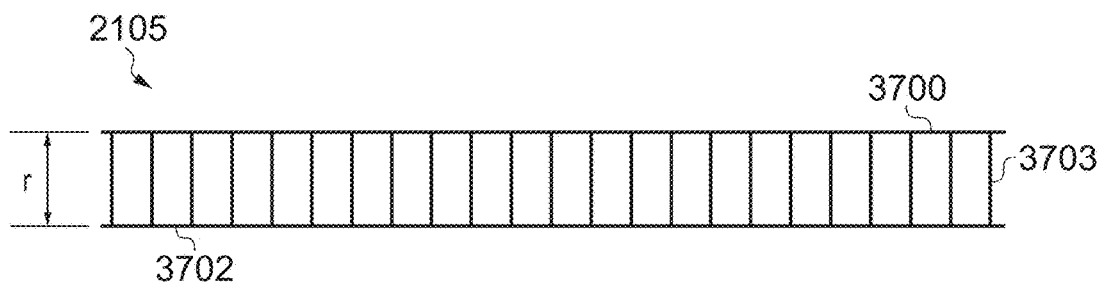
Figure 32:
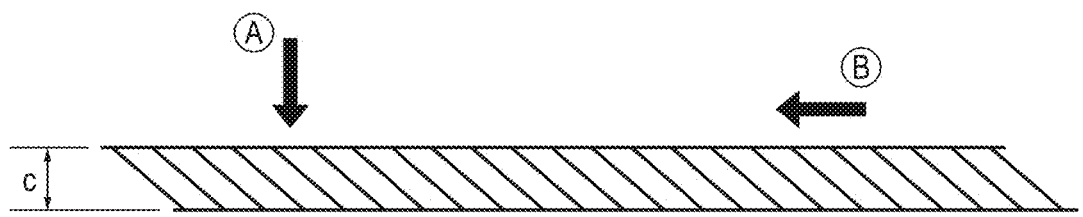
Figure 33:
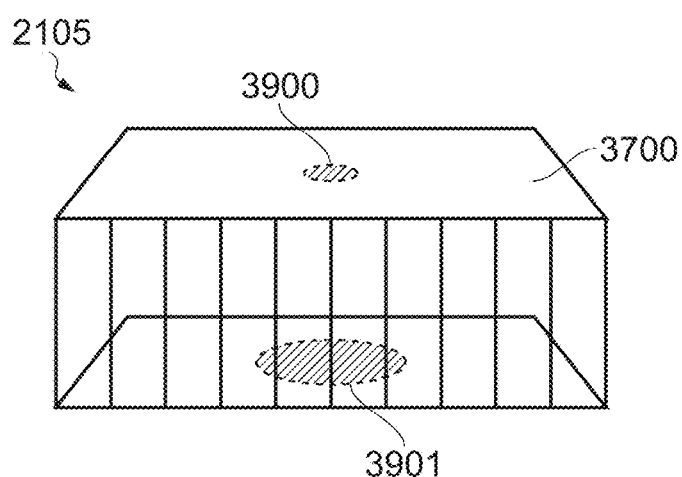
Figure 34:
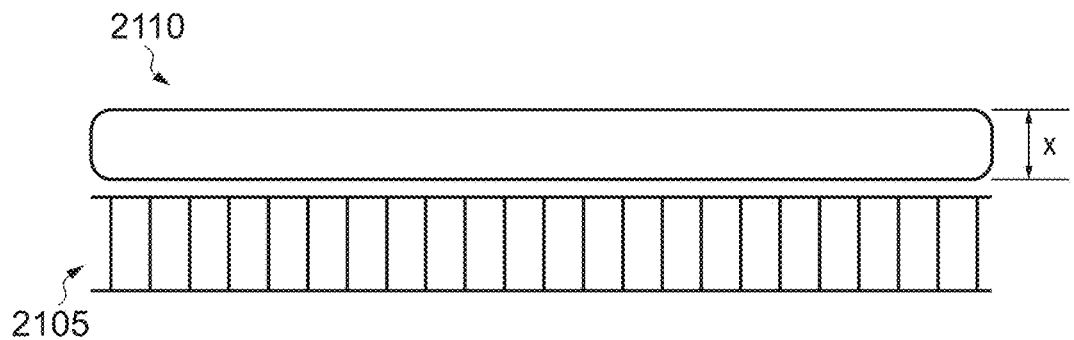
Figure 35:
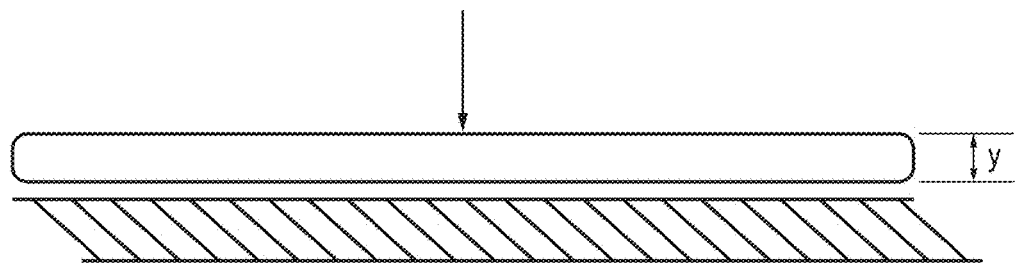
Figure 36:
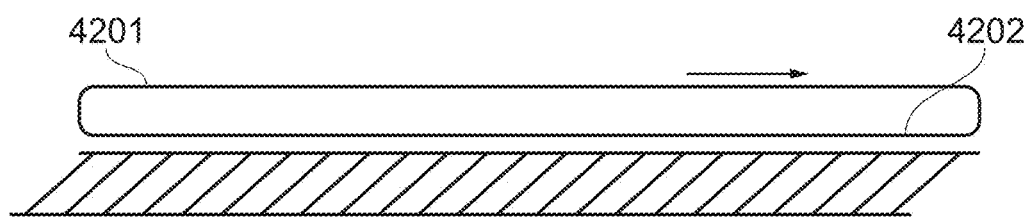
Figure 37:
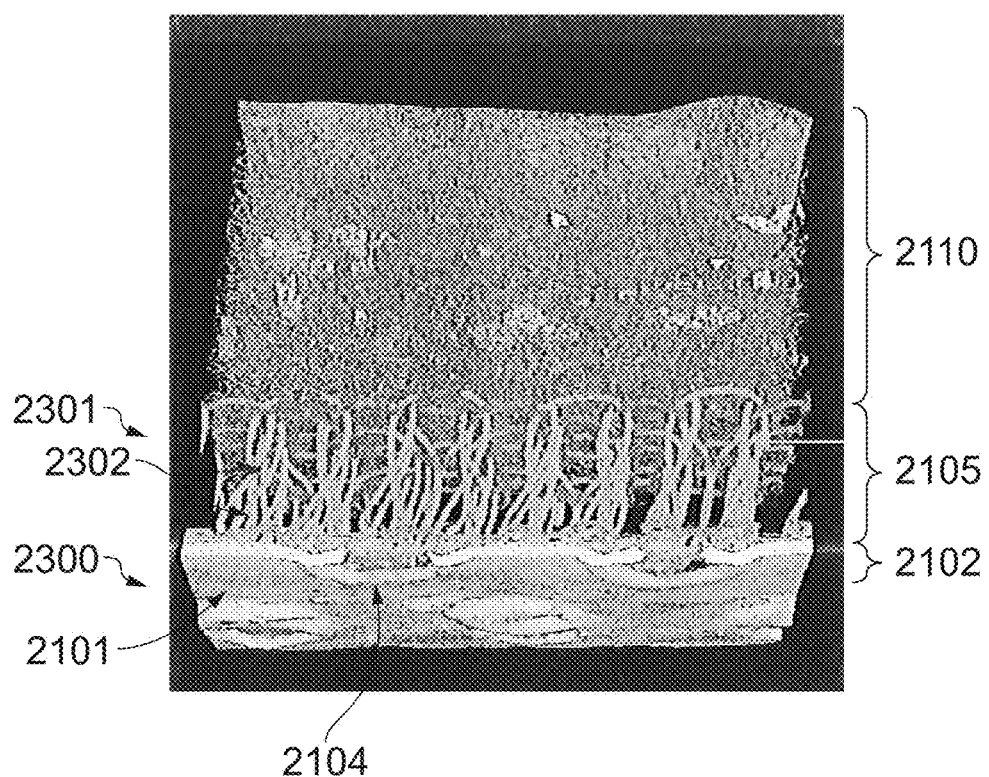
Figure 38:
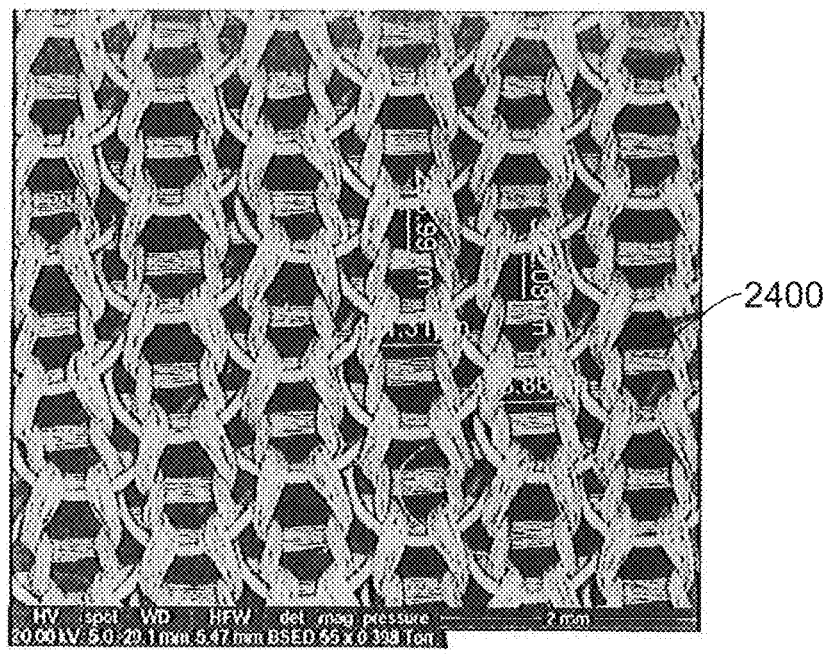
Figure 39:
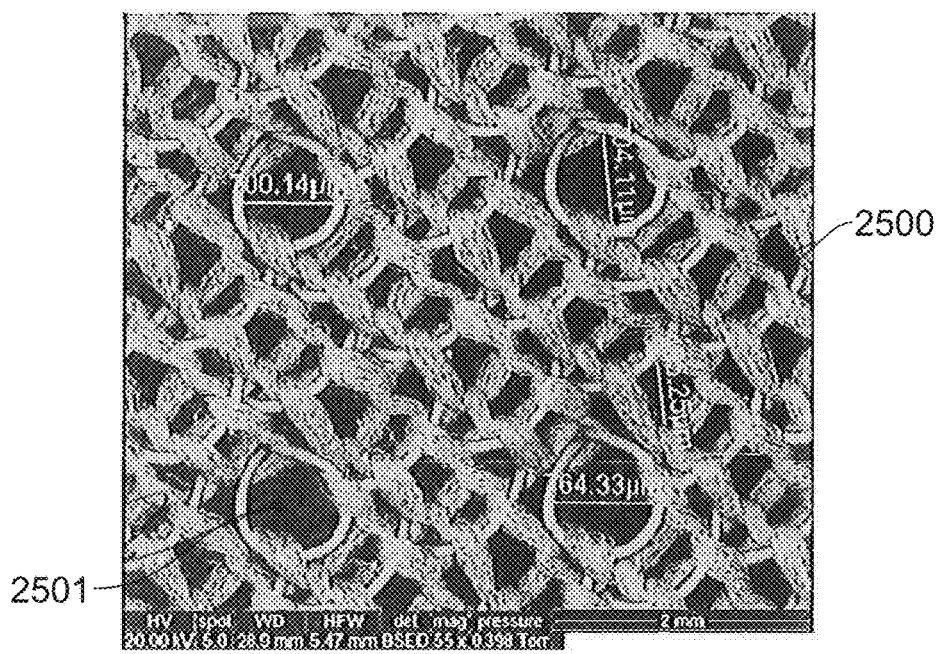
Figure 40:
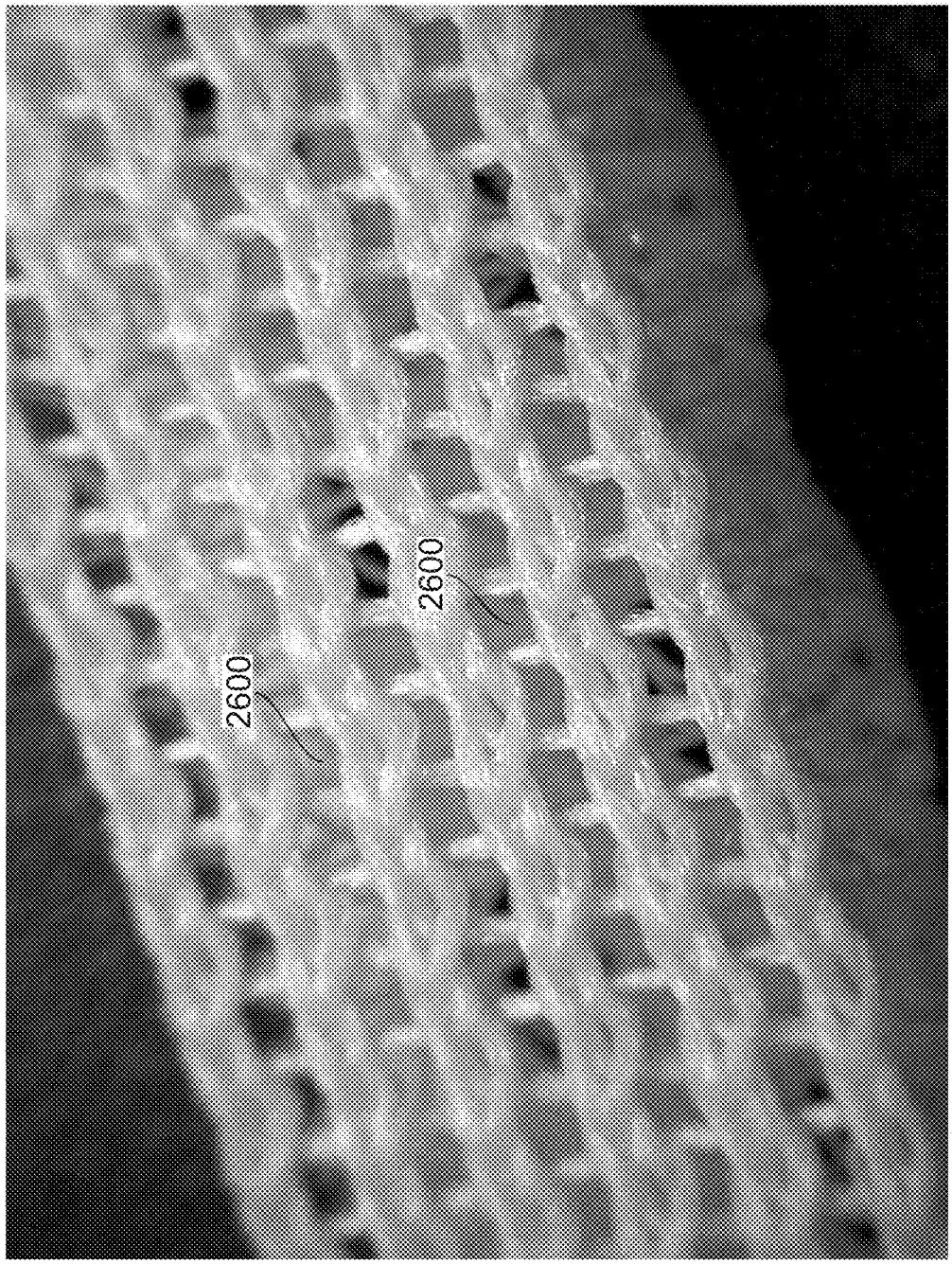
Figure 41:
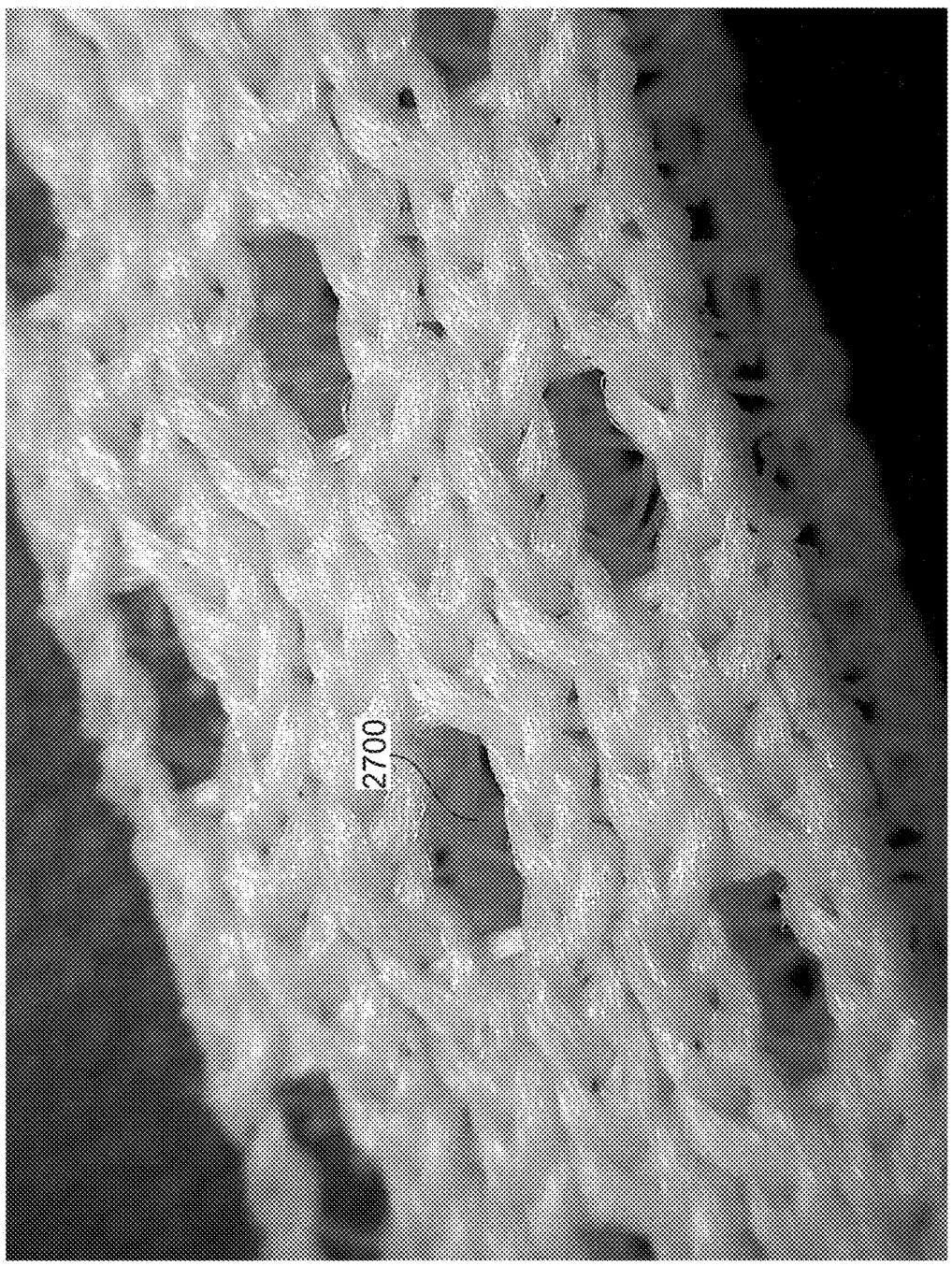
Figure 42:
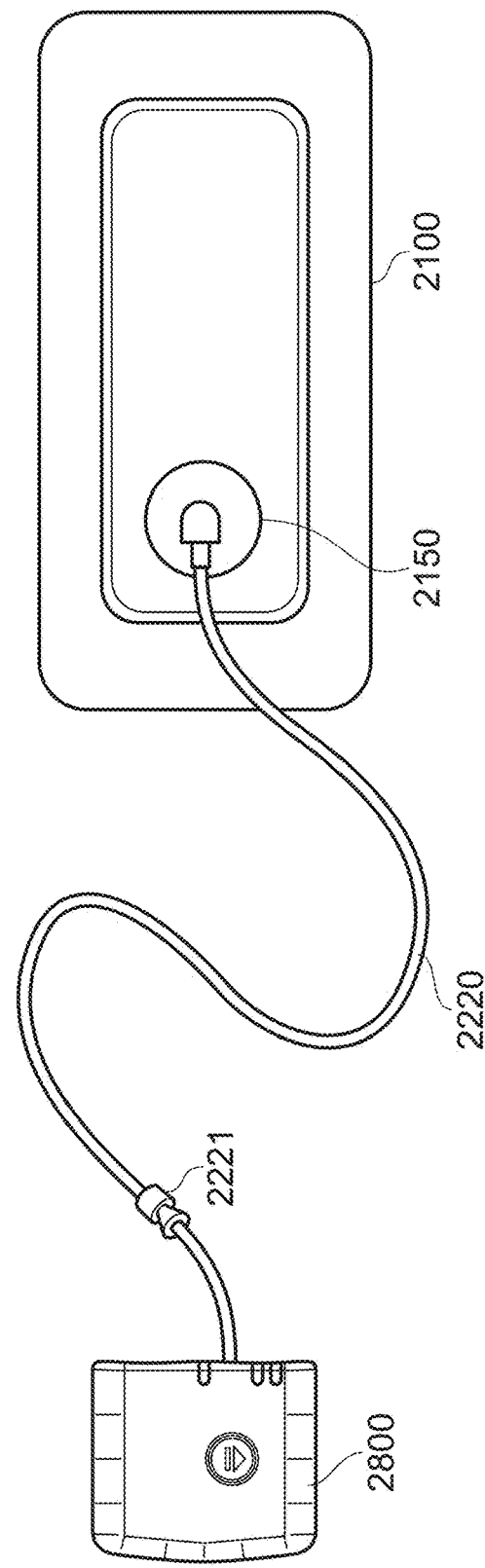

FIGS. 28A-L illustrate a range of exemplifying configurations of baffle elements in a wound dressing, which can be any dressing embodiment disclosed herein;

FIG. 29 illustrates an exemplifying configuration of vias in a transmission layer of a wound dressing, which can be any dressing embodiment disclosed herein;

FIG. 30 illustrates a top view of a wound dressing, which can be any dressing embodiment disclosed herein, including an elongate orifice in a cover layer;

FIG. 31 illustrates a transmission layer in a relaxed mode of operation;

FIG. 32 illustrates a transmission layer in a forced mode of operation;

FIG. 33 illustrates pressure offsetting;

FIG. 34 illustrates a transmission layer and overlying absorbent layer in a relaxed mode of operation;

FIG. 35 illustrates an absorbent layer and transmission layer experiencing a compressive force;

FIG. 36 illustrates an absorbent layer and transmission layer experiencing a shear force;

FIG. 37 illustrates a cross-section of a region of an embodiment of a wound dressing;

FIG. 38 illustrates a lower layer of a transmission layer used in an embodiment of a wound dressing, which can be any dressing embodiment disclosed herein;

FIG. 39 illustrates an upper layer of a transmission layer used in an embodiment of a wound dressing, which can be any dressing embodiment disclosed herein;

FIG. 40 illustrates a lower surface of a transmission layer used in another embodiment of a wound dressing, which can be any dressing embodiment disclosed herein;

FIG. 41 illustrates an upper surface of a transmission layer used in another embodiment of a wound dressing, which can be any dressing embodiment disclosed herein;

FIG. 42 illustrates an embodiment of a wound treatment system; and,

FIGS. 43A-D illustrate the use and application of an embodiment of a wound treatment system onto a patient which can be used with any dressing embodiment disclosed herein.

In the drawings like reference numerals refer to like parts.

Throughout this specification reference is made to a wound. It is to be understood that the term wound is to be broadly construed and encompasses open and closed wounds in which skin is torn, cut or punctured or where trauma causes a contusion. A wound is thus broadly defined as any damaged region of tissue where fluid may or may not be produced. Examples of such wounds include, but are not limited to, incisions, lacerations, abrasions, contusions, burns, diabetic ulcers, pressure ulcers, stoma, surgical wounds, trauma and venous ulcers or the like. The wound dressing may be used for a human or other living being.

In some embodiments, it may be preferable for the wound site to be filled partially or completely with a wound packing material. This wound packing material is optional, but may be desirable in certain wounds, for example deeper wounds. The wound packing material can be used in addition to the wound dressing. The wound packing material generally may comprise a porous and conformable material, for example foam (including reticulated foams), gauze or a hydrofibre ribbon. Preferably, the wound packing material is sized or shaped to fit within the wound site so as to fill any empty spaces. The wound dressing may then be placed over the wound site and wound packing material overlying the wound site. As used herein the term 'exudate' is used to broadly cover any of wound exudate (such as cells, infection by products, cellular debris, proteins, etc.), blood or any other matter released from a wound.

As an overview, the present disclosure relates to an absorbent dressing, where the particular layers provide individual properties to the dressing, and where the combination of these layers in a particular order provides additional properties.

Below are described several properties of such a multi-layered dressing, which can be incorporated independently or in combination with each other.

(a) Dressing pad assembly with layers arranged so that odour control is placed between two layers of different rates of absorptions. This forces the fluid through the odour control layer, but ensures it does not remain saturated with fluid, which enables it to remain efficient.

Odour control can also be achieved by incorporating odour-control materials within some of the other layers of the pad.

Differential absorption also helps to limit the risk of maceration close to the skin, as the foam layer (closest to the wound) is drained of its excess fluid by the superabsorber layer (on the other side of the odour control layer). The superabsorber layer does not allow fluid to be released in liquid form under compression, and fluid can only leave this layer by evaporation, or wicking transfer to a further layer. The superabsorber layer can be shaped to a larger size than the lowest pad layer, to ensure adequate protection against potential leaks by providing a highly absorbent zone at the very edge of the pad. This can also be achieved by including a ring of highly absorbent material superimposed on the pad assembly.

(b) Dressing containing a means of partially obscuring the top surface. The effect is to reduce the visibility of unsightly exudates while allowing clinical judgment on the state of the dressing. This is currently achieved by using a visual masking layer, where overlapping fabrics with openings are disposed slightly offset of each other, for example. While this method allows fluid to wick up through this layer and reach the top film, coloured solids remain onto the layer below, thus containing the coloured solid matter at a little distance from the top film and providing a reduced aesthetics impact.

(c) A dressing design that has enhanced compatibility with body movement by means of:

Using pad components which can deform plastically under the pressures used to apply dressings (unlike purely foam dressings which tend to apply tension forces to resume their as initial flat shape) and retain the shape they have been given around a part of the body Having no, or minimal, means of bonding the layers together, to ensure that the dressing composition does not offer resistance to movement by providing resistance to internal shear A larger border to increase article retention, and the area of elastic stretch that can follow the movement of the skin Shaping the dressing such that sub-areas of the pad can move independently from each other without compromising the overall position or integrity of the dressing Using different dimensions of the pad components to minimise the angle of incidence of the dressing edge, which links to reduced resistance to rubbing onto textile These can be used individually or in combination of any number, however the effect is maximised by using all options in one embodiment.

(d) A dressing pad design that provides enhanced protection against mechanical forces, both from the outside (shocks, knocks, shear) and the inside (pressure onto wounds from bony protrusions).

Protection against the ill effects of direct pressure can be achieved by incorporating, in the structure of the dressing, a means of spreading a point pressure into a proportionally lower pressure across a larger surface area.

In particular, the use of three-dimensional knits, such as spacer fabrics, can provide the desired effect. The vertical filaments bonding two horizontal knitted layers can help to initially resist collapse of the dressing structure, and spreading of the pressure across a wider area than that of the point force applied. The yield point at which the dressing collapses completely can therefore be seen at higher forces than what traditional foam dressings can withstand.

Pressure distribution maps can also show that such a 3-D structure can spread a point force to a wider area than a foam layer of the same thickness can.

Protection against shear can be achieved by ensuring that the components of the dressing can themselves shear compared to each other: this can diminish what shear forces are being transmitted through to the skin or the wound.

(e) A dressing pad assembly where the following properties are being provided by given material layers, and where the respective position of these layers provides additional properties on top of those from the individual layers. The description below describes the pad composition from the side closest to the wound (i) to the side furthest from the wound (v):

i. Initial fluid uptake into the dressing pad, through a wound contact layer, via a soft, hydrophilic polyurethane foam layer (reduced risk of maceration, comfort, maintain moist wound healing environment)

ii. Odour-control of the fluid taken up via a layer of activated charcoal cloth, which performs in a wet state (odour control)

iii. Transfer of fluid through this odour-control layer and onto an absorbent layer, which does not release the fluid back out in liquid form (reduced risk of maceration, maintain moist wound healing environment)

iv. Impact and shear protection through a three-dimensional knitted fabric, which offers resistance to pressure transfer onto the wound (shock and knock protection)

v. Partial masking of the uppermost surface of the pad through a semi-opaque component (enhanced aesthetic appearance during wear, allowing clinical judgement)

Combination of (ii) and (iii) enhances the odour control capability, as this helps to reduce the fluid saturation of the odour control layer and maximise its efficacy.

Combination of (iii), (iv) and (v) to ensure that fluid is being evaporated from the superabsorber layer, out of the dressing through the moisture-vapour permeable top film.

For all the dressing pads described (a) to (e), the pad is contained between a wound contact layer and a top film.

The wound contact layer can comprise a perforated wound-side adhesive which can be a silicone adhesive, or a low-tack adhesive to minimise skin trauma on removal. The wound contact layer comprises a support material which can be a mesh, a net or a perforated film. It can also comprise a construction adhesive on the pad side, to ensure its intimate contact with the lowest part of the pad, and therefore efficient uptake of fluid from the wound without pooling.

The top film is a liquid-impermeable, moisture-vapour permeable, breathable film, which allows moisture to evaporate from the dressing.

Figure 1:
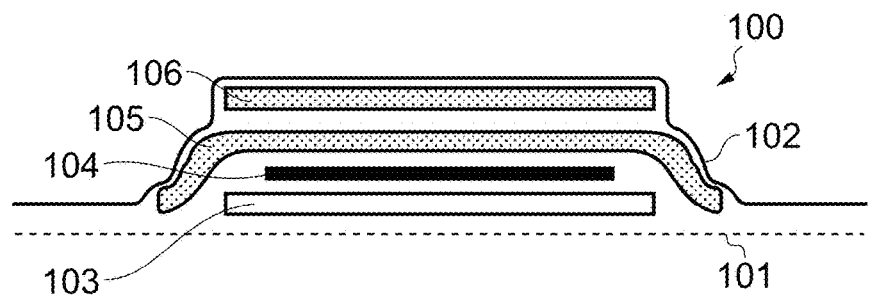
FIG. 1 illustrates a view through an embodiment of a wound dressing of the present disclosure.
Figure 2A:
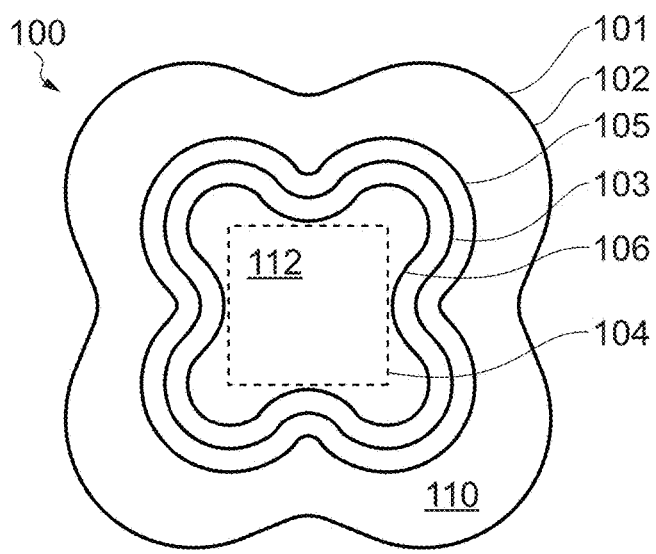
FIG. 2a illustrates a plan view of the dressing of FIG. 1.
Figure 2B:
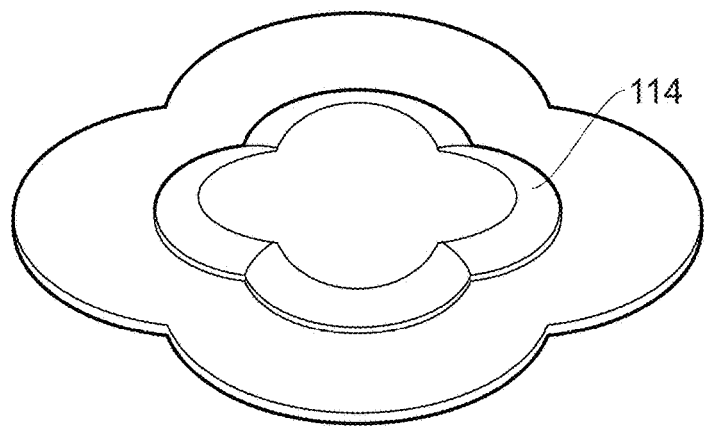
FIG. 2b illustrates a perspective view of the dressing of FIG. 1.

FIGS. 1, 2a and 2b respectively show a schematic cross-sectional view, a plan view and a perspective view of a wound dressing according to an embodiment of the present disclosure. The wound dressing 100 includes a number of layers that are built up in a generally laminar fashion to form a dressing having a relatively planar form. The wound dressing 100 includes a border region 110 extending around the outer periphery of the dressing and a raised central region 112 in the centre of the dressing (in plan view). The precise dimensions of the border region and the central region may be predetermined to suit a particular wound or particular wound type. There may be no border region required. Here the border region has the general function of providing an area for sealingly engaging with a patient's skin surrounding a wound site to form a sealed cavity over the wound site. The central region is the location of further functional elements of the wound dressing.

The dressing 100 includes a perforated wound contact layer (101) and a top film (102).

Further components of the wound dressing 100 include:

A layer of polyurethane hydrocellular foam (103) of a suitable size to cover the recommended dimension of wounds corresponding to the particular dressing size chosen A layer of activated charcoal cloth (104) of similar or slightly smaller dimensions than (103), to allow for odour control with limited aesthetic impact on the wound side.

A layer of superabsorbent air-laid material (105) containing cellulose fibres and a superabsorbent polyacrylate particulates, of dimensions slightly larger than (103) to allow for an overlap of superabsorbent material acting as leak prevention A layer of three-dimensional knitted spacer fabric (106), providing protection from pressure, while allowing partial masking of the top surface of the superabsorber, where coloured exudate would remain. In this embodiment this is of smaller dimension (in plan view) than the layer (105), to allow for visibility of the edge of the absorbent layer, which can be used by clinicians to assess whether the dressing needs to be changed.

In this embodiment the wound contact layer 101 is a perforated polyurethane film that is coated with a skin-compatible adhesive, such as pressure sensitive acrylic adhesive or silicone adhesive (not shown). Alternatively the wound contact layer may be formed from any suitable polymer, e.g. silicone, ethylvinyl acetate, polyethylene, polypropylene, or polyester, or a combination thereof. The skin-compatible adhesive is coated on the lower side of the layer 101, i.e. the side that is to contact the patient. Aptly the adhesive is coated as a continuous layer on the underside of the layer 101. Optionally the adhesive may be coated in a semi-continuous layer such as in a pattern such as a chequerboard pattern, polka dot pattern, herring bone pattern, mesh pattern or other suitable pattern. Alternatively the adhesive may be coated around a border region 110 of the dressing only, and not in a central region 112 of the dressing (as viewed from above in plan view) such that the adhesive may adhere to skin surrounding a wound and not the wound itself. The perforations allow the wound contact layer to be permeable to liquid and gas. The perforations are through holes extending from an upper surface to a lower surface of the wound contact layer to enable fluid to flow through the layer. The perforations are small enough to help prevent tissue ingrowth into the wound dressing yet still allow fluid to flow. The perforations may be slits or holes having a size range of 0.025 mm to 1.2 mm for example. The upper surface of layer 101 may optionally be coated with adhesive, to help in the construction of the dressing. Aptly the adhesive may be a pressure sensitive adhesive and aptly the same adhesive as used on the lower surface of the layer 101.

The absorbent layer 103 of polyurethane hydrocellular foam is located over the wound contact layer 101 and extends over the central region 112 of the wound contact layer.

The term hydrocellular is a term given to foams that are absorbent, hydrophilic and polymeric. The foams may have a particular range of cell size of 30 microns to 700 microns.

The foam is in this case of polyurethane, hydrophilic, conformable, resilient, and porous and allows fluids such as wound exudate to be drawn away from the wound site and further into the dressing. However, the foam also maintains a sufficiently moist wound healing environment so as to not dry out the wound, retaining a balanced moist atmosphere under the dressing. An optimal wound healing environment generally requires the area of the wound to have some level of moisture yet without excessive fluid.

The absorbent employed in the absorbent layer of the dressings may be any suitable polymer foam. The foam is aptly a highly conformable hydrophilic foam, aptly an open celled foam, and more aptly the foam is a mixture of open and closed cells.

The absorbent layer used in dressings of the present disclosure is capable of absorbing wound exudate. It is desirable that the foam layer absorbs the wound exudate rapidly. Such rapid absorption prevents undesirable pooling of exudate between the dressing and the wound.

The ability of polymer foam layers to absorb and retain fluids depends to some extent on the size of the foam cells, the porosity of the foam and the thickness of the foam layer. Suitable open cell foams of dressing embodiments of the present disclosure have a cell size of 30 microns to 700 microns and aptly a cell size of 50 microns to 500 microns. Apt open cell hydrophilic foams of dressings of the present disclosure have 20% to 70% and preferably 30% to 60% of the total membrane area of the cells as membrane openings. Such open cell foams permit transport of fluid and cellular debris into and within the foam.

Apt foams may be polyurethane, carboxylated butadiene styrene rubber, polyacrylate or the like foam. Such foams may be made of hydrophilic materials per se or may be treated to render them hydrophilic, for example with surfactants. It is preferred to use foams that are made of polymer that is itself hydrophilic as it has been found the exudate is less likely to coagulate rapidly. Favoured hydrophilic polymer foams are hydrophilic polyurethane and especially those which are made of crosslinked hydrophilic polyurethane. Preferred foams can be made by reacting a hydrophilic isocyanate terminated polyether prepolymer with water. Suitable hydrophilic polyurethane foams of this type include those known as Hypol™ foams. Hypol™ foams can be made from Hypol hydrophilic prepolymers marketed by W. R. Grace and Co and are hydrophilic cellular foams having a mixture of open and closed cells. Hypol™ based foams are also available from Dow Chemicals. Other suitable foams are described in WO91/01706 in relation to the absorbent layer described, incorporated herein by reference, and in WO93/04101 also incorporated herein by reference.

The use of such foams of hydrophilic polymer in the absorbent pad of dressings of the present disclosure can allow the wound to be maintained in a moist condition even when the exudate produced has been absorbed and removed from the wound surface.

A further function of the foam layer is to wick away excess fluid from the wound area via its open cells. It is noted that PU foam itself can absorb liquid, the whole polymer swelling.

The odour-removing layer of activated charcoal cloth 104 is provided over the layer of foam 103. In this embodiment the activated charcoal layer is about the same length and depth as the foam layer and therefore lies over the foam layer to cover about the same area. The layer may be of Zorflex® cloth available from Chemviron Carbon, for example. Alternative suitable materials are manufactured by MAST under the trade name C-TeX®.

The function of the odour-removing layer is to help prevent or reduce odour originating from the wound from transmitting out of the dressing.

It is noted that in this example the odour-removing layer is provided as a loose layer, unbonded to the adjacent layers, though alternatively the layers may be bonded by adhesive or stitching, etc.

The layer of absorbent material 105 is provided over the odour-removing layer 104. The absorbent layer 105 extends fully over the layer 104, as well as over the side portions of both the odour-removing layer 104 and foam layer 103. The absorbent material may be a foam, woven or non-woven or knitted natural or synthetic material and may optionally include or be super-absorbent material. A suitable material may be an air-laid material containing cellulose fibres and superabsorbent polyacrylate particulates or fibres, for example superabsorber cores available from Novathin. Alternatively the absorbent layer 105 may be manufactured from ALLEVYN™ foam, Freudenberg 114-224-4, ChemPosite™ 11C-450, CMC (e.g. Medline Maxsorb with Alginate), alginate (e.g. ActivHeal Alginate by Advanced Medical Solutions) and/or polyacrylate fibres (e.g. SAF™ by Technical Absorbent Ltd).

The layer 105 forms a reservoir for fluid, particularly liquid, removed from the wound site and draws those fluids towards a cover layer 102. The material of the absorbent layer also prevents liquid collected in the wound dressing from flowing freely once in the dressing structure. The absorbent layer 105 also helps distribute fluid throughout the layer via a wicking action so that fluid is drawn from the wound site and stored throughout the absorbent layer, i.e. transferring and locking in the liquid. This prevents agglomeration in areas of the absorbent layer. The capacity of the absorbent material should be sufficient to manage the exudate flow rate of a wound for the predetermined life of the dressing, whether the wound is acute or chronic. Again, in combination with the foam layer, the layer 105 aptly should not cause the wound to become completely dry. This might occur if, for example, the superabsorbent material were to dry out the foam layer and then subsequently the wound area.

Aptly, the absorbent layer is a layer of non-woven cellulose fibres having super-absorbent material in the form of dry particles dispersed throughout. Use of the cellulose fibres introduces fast wicking elements which help quickly and evenly distribute liquid taken up by the dressing. The juxtaposition of multiple strand-like fibres leads to strong capillary action in the fibrous pad which helps distribute liquid. In this way, the super-absorbent material is efficiently supplied with liquid. Also, all regions of the absorbent layer are provided with liquid.

The absorbent layer 105 aptly has a high osmotic potential so as to prevent liquid being released from the layer, even when the layer is under compression (e.g. if the dressing area is pressed or leant on). Liquid may however leave the layer by diffusion through evaporation or possibly wicking transfer to a further layer.

The layer of absorbent material 105 may be of any suitable dimensions. Aptly, if the layer is shaped to a size larger than the layers between itself and the wound contact layer, then the layer can fold over the edges of any intermediate layers, acting as an enclosure such that any fluid moving into the dressing will encounter the absorbent layer prior to encountering the top film or the adhesive wound contact layer. This helps to prevent possible leaks of fluid from the dressing. As an alternative, a ring shaped (annular or torus) or other suitable border shaped portion of absorbent material may be added to a dressing separately from the absorbent layer to surround underlying layers and to perform the same function as the overlying edge of the absorbent layer.

Optionally, according to certain embodiments of the present disclosure, the absorbent layer may include synthetic staple fibres and/or bi-component staple fibres and/or natural staple fibres and/or super-absorbent fibres. Fibres in the absorbent layer may be secured together by latex bonding or thermal bonding or hydrogen bonding or a combination of any bonding technique or other securing mechanism. Aptly, the absorbent layer is formed by fibres which operate to lock super-absorbent particles within the absorbent layer. This helps ensure that super-absorbent particles do not move external to the absorbent layer and towards an underlying wound bed.

Aptly, the fibres are strand-like and made from cellulose, polyester, viscose or the like. Aptly, dry absorbent particles are distributed throughout the absorbent layer ready for use. Aptly, the absorbent layer comprises a pad of cellulose fibres and a plurality of super absorbent particles. Aptly, the absorbent layer is a non-woven layer of randomly orientated cellulose fibres.

Super-absorber particles/fibres may be, for example, sodium polyacrylate or carbomethoxycellulose materials or the like or any material capable of absorbing many times its own weight in liquid. Aptly, the material can absorb more than five times its own weight of 0.9% W/W saline, etc. Aptly, the material can absorb more than 15 times its own weight of 0.9% W/W saline, etc. Aptly, the material is capable of absorbing more than 20 times its own weight of 0.9% W/W saline, etc. Aptly, the material is capable of absorbing more than 30 times its own weight of 0.9% W/W saline, etc.

Aptly, the particles of superabsorber are very hydrophilic and grab the fluid as it enters the layer, swelling up on contact. An equilibrium is set up within the dressing core whereby moisture passes from the superabsorber to the top film and the fluid vapour starts to be transpired. A moisture gradient may be established within the dressing to continually remove fluid from the wound bed.

The shielding layer 106 is a layer having a 3-dimensional structure that may include open cell foam (e.g. Alleyvn™ foam by Smith & Nephew, Biatain foam by Coloplast or Advanced Medical Devices' ActivHeal foam), a knitted or woven spacer fabric (for example Baltex 7970 weft knitted polyester or Baltex XD spacer fabric or Surgical Mesh's Polyester felt or Polyester mesh) or a non-woven fabric (e.g. Fiberweb's S-tex or Securon). Alternatively the shielding layer may be a completely opaque polymer film having cut-out windows or perforations, for example (e.g. SNEF's H514 or H518 blue net). Here the layer 106 is of polyester that includes a top layer (that is, a layer distal from the wound in use), which is a 84/144 textured polyester, a bottom layer (that is, a layer that lies proximate to the wound in use), which is a 100 denier flat polyester and a third layer formed sandwiched between these two layers, which is a region defined by a knitted polyester viscose, cellulose or the like monofilament fibre. Of course other materials and other linear mass densities of fibre could be used, including for example a multistrand alternative. The shielding layer 106 may be similar or identical to the materials described in US2011/0282309 in relation to the transmission layer (FIGS. 23 to 27).

The layer 106 allows the transmission therethrough of any gas or vapour to the top film 102 and may therefore be considered as a transmission layer.

Aptly the layer 106 performs one or more further functions including acting as a partial masking layer and acting as a force distributing (impact protection) layer.

Figure 11A:
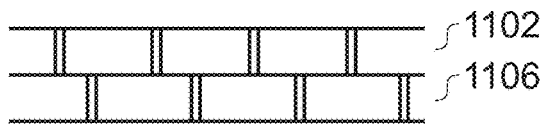
FIG. 11 illustrates various obscuring elements.
Figure 11B:
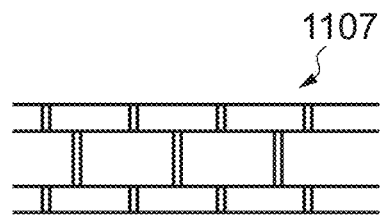

Partial masking of wound exudate, blood or other matter released from a wound may be achieved with overlapping perforated fabrics disposed somewhat offset from each other, such as shown in FIG. 11(*b*). As shown in (*b*), a shielding layer is itself formed from 3 sub-layers, such as the 3-D knit material described above. The perforated top and bottom layers allow transport of vapour and gas, and are offset from gas pathways in the central knitted layer. As such, vapour and gas may travel through the layer, but the coloured exudate cannot be seen, or travel, through the layer.

Alternatively, as shown in FIG. 11(*a*), a perforated cover layer 1102 is provided over a perforated shielding layer 1106, which allows moisture vapour and gas to be transmitted away from the dressing, yet provides sufficient masking for exudates to be visible only to a trained clinician.

More specifically, it is known that when a film is breathable (able to transmit vapour), then it is likely to allow colour to transmit therethrough. Even if a breathable film includes a coloured pigment for masking a lower layer, when exudate fluid contacts the film, coloured elements in the exudate can be carried into contact with the film and change the colour perception from the film, and be visible to the user. This allows fluid to transmit through the layer towards the top film whilst coloured solids or liquids remain bound in the absorbent layer below. Exudate colour is principally due to proteins and biological break down products from tissue or blood cells, which tend to be large molecules.

Another function of the shielding layer 106 may be for pressure distribution and impact protection. For example, if the patient accidentally knocks the wound area, leans on the wound area or another cause applies a pressure to the dressing covering a wound. Aptly the shielding layer is provided closer to where the pressure is being applied than other layers of the dressing.

The shielding layer 106 acts as a pressure spreading component, receiving a pressure on one side thereof (possibly a point force) and spreading the pressure over a wider area, thus reducing the relative pressure received on the other side of the shielding layer. As such, the level of pressure felt by the patient at the wound site is reduced.

A form of shielding layer that has been found to be a good pressure distributed is a layer having non-ordered fibres or strands, i.e. fibres lying at different angles with respect to each other, for example the knitted spacer fabric of Baltex 7970.

The absorbent layer 105 may also act as a pressure spreading component. A combination of the shielding layer 106 and the absorbent layer 105 has been found to give particularly apt pressure distributing properties. However, only one pressure spreading component may be sufficient.

In general, a material that is relatively non-deformable is more suitable for spreading point pressure. However this should be balanced by the requirement for deformation ability for the dressing to adhere to a non-planar body part.

When a pressure occurs from inside the patient's body, such as pressure from a protruding bone, the shielding layer may be somewhat less efficient at spreading the pressure if it is positioned towards the distal part of the dressing. However, any equal and opposite reaction of force acting back toward the patient's skin will be spread by the shielding layer 106 and absorbent layer 105 (e.g. if the patient is laying on something hard such as the ground or hard chair). The pressure spreading response will depend somewhat upon the hardness of the surface against which the patient and dressing are pressed against, if any.

The pressure spreading ability of these layers may also be useful against slower, constant pressures as well as rapid point forces.

The top film 102 is a cover layer for covering the lower layers of the dressing, helping to encapsulate the layers between the wound contact layer and the top film. The top film 102 is in this case a layer of polyurethane, Elastollan (trade name) SP9109 manufactured by BASF. The top film may be coated with any suitable adhesive. Aptly the adhesive will be a pressure sensitive adhesive e.g. acrylic adhesive or silicone adhesive.

As such, the top film 102 helps to ensure that the dressing remains breathable, i.e. allows a proportion of fluid absorbed in the dressing to be evaporated via the outer surface of the dressing. In this way certain fluid content of the exudate can be transpired from the dressing, reducing the volume of remaining exudate and increasing the time before the dressing becomes full. Also, the wound contact layer 101 and top cover 102 help to ensure that the border region 110 of the dressing remains breathable, i.e. allows a patient's normal skin perspiration to be evaporated through the dressing, which helps in preventing or minimising skin maceration.

The outer layer of dressings of the present disclosure when present can be a continuous conformable film. The continuous moisture vapour transmitting conformable film outer layer of the wound dressing may be used to regulate the moisture loss from the wound area under the dressing and also to act as a barrier to bacteria so that bacteria on the outside surface of the dressing cannot penetrate to the wound area. Suitable continuous conformable films will have a moisture vapour transmission rate of at least 300, aptly from 300 to 5000 grams preferably 500 to 2000 grams/square meter/24 hrs at 37.5 C at 100% to 10% relative humidity difference. Such moisture vapour transmission rate of the continuous film allows the wound under the dressing to heal under moist conditions without causing the skin surrounding the wound to macerate. To ensure the use of an adhesive on the top film 102 does not reduce the moisture vapour transmission rate, a hydrophilic water dispersible adhesive may be used e.g. hydrophilic acrylic adhesives. Although, other suitable adhesive may also be used. Aptly adhesive may also be spread across the surface of the film in the form of a pattern such that a portion of the area of the film does not contain adhesive. E.g., use of a polka dot pattern whereby adhesive is not present in the dot area and 5 to 95%, or aptly 10 to 80%, more aptly 30 to 70%, more aptly 40 to 70%, more aptly 40 to 60%, more aptly 40 to 50% of the area of film does not contain adhesive. It will be apparent to those skilled in the art that any suitable pattern of adhesive layer may be used to produce a top film 102 that is not fully coated with adhesive and thus maximises the moisture vapour transmission rate. Other suitable materials for the cover layer are described in WO91/01706 in relation to the conformable moisture vapour transmitting outer layer.

Additionally, the top film may act as a further barrier to any remaining odour from being transmitted out of the wound dressing, since the top film may include through holes that allow molecules of a predetermined maximum size to pass therethrough.

FIGS. 2a and 2b show a possible shape of a dressing, useful for enhanced compatibility with body movement, where each layer is shaped to reduce the incident angle of the pad edge, and to provide somewhat independently moving sub-sections of the dressing. The dressing border, including the wound contact layer (101) and the top film (102) can also comprise slits, provided to further enhance the conformability on application by allowing the borders to overlap if needed.

Reverting back to FIG. 1, it can be seen that the cross-section of the dressing includes various layers stacked in a contiguous manner so as to form a generally laminate structure. Preferably the dressing is moisture vapour permeable. The layers shown in FIG. 1 are of different widths and dimensions, though other arrangements are also possible.

In the border region 110, the top film 102 abuts with the wound contact layer 101. A moisture vapour transmitting adhesive layer is provided (not shown) in the border region 110 between the layers 101, 102 to bond the layers in that region. Suitable adhesives that are moisture vapour transmitting include various acrylate ester copolymer and polyvinyl ether pressure sensitive adhesives for example as described in UK patent number 1280631. Aptly the adhesives may be copolymers of an acrylate ester with acrylic acid for example as described in UK patent application number 2070631.

The dimensions of the components are arranged so as to minimise the angle of incidence of the dressing edge. This helps to reduce rubbing of the dressing against textiles and reduced snagging of the dressing against textile, by reducing the change in profile of the dressing throughout the thickness of the dressing.

In use, a wound dressing as described above would be applied to a wound site of a patient with the surface of the wound contact layer 101 facing the wound site. Any wound exudate, blood or other wound fluid would travel into the dressing via the wound contact layer and sequential layers above the wound contact layer. Fluid would permeate through the foam layer, the activated charcoal layer, and then reach the absorber layer at which point preferably the liquid would not go any further and be retained by the absorber layer. On the other hand, gas and moisture vapour would be able to permeate further via the shielding layer and/or top film.

FIG. 3 shows the difference between the appearance of existing dressings and of a dressing of the present disclosure after use on a wound model. The photographs (a) and (b) are known dressings. The photograph (c) is a wound dressing according to the present disclosure. The region identified by reference number 114 is the area of the central region 112 that is not covered by the shielding layer 106. As such, the absorbent layer 105 is directly adjacent the top film 102 in this area. Since the shielding layer 106 acts as a partial masking layer, the region 114 may be used by a clinician or other trained user to assess the spread of wound exudate throughout the dressing. This assessment will be helped by the dressing being placed approximately central over a wound such that exudate reaches the radially outer region 114 after the exudate has reached the more central areas (e.g. that covered by the shielding layer 106). Aptly, the clinician may be trained to assess the spread of wound exudate using the region 114 as a guide, for example with instructions that less than 50% coverage of the region 114 with exudate does not require changing of the dressing, about 50% coverage of the region 114 indicating the time to consider changing the dressing, and more than 50% coverage of the region 114 with exudate does require changing of the dressing. Of course the area of the central region 112 covered with the shielding layer 106, which acts as a partial masking layer, may also or alternatively be used to assess the spread of exudate by a trained clinician. In addition, the dressing may have various other instructions for use, for example including a recommended maximum duration that the dressing may be used, e.g. 7 days, regardless of the assessment of the spread of exudate.

FIG. 4 shows the odour control performance of the present disclosure (Design A) when wet, compared to existing dressings. This was measured by incubating dressing samples with solutions of odorous compounds in vials, for 24 h at 37° C. The headspace of the vials was subsequently measured by gas-chromatography headspace, for the concentration of odorous compounds remaining in the headspace. The efficiency in odour reduction was measured as a percentage remaining compound, compared to a positive control of incubated odorous compound only. Performance across four different compounds was collated in a single measure, represented in FIG. 4. It can be seen that a dressing according to the present disclosure (with the arrangement of FIG. 1) performs very well in removing odour, with less than 5% odour remaining in the headspace. By comparison, foam dressings perform relatively poorer with higher amounts of odour remaining.

FIG. 5 shows the comparative performance of different shapes of dressings when placed on a tube. It can be seen that a dressing according to the disclosure (with the arrangement of FIG. 1), as shown on the right hand side, remains adhered to the tube after 2.5 hours, whilst a conventional dressing as shown in the left hand side lifts away from the tube after the same 2.5 hours.

The wound dressing of the disclosure may be of any suitable shape or form or size. The overall dimensions of the dressing may be, for example, 160 mm diameter, although any total size may be used, and the size may be determined to match particular wound sizes.

In addition, it is noted that the dressing's improved conformability with non-planar (bodily) shapes can be achieved in part by combining a foam with a material that could be only returned to its initial shape by a force higher than that applied onto it by foam. The role of this second material is to remain in the shape it was given at the application of the dressing, despite the forces applied to it by the foam material trying to relax after deformation at application. E.g. airlaid or non woven material with broken or displaced fibres by the initial application force could provide sufficient resistance against pressure of a hydrocellular foam layer (2 to 4 mm).

The inventors have realised that a dressing formed from foam only will tend to revert to its natural position (planar or flat in the case of the foam layers described here). The foam has a 'memory' of how it was cut and manufactured. Thus when foam dressings are applied with adhesive onto non-flat body parts the adhesive must be sufficiently strong to oppose the force of the foam reverting to its original shape.

Figure 6:
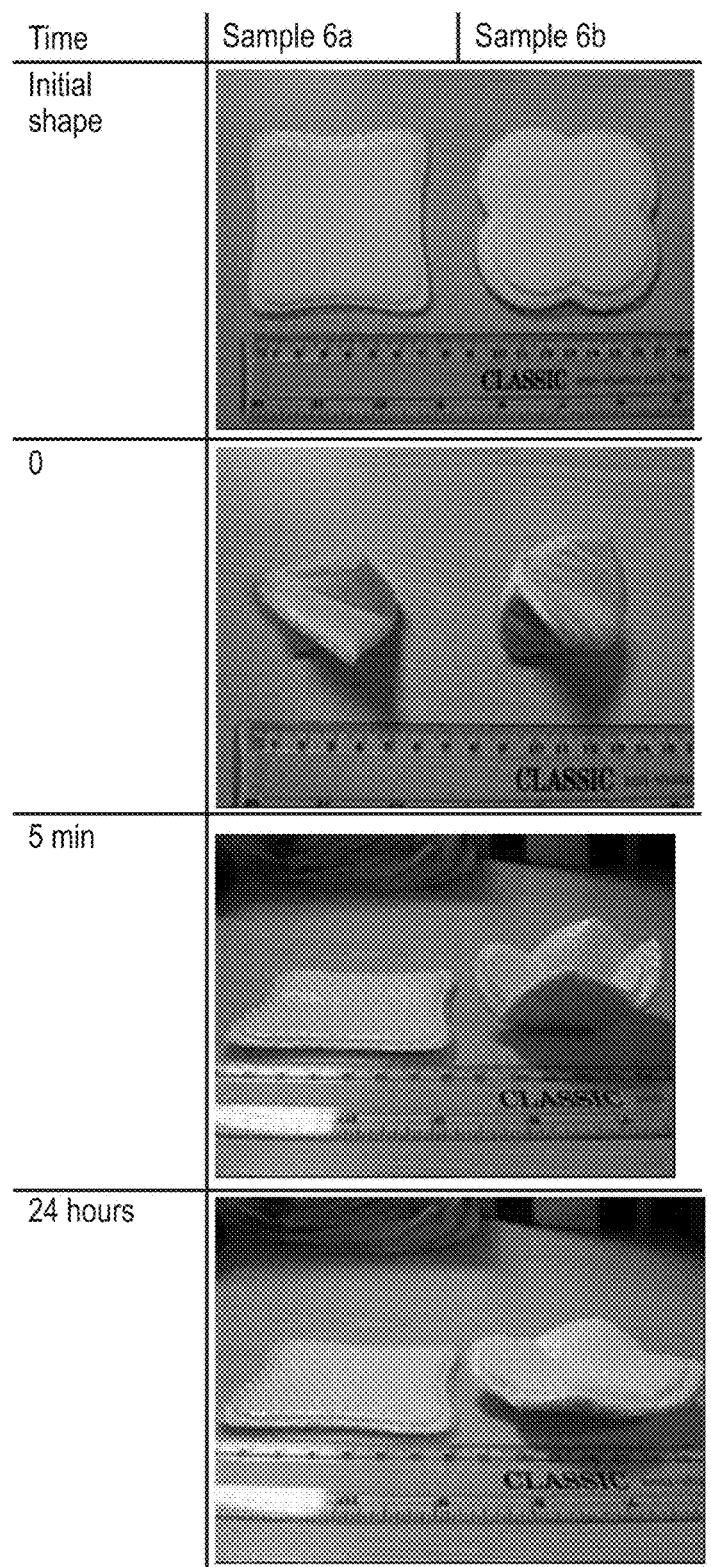
FIG. 6 shows photographs of a prior art dressing and an embodiment of a dressing of the present disclosure over time.

As shown in FIG. 6, the performance of a dressing in terms of retention of formed shape including a foam layer and a deformable layer, e.g. a layer similar to the absorbent layer 105 (Sample 6b), has been shown to be much improved compared to a dressing that is formed from a foam only (Sample 6a).

That is, sample 6a included a wound contact layer having an adhesive on its 'wound facing' side, a foam layer (such as layer 103) and a cover layer (such as top film 102). Sample 6b included a wound contact layer having an adhesive on its 'wound facing' side, a foam layer (such as layer 103), an absorbent layer (such as layer 105), a shielding layer (such as layer 106) and a cover layer (such as top film 102).

The initial shapes of the two samples shown in FIG. 6 are planar. Upon compressing the samples into a tightly deformed shape (as shown at time 0), the shape of the samples was monitored over time to view any reactive movement by the sample overcoming the force of the adhesive on the wound contact side. After 5 minutes the Sample 6a had returned to its initial planar shape. Sample 6b reverted somewhat back towards its initial shape after 5 minutes, approximately 50% between its initial deformation shape and the planar form. After 24 hours Sample 6b remained non-planar.

It is believed that components of the dressing of the disclosure, such as the absorbent layer or shielding layer, can plastically deform without memory, by components within the layers being displaced or broken to some degree. For example, some of the fibres in the shielding layer may be broken (without overall damage to the dressing). This displacement or breakage is long term or permanent. As such the force of the foam layer of the dressing reverting to its original shape is counteracted by the displaced or broken components within other layers. As such, as long as the force of the foam layer is lower than the force of returning the other layers to a planar position, the dressing will retain its formed (non-planar) shape.

Figure 7:
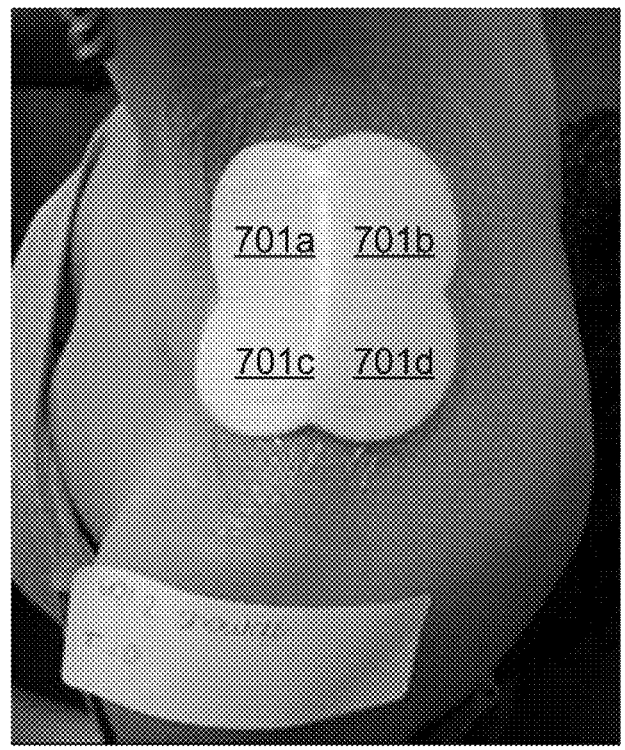
FIG. 7 shows a photograph of an embodiment of a dressing of the present disclosure applied to a patient.

FIG. 7 shows an example of a dressing applied to a human patient, with sub-areas $701_{a-d}$ applied at different angles relative to each other, and that can move independently of each other. As shown the dressing has been applied to the base of the neck and shoulder region of a patient. This region requires the lobes or subareas to be applied at different angles to each other. It is noted that there is no specific dividing line (such as perforation or other fold line) between the sub areas here.

It can be seen that not only the conformability of the materials of the dressing, but also the discrete sub-areas of the dressing help to keep the dressing adhered to the uneven surface of the patient.

Figure 8:
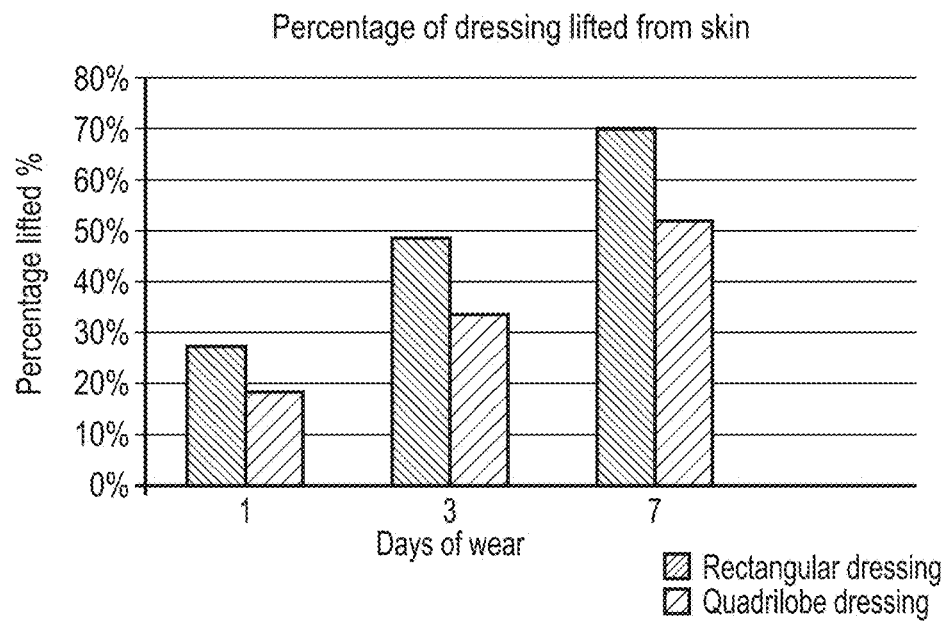
FIG. 8 illustrates a graph of the results of tests monitoring lifting of dressings over time.

FIG. 8 illustrates the testing of a wound dressing having sub areas compared to a comparative known dressing with square profile. The lift of the dressing, i.e. movement returning back to the original flat, planar shape, was monitored over 7 days on 25 healthy volunteers. That is, 25 volunteers wore one wound dressing according to the disclosure and one rectangular dressing. The dressings were applied to the thighs of each volunteer. For each volunteer, after 1, 3 and 7 days of wearing the dressing, the presence of any lifting of dressing border that had detached away from the skin of the volunteer was determined. The graph indicates the percentage of the number of dressings in total that showed any lifting.

As shown in FIG. 8, it can be seen that the dressing having a shape with four lobes or subareas (as per FIGS. 2a and 2b) performed better than the square shaped dressing. The percentage of the dressings with sub areas that showed any sign of lifting away from the volunteer's skin was on average just over 50% of the dressings after 7 days wear. For the square dressing, the percentage of the dressings showing signed of lifting away from the volunteer's skin was on average 70% of the total after 7 days wear.

The dressing shape has a rotational symmetry about its centre point (in plan view). In this example the dressing has 4 lobes. The shape of the central region 112 matches the shape of the border region 110 such that the width of the border region is approximately equal around the entire dressing. Aptly the border may be between about 12.5 mm and about 29 mm. More aptly the border is about 25 mm. Of course the border size will depend on the full dimensions of the dressing. Other numbers of lobes may be used such as 3, 5, 6, 7, 8, etc. The isotropic nature of the dressing shape gives the advantage that the user is not required to orientate the dressing in a specific manner before applying the dressing to a wound. The shape also enables the dressing to be adaptable to various parts of the body.

The dressing shape with 4 sub areas (lobes) aptly gives a maximum pad area with respect to the border area, yet has increased flexibility compared to a square dressing.

Figure 9:
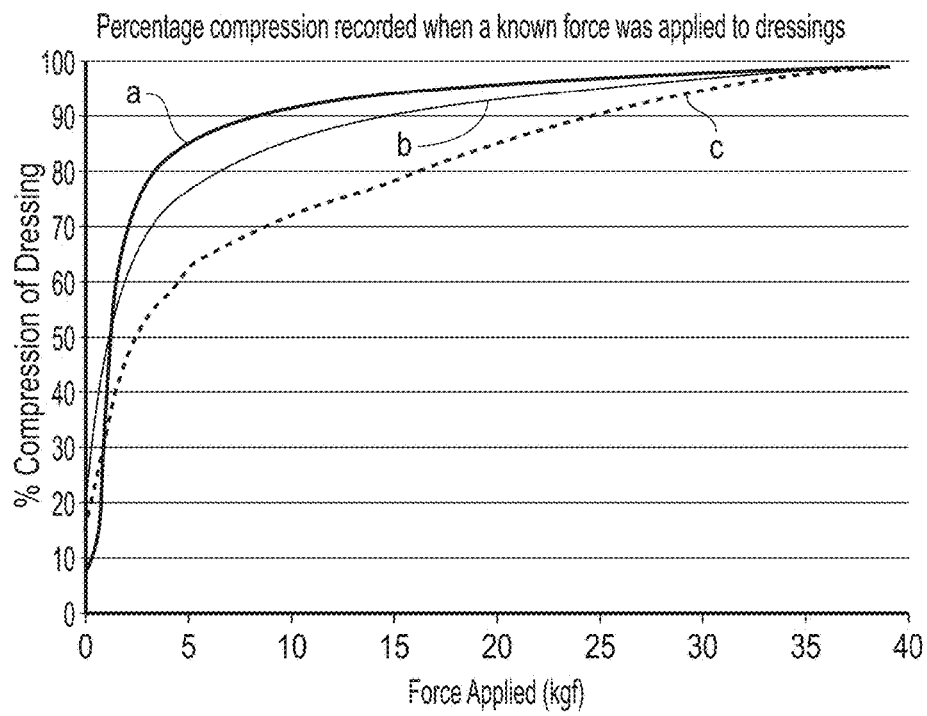
FIG. 9 illustrates a graph of the percentage of compression of various dressings after a known force was applied to each dressing.

The inventors also performed tests upon various dressings with respect to the dissipation of force applied to the dressing. FIG. 9 illustrates the degree of (percentage of) compression of a dressing with different force applied. It can be seen that for almost all forces applied (apart from the extreme ends of the scale at 0 to 3 kgf (kilogram-force) and 40 kgf and over where readings show no appreciable difference), dressing compression is higher for a dressing formed from foam only having a thickness of 4 mm, such as the foam materials described for layer 103 (curve a) than for a dressing including a foam layer of thickness 2 mm and a fibrous non-woven material, such as the materials described for layer 105 (curve b) and a dressing including a foam layer of thickness 2 mm and a fibrous non-woven material, such as the materials described for layer 105, and a layer of 3-D knit material such as the materials described for layer 106 (curve c). As can be seen from the graph in FIG. 9, dressing including a layer of 3-D knit material (curve c) gave the lowest percentage compression of dressing over the range of forces applied between 3 kg and 40 kg.

From this it can be concluded that fibrous non-woven materials and 3-D knit materials will help to act against a force applied by dissipating the force and preventing compression of the dressing.

Figure 10:
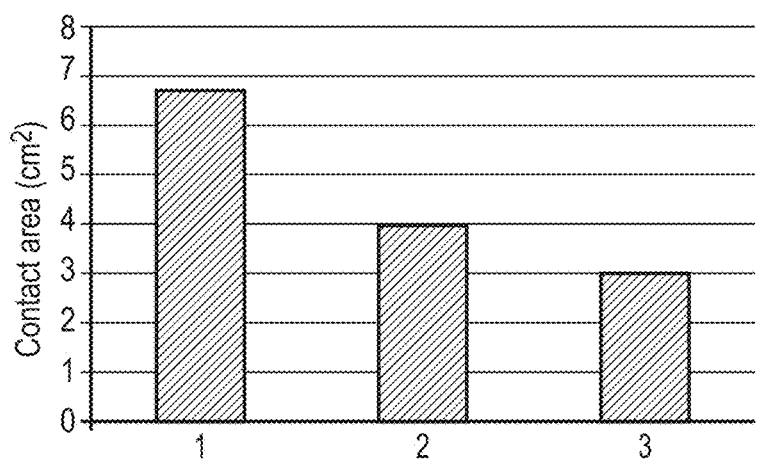
FIG. 10 illustrates the contact area where force is applied after a point pressure is applied to various dressings.

FIG. 10 illustrates the area over which pressure is transferred by different dressings when pressure is applied to the dressing from the point pressure of a 0.8 cm² probe. The area of pressure transferred was measured using a pressure reading mat. This equipment was obtained from Tekscan, and includes an array of thin pressure sensors placed between two relatively thin sheets of plastic. The resulting mat is conformable, and transmits pressure readings from the array through a piece of hardware (I-scan handle), to a computer equipped with the I-scan software. The resulting measurements can be expressed for example as contour maps, value tables, maximum pressure reading for a particular area of the mat, average pressure read over the whole testing area, or contact area over which a pressure was sensed by the mat. Pressure transfer was measured on a dressing including a layer of 3-D knit material (identical to the dressing used giving curve c in FIG. 9) (column 1), a dressing made of non-woven material (identical to the dressing used giving curve b in FIG. 9) (column 2) and a foam dressing (identical to the dressing used giving curve a in FIG. 9) (column 3).

Figure 13:
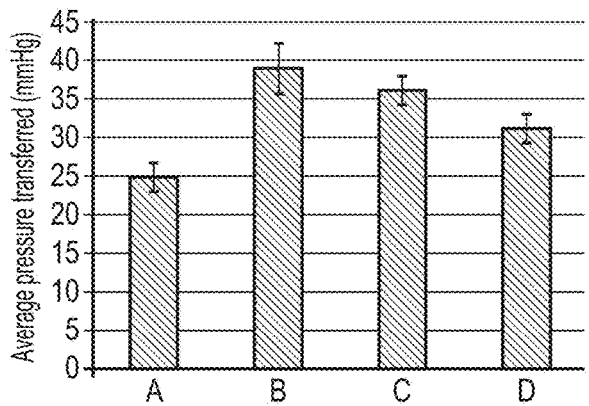
FIG. 13 illustrates a graph of pressure transfer through various dressings.

FIG. 13 illustrates tests performed by the inventors on four different wound dressings including a dressing as described above with respect to FIG. 1 (column A). Columns B, C and D show the results for other foam dressings. The graph represents the average pressure measured underneath a dressing (as measured by a Tekscan pressure reading mat and software as described above) when the upper surface of the dressing (non-wound contacting side) is impacted at a speed of 3 m/min by a probe until a pressure of 735 mmHg is applied. The area of pressure application was a 10 mm diameter cylindrical probe, onto which a rubber ball of 6.5 cm diameter was attached. It is estimated that the area over which the rubber ball contacted the top of the dressing was 3% of the total area of the rubber sphere, that is 4 cm². This can be compared to a cylindrical probe of diameter 2.25 cm. A summary of the pressure transferred and the area over which pressure was transferred is shown in Table 1 below.

TABLE 1

| Sample | Average pressure transferred (mmHg) | Estimated area over which pressure is transferred (cm²) |
|---|---|---|
| Pressure applied | 735 | 4 |
| Dressing of FIG. 1 (A) | 25 | 12.3 |
| Dressing B (foam composite) | 39 | 10.6 |
| Dressing C (foam) | 36 | 11.7 |
| Dressing D (foam) | 31 | 117 |

Preferably the dressing area to be tested is of 20 cm² or more when using a cylindrical probe of 10 mm diameter, to ensure that the probe size is not larger than the test sample and to ensure pressure is redistributed efficiently through the sample.

Aptly the pressure spreading layer increases the area over which pressure is transferred by at least 25% of the initial application area and more aptly by at least 50% of the initial application area.

The inventors have found that a combination of materials may, as a composite, increase the area over which pressure is transferred by at least 50%, aptly at least 100%, more aptly at least 200% of the initial application area. An increase in the area over which pressure is transferred of 200%.

Individual components can also be assessed for pressure redistribution from a static test, where a pressure of 736 mmHg is applied statically to various materials. Values obtained are shown in the table below:

TABLE 2

| Sample | Average pressure transferred (mmHg) | Area over which pressure is transferred (cm2) |
|---|---|---|
| Pressure applied | 736 | 0.8 |
| Foam | 301 | 1.2 |
| Superabsorbent layer | 198 | 1.8 |
| 3D fabric #1 | 249 | 1.5 |
| 3D fabric #2 | 173 | n/a |
| Composite dressing | 53 | 6.4 |

The above-described tests on pressure dissipation suggest that a dressing including a shielding layer such as a 3-D spacer layer and optionally also an absorbent layer give enhanced performance in terms of spreading a pressure applied, and thus should perform better against accidental knocks to the wound site for example, compared to known dressings.

Figure 14:
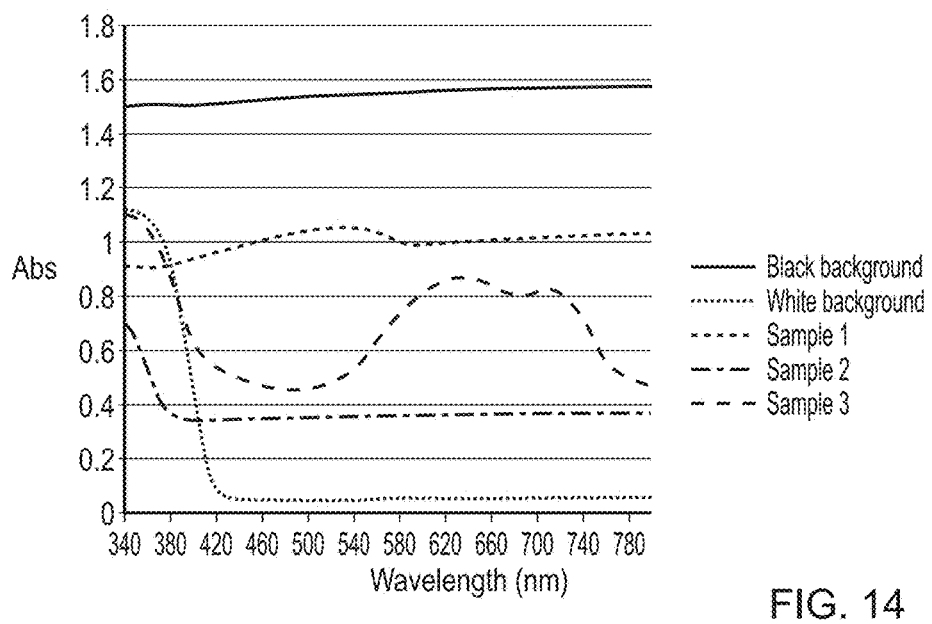
FIG. 14 illustrates UV-visible spectrum absorbency of various materials.

The inventors also performed tests upon various dressings with respect to the masking properties of the dressing. The ability to mask colour may be calculated, for example, by measuring the reduction in absorption of light radiation at particular wavelengths. FIG. 14 illustrates the absorption at various different wavelengths of 3 different samples. The tests utilized a UV-Vis spectrophotometer Jasco with integrating sphere, with a scanning range 340 to 800 nm, bandwidth 5 nm and 1000 nm/sec scanning speed. The data labelled black background represents the extreme of exudate colour (the most colour an exudate might have)—the highest level of radiation absorbed and the least amount of radiation reflected from the sample. The data for white background represents the upper limit for total masking—generally the lowest level of radiation absorbed and the highest level of reflection. Sample 1 was a tinted polymer film placed over a black background, which was judged, not to sufficiently mask the black background (representing wound exudate) satisfactorily. Sample 2 was a sheet of 3-dimensional spacer fabric (Baltex 3D) placed over a black background, and was judged to provide adequate masking of the black background. Sample 3 was a sheet of non-woven material dyed green placed over a black background, and provided complete masking of the black background.

The inventors noted that any wound exudate may have dark yellow, red and/or brown tones. Therefore, to appropriately mask these colours, a masking layer would need to shield light wavelengths of below 600 nm.

Measuring the reduction in absorption of light radiation at particular wavelengths may be performed by calculating:

% reduction=$(A_{background}-A_{sample\ placed\ on\ background})/(A_{background})\times 100$ where A is the absorption of light radiation at the particular wavelength.

Using this formula, using light at a wavelength of 460 nm, the percentage of absorption reduction was calculated as shown in Table 3 below.

TABLE 3

| Sample | Absorption reduction at 460 nm | Appropriate masking observed |
|---|---|---|
| Sample 1 | 34% | No |
| Sample 2 | 77% | Yes - partial |
| Sample 3 | 69% | Yes - complete |

It has been found that materials that reduce light absorption by about 50% or more will provide enough partial or complete masking of wound exudate (as judged by the inventors). Of course a complete masking element wound preferably require a means for a clinician to judge the spread of wound exudate in the dressing below the masking element, e.g. the masking element not completely covering the entire dressing. Alternatively a partial masking element may allow a clinician to judge the spread of exudate in the dressing below without additional means.

It will be understood that the wetting of a masking material (by exudate for example) will also affect the masking performance of the masking element, since hydrophilic materials will allow chromophore-carrying species to travel through them more easily. As such, the absorption reduction rate should also be tested on wet materials.

The inventors also tested the above-mentioned Samples 1, 2 and 3 for their masking properties by measuring CIE L*a*b* values (a known 3-dimensional model for representing colour space). The analysis employed Jasco software using the range 380 to 780 nm, stard observed 2(deg), lightsource D65, colour matching JIS Z8701-1999.

Table 4 below shows the L*a*b* values found when Samples 1, 2 and 3 were respectively placed over a black background. The results for the black background alone and a white background are also shown.

TABLE 4

| Sample | CIE L*a*b* values recorded | | | Appropriate masking observed? |
|---|---|---|---|---|
| | L* | a* | b* | |
| Black background | 0 | 0 | 0 | n/a |
| Sample 1 (on black) | 36.59 | 3.76 | −1.80 | No |
| Sample 2 (on black) | 71.76 | −0.20 | −1.08 | Yes - partial |
| Sample 3 (on black) | 70.64 | −0.25 | −1.23 | Yes - complete |
| White background | 100 | 0 | 0 | n/a |

Generally, samples which lead to an increase in L* value will provide a lighter colour tone than the reference surface, which is the main contributor to masking a dark colour. From the values above, apt partial masking materials will yield an L* value above 50, or more aptly above 70.

However, completely opaque masking layers, such as for example a tinted polymeric film, may cover the area to be masked with a darker tone altogether, in which case the measure of L* is not relevant.

Once again these values should also be considered on wet material, for the reasons stated above.

In addition, the dressing of the disclosure may be arranged to prevent shear stress between layers from causing damage to the dressing. This is because the layers are generally not adhered together, other than the top film 102 and wound contact layer 101 being adhered in the border region 110. Thus even if friction or other energy from shear movement occurs, the energy is dissipated by the layers prior to reaching the patient.

The wound facing surface of a wound dressing may be provided with a release coated protector (not shown in the figures), for example a silicon-coated paper. The protector covers the wound contacting side of the dressing prior to application to a patient, and can be peeled away at the time of use.

Various modifications to the detailed arrangements as described above are possible. For example, dressings according to the present disclosure do not require each of the specific layers as described above with respect to FIG. 1. Dressings may include only one layer, or any combination of the layers described above. Alternatively or additionally, the materials of the layers described above may be combined into a single layer or sheet of material to perform the functions of each layer by a single layer.

As noted above, each of the layers described may be used to give one or more function to the wound dressing. As such, each of the layer materials may be used separately or in any combination such that each material provides the given function.

The wound contact layer described above is an optional layer. If used, a wound contact layer may be of any suitable material, such as polyethylene (or polyurethane as described above) or other suitable polymer, and may be perforated for example by a hot pin process, laser ablation process, ultrasound process or in some other way so as to be permeable to fluids.

Although the dressing described above has been described having a border region and a central region this need not be the case. The dressing may be provided without an adhesive layer for attachment to the skin of a patient. Rather, another means may be provided for locating the dressing at the correct position over a wound, such as adhesive tape or a tied bandage.

The relative widths of the various layers may be all the same or different to those as shown in the figures.

The dressing pad assembly may optionally be arranged with layers so that odour control is placed between two layers of different rates of absorptions. The odour control layer can be a charcoal cloth (knitted, woven, felt, non-woven), or any other textile, foam, gel, net or mesh impregnated with odour-control materials. Such odour control materials can be cyclodextrins, zeolites, ion-exchange resins, oxidising agents, activated charcoal powder. It is also possible to use said odour-control materials dispersed in any layer of the pad assembly, and not as a discrete layer.

The dressing may optionally include a means of partially obscuring the top surface. This could also be achieved using a textile (knitted, woven, or non-woven) layer without openings, provided it still enables fluid evaporation from the absorbent structure. It could also be achieved by printing a masking pattern on the top film, or on the top surface of the uppermost pad component, using an appropriate ink or coloured pad component (yarn, thread, coating) respectively. Another way of achieving this would be to have a completely opaque top surface, which could be temporarily opened by the clinician for inspection of the dressing state (for example through a window), and closed again without compromising the environment of the wound.

The dressing may optionally be arranged such that it has enhanced compatibility with body movement. This could also be achieved using a different shape for the sub-areas, such as diamonds, triangles, or a plurality of such shapes tessellated across the area of the dressing. Alternatively, preferential folding lines may be scored within the thickness of the dressing material, and thus define independent sub-areas for adapting to movement.

Alternatively, the layers could be bonded using an elastic material, such as a viscoelastic adhesive, which would allow shear between the layers but refrain them from becoming separated and shifting across the pad.

A dressing may optionally be arranged that provides enhanced protection against mechanical forces. Other ways of achieving this include:
  Incorporation of pressure-relieving components within other layers of the dressing, such as within the foam layer (e.g. moulding the foam around a 3-D structure capable of spreading load)
  Incorporation of pressure-absorbing component within other layers of the dressing (e.g. beads of viscoelastic material incorporated in the superabsorbent layer)

A dressing assembly may optionally be arranged where the flowing properties are being provided by given material layers, and where the respective position of these layers provides additional properties on top of those from the individual layers. Alternative arrangement of layers than that described above may still provide some of the properties sought.

For example, placing the shielding layer (106) below the superabsorbent layer (105) would still allow protection from point pressure, but would lose the masking ability of this layer, and would probably affect the transmission of fluid between the foam layer (103) and the superabsorbent layer (105).

Another example is the placement of the odour control layer or component further away from the wound: this can be seen as beneficial because some types of odour control work differently depending on whether they are wet or dry. Placing a colour-less odour control component towards the top of the dressing (anywhere above (105)) could provide odour control properties without the visual impact that a black layer of charcoal cloth would have.

It can also be envisaged that several properties are combined within one layer, for example superabsorbent and odour control components could be incorporated in the foam structure. The only remaining optional properties to provide in this case would be protection and masking, which could be achieved by placing a layer (106) directly above such a modified foam if needed.

Interestingly, the fluid handling properties of an embodiment where the superabsorbing function is located within the lowest part of the dressing pad may not be as beneficial as those of an embodiment where the functions are held in separate layers, and the fluid is directed from one layer to another.

In another embodiment, the shielding layer 106 is of the same dimensions as 105, and clinical judgment of the exudate spread can be made by observing the spread of exudate through the masking layer. This embodiment has the advantage of completely masking unsightly exudate from the superabsorbent layer.

Figure 12A:
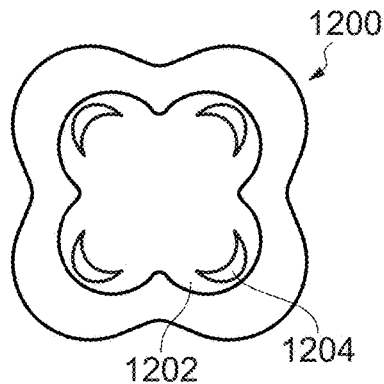
FIG. 12a illustrates an alternative dressing arrangement.
Figure 12B:
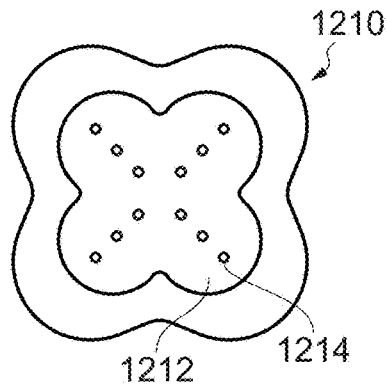
FIG. 12b illustrates another dressing arrangement.
Figure 12C:
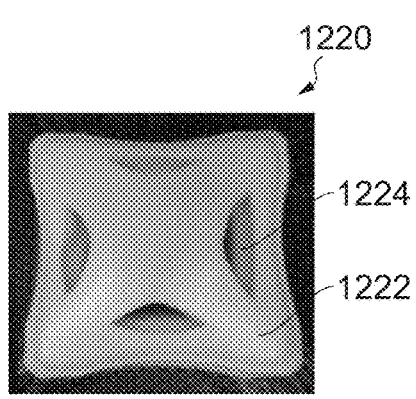
FIG. 12c shows a photograph of a yet further dressing arrangement.

Alternatively or additionally, the shielding layer can be provided with full masking capability, and windows provided at discrete points of the layer for enabling judgement of the exudate spread below such layer. Examples of such windows are illustrated in FIGS. 12a and 12b. The dressing 1200 shown in FIG. 12a includes a masking layer 1202 and crescent-shaped windows 1204 provided in the masking layer to extend through the layer allowing visibility of the dressing therebelow. The dressing 1210 of FIG. 12b includes a masking layer 1212 and a number of holes 1214 therethrough acting as windows for viewing the state of the dressing therebelow. FIG. 12c shows another dressing 1220 including a masking layer 1222 with windows 1224. With the dressings 1200, 1210, 1220 the progress of exudate spread over the dressing and towards the edge of the dressing can be monitored. In other alternatives instructions may be given to change the dressing when the exudate reaches a predetermined distance from the edge of the dressing, such as 5 mm from the dressing edge or 7 mm from the dressing edge, etc. Alternatively a 'traffic light' system may be implemented whereby an electronic indicator shows green, amber or red light to indicate the spread of exudate in the dressing. Alternatively or additionally, another suitable indicator may be used for indicating the spread of exudate over the dressing.

In another embodiment, odour control is not provided by a separate layer (i.e. no layer 104), but instead the odour-control material (activated charcoal, cyclodextrin, ion exchange resin, or other) is dispersed throughout another layer. This can be envisaged within the foam (103), the superabsorbent structure (105), or as a coating onto the masking layer (106).

In addition or alternatively, the obscuring layer may be coated with or formed from a material with size-exclusion properties to help with masking the exudate from view. For example, such a layer could have its lowermost side (the side closer to the wound) coated with materials such as zeolites or clays such as bentonite or sepiolite (the charged surface of which will tend to attract proteins and protein derivatives containing chromophores), other inorganic powders or molecular sieves (e.g. amberlite), proteins (albumin, haemoglobin components with molecular weight 15 to 70 KDa), ionic complexes such as hemes (molecular weight 600 to 850 g/mol), which have the function of immobilising species above a certain size or molecular weight. For example, species having molecular weight above 100 g/mol.

The shielding layer may be coated with or be formed of a hydrophilic compound (e.g. polyesters, polyurethanes, polyureas, polysaccharides, etc.) for assisting in wicking moisture towards the surface of the dressing, helping breathability of the dressing.

The shielding layer may be combined with a cover layer, such as an opaque or dark pigmented top layer.

The shielding layer (acting as a masking layer) may be combined with an absorbent layer, for example by providing an absorbent layer that has been dyed, for example with a dark blue pigment to the fibres of a non-woven or airlaid material.

The shielding layer (acting as a pressure relieving layer) may be combined with an absorbent layer. For example a fibrous superabsorber layer may be provided with a high density of fibres for spreading point pressure. Alternatively a hydrophilic foam may be moulded around pressure-redistributing structures of pillars or arrays of an elastomer material, for example.

Odour control can be combined with absorbency by dispersing particles of activated charcoal or other odour-catching material in a hydrophilic foam at time of reaction, or dispersing it throughout an air-laid material as a powder, or introducing it in the master batch of absorbent polymer used to manufacture fibres which will then be used in an air-laid.

As such, odour control, absorbency and pressure redistribution could be included in a single layer, and if this material was dyed, masking could also be performed.

The layers described herein may each be provided directly adjacent another layer or with further layers therebetween.

A wound dressing may be formed by bringing together a layer of absorbent material with a layer of obscuring material.

Alternatively a wound dressing may be formed by bringing together a layer of absorbent material with a layer of protective material.

Alternatively a wound dressing may be formed by bringing together a layer of absorbent material with a cover layer.

Alternatively a wound dressing may be formed by bringing together a layer of absorbent material with a fluid transmission layer with a layer of activated charcoal material therebetween.

Any of the methods above may include bringing layers together with adhesive over part or all of a layer. The method may be a lamination process.

Alternatively a wound dressing may be formed by bringing together layers as described with respect to FIG. 1, in a contiguous laminar stack, and adhering the top film to the wound contact layer in a border region.

Alternatively a wound dressing may be formed by forming a sheet of material for absorbing wound exudate, the sheet comprising at least one of a foam, an odour capturing material, an absorbent material, and a shielding material for masking or pressure spreading.

The dressing of the disclosure may be manufactured by continuous production techniques. For example, a sheet or sheets of suitable material may be run through rollers to enable the adhesion of one layer to another. Alternatively, pre-cut pad component shapes can be placed onto a web of one of the adhesive film or net components, before being encapsulated by the another adhesive film or net component. Then the dressing may be stamped out by cutting through the material in the desired shape and packaged.

In use, a wound dressing of the present disclosure would be applied to a wound site of a patient with the surface of the wound contacting side of the dressing facing the wound site. The wound dressing would then be monitored over a predetermined time period to assess the extent of exudate present in the dressing. The dressing may be any of the examples and embodiments described herein.

The dressing may be monitored at predetermined intervals or at predetermined time(s) of the day. For example, the dressing may be monitored every 6 hours, or once every morning, lunchtime and evening, for example, or as required by the specific patient.

A method for determining the saturation of a wound dressing with wound exudate comprises:

viewing a wound dressing at predetermined intervals to assess the extent of exudate present in the wound dressing.

The dressing may be any of the dressings described herein.

With the above-described arrangements one or more advantages over known dressings may be achieved.

The disclosure described contains elements which lead to a combination of properties that is not currently being met by existing devices.

In particular, the combination of an effective odour-control layer, held between two absorbent layers of differential absorption power, yields an absorbent structure which does not require a barrier layer to remain efficient against odours.

The odour-removing layer is not bonded to adjacent layers. Because of this, the available surface area of active pores of the odour layer is not diminished. That is, in known dressings including an odour resistant layer of activated charcoal, the material is carbonised to insert carbon into the surface porosity of the layer. The layer is then adhered to an adjacent layer, thus coating some of the porous surface area with adhesive, and reducing the total surface porosity.

The present disclosure comprising a shaped pad and dressing border, working as more independent sub-units of the dressing than what can be seen for a standard square shape, yields better conformability with movement than standard shapes. The dressing remains conformable with the skin and comfortable to wear, allowing the patient to move whilst wearing the dressing, and without creating detrimental traction on the pen-wound skin, which could lead to slowing of wound healing.

Some embodiments of the present disclosure also help to reduce the unsightly appearance of a dressing during use, by using materials that impart partial masking of the dressing surface. The masking should preferably only be partial, to allow clinicians to access the information they require by observing the spread of exudate across the dressing surface. This property, which is very important in helping patients live better with their treatment, had not been achieved until now for absorbent, breathable dressings. The partial masking nature of the obscuring layer enables a skilled clinician to perceive a different colour caused by exudate, blood, by-products etc. in the dressing allowing for a visual assessment and monitoring of the extent of spread across the dressing. However, since the change in colour of the dressing from its clean state to a state with exudate contained is only a slight change, the patient is unlikely to notice any aesthetic difference. Reducing or eliminating a visual indicator of wound exudate from a patient is likely to have a positive effect on their health, reducing stress for example. Also, some embodiments of the present disclosure provide a mean of relieving point pressure that may be applied to the wound area, by introducing a breathable, shear resistant layer that does not have to be in contact with the skin. This construction maximises the absorbency capacity of the dressing by not replacing some of the absorbent area with pressure-relieving areas. Breathability of the part of the dressing in contact with the skin is also maximise, as the breathable wound contact layer, lower part of the pad, and film, are not impaired by the use of another structure in contact with the skin.

By providing an odour control layer between a foam and an absorber layer, this can help in allowing only excess fluid towards the absorber layer, whilst keeping the foam layer sufficiently moist to create a moist wound healing environment. This is because the odour layer does not draw fluid away from the foam layer at the same speed at which an absorbent layer would. The transfer of fluid from the foam layer to the absorbent layer is therefore slowed down (relative to having a foam layer directly adjacent an absorber layer). Therefore, only excess fluid is taken into the odour layer, thereby assisting in the foam layer maintaining some degree of moisture and not drying out.

That is, the absorption rate of the outer layer should aptly be higher than the absorption rate of the lower layer (closer to the wound).

Prior to the invention of the embodiments disclosed herein, it was generally believed that the wetting of activated charcoal would destroy the function of the material of performing odour capturing. As such, activated charcoal layers have been used as an outer layer protected from liquid by a barrier layer. However the inventors found that as long as the activated charcoal layer is not soaked in liquid the activated charcoal can perform sufficiently well as an odour removing layer.

When the layer of absorbent material folds over the edges of any other lower layers, the absorbent layer helps to prevent fluid from being squeezed from the dressing at the dressing edge region, thereby causing leakage. Various known dressings previously suffered from the risk of delamination of layers caused by fluid being squeezed towards the edge of the dressing, being driven between the layers and possibly escaping at the edge of the dressing. This may occur for example in a border region where a wound contact layer meets a cover layer, and any intermediate layers of the dressing are adjacent that border region. Aptly an absorbent layer including a superabsorber material is useful in preventing the release of any liquid, especially in the direction of the border region or edge of the dressing.

Alternative materials can be used for the absorbent layer to provide the fluid locking and leak prevention properties, for example:

absorbent or superabsorbent non-woven materials, which can be made of fibrous modified cellulose, fibrous modified chitosan, fibrous hydrophilic polyesters, fibrous cellulose, fibrous chitosan, fibrous polysaccharides absorbent or superabsorbent foams, which can be blown hydrophilic polyurethane foam, comprising superabsorbent particles or fibres; foams of hydrophilic polyvinylacetate absorbent or superabsorbent gels or solids, which can be hydrocolloid polymer structures, additionally comprising superabsorbent particles or fibres.

Additionally, any of the dressing embodiments disclosed herein can be used in with a source of negative pressure, such as a pump. Any of the dressing embodiments disclosed herein can also be used with a pump and a fluid or waste collection canister that can be put in fluid communication with the pump and the dressing so that the pump draws fluid or waste from the wound into the collection canister.

Additionally, in any embodiments, the pump can be a piezoelectric pump, a diaphragm pump, a voice coil actuated pump, a constant tension spring actuated pump, a manually actuated or operated pump, a battery powered pump, a DC or AC motor actuated pump, a combination of any of the foregoing, or any other suitable pump.

Figure 15B:
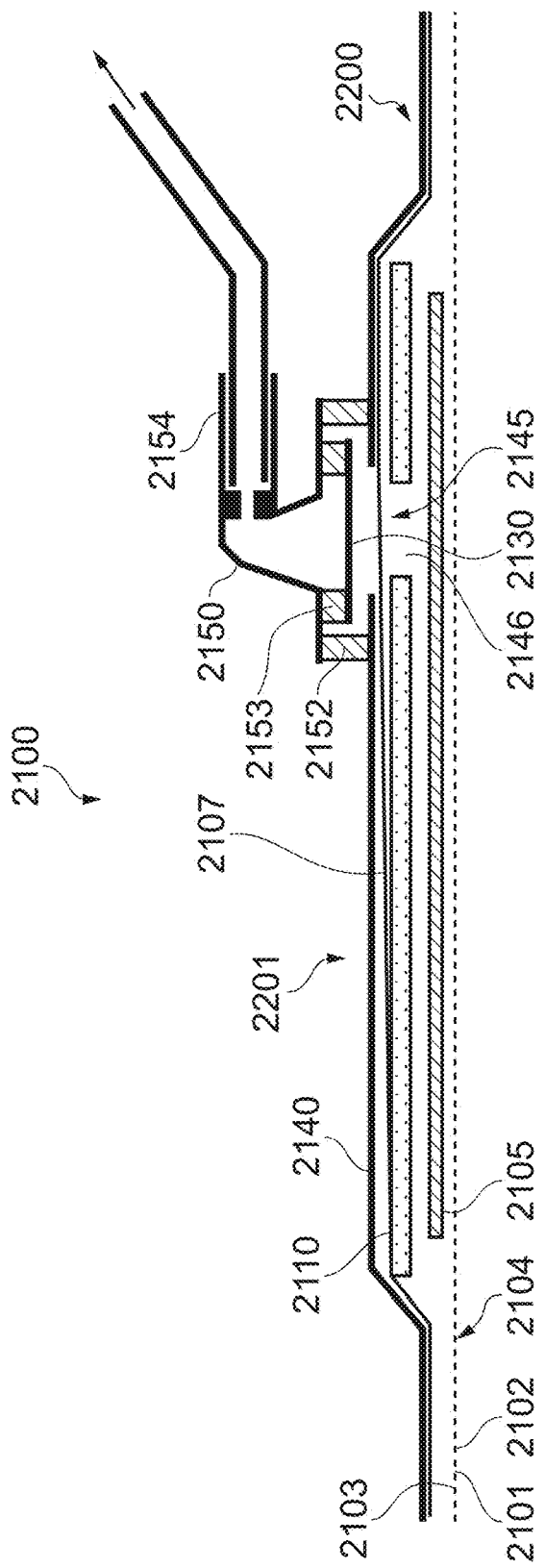
FIG. 15B illustrates another embodiment of a wound dressing.
Figure 16:
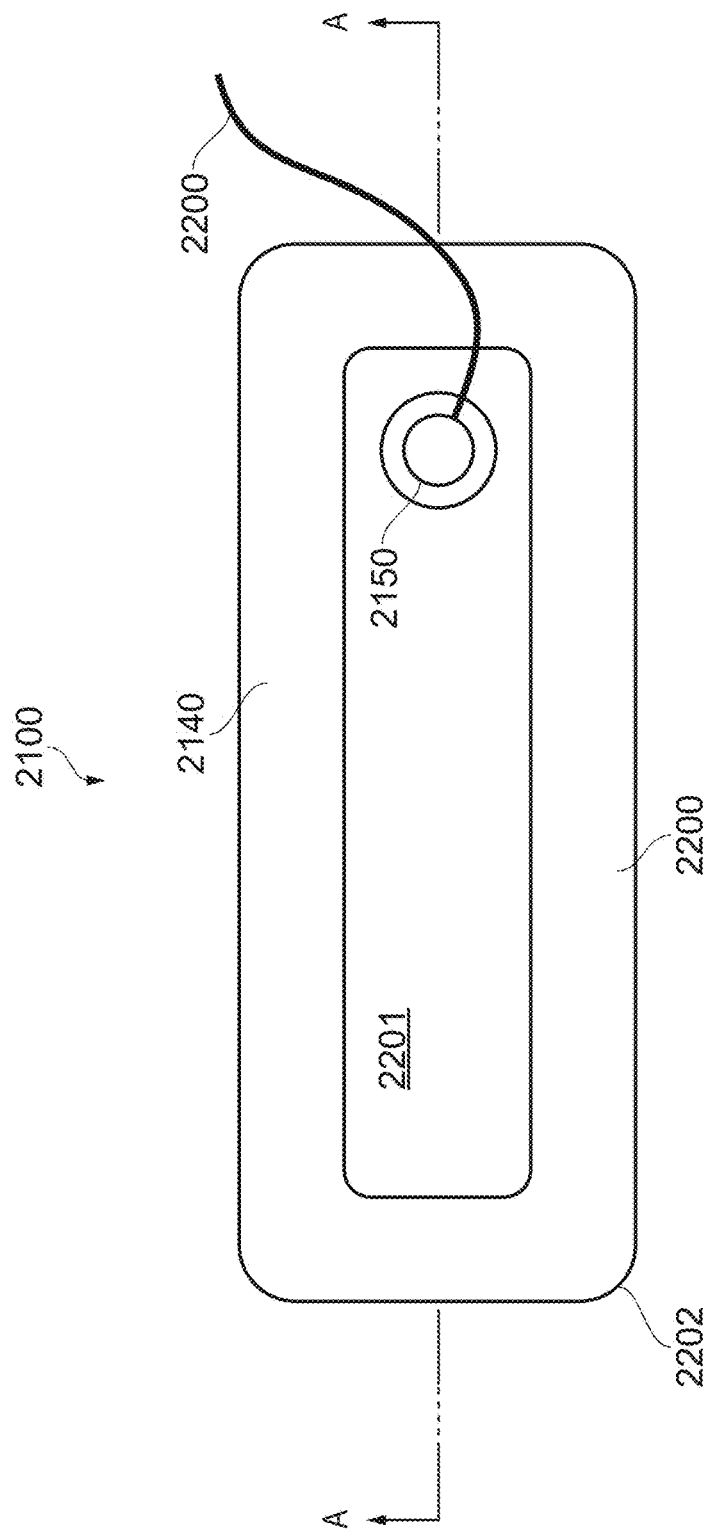
FIG. 16 illustrates a top view of an embodiment of a wound dressing.

FIGS. 15A-B illustrate cross sections through a wound dressing 2100 according to an embodiment of the disclosure. A plan view from above the wound dressing 2100 is illustrated in FIG. 16 with the line A-A indicating the location of the cross section shown in FIGS. 15A and 15B. It will be understood that FIGS. 15A-B illustrate a generalized schematic view of an apparatus 2100. It will be understood that embodiments of the present disclosure are generally applicable to use in TNP therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

The wound dressing 2100, which can alternatively be any wound dressing embodiment disclosed herein including without limitation wound dressing 100 or have any combination of features of any number of wound dressing embodiments disclosed herein, can be located over a wound site to be treated. The dressing 2100 forms a sealed cavity over the wound site. It will be appreciated that throughout this specification reference is made to a wound. In this sense it is to be understood that the term wound is to be broadly construed and encompasses open and closed wounds in which skin is torn, cut or punctured or where trauma causes a contusion. A wound is thus broadly defined as any damaged region of tissue where fluid may or may not be produced. Examples of such wounds include, but are not limited to, incisions, lacerations, abrasions, contusions, burns, diabetic ulcers, pressure ulcers, stoma, surgical wounds, trauma and venous ulcers or the like.

In some embodiments, it may be preferable for the wound site to be filled partially or completely with a wound packing material. This wound packing material is optional, but may be desirable in certain wounds, for example deeper wounds. The wound packing material can be used in addition to the wound dressing 2100. The wound packing material generally may comprise a porous and conformable material, for example foam (including reticulated foams), and gauze. Preferably, the wound packing material is sized or shaped to fit within the wound site so as to fill any empty spaces. The wound dressing 2100 may then be placed over the wound site and wound packing material overlying the wound site. When a wound packing material is used, once the wound dressing 2100 is sealed over the wound site, TNP is transmitted from a pump through the wound dressing 2100, through the wound packing material, and to the wound site. This negative pressure draws wound exudate and other fluids or secretions away from the wound site.

It is envisaged that the negative pressure range for the apparatus embodying the present disclosure may be between about −20 mmHg and −200 mmHg (note that these pressures are relative to normal ambient atmospheric pressure thus, −200 mmHg would be about 560 mmHg in practical terms). In one embodiment, the pressure range may be between about −40 mmHg and −150 mmHg. Alternatively a pressure range of up to −75 mmHg, up to −80 mmHg or over −80 mmHg can be used. Also in other embodiments a pressure range of below −75 mmHg could be used. Alternatively a pressure range of over −100 mmHg could be used or over −150 mmHg.

It will be appreciated that according to certain embodiments of the present disclosure, the pressure provided may be modulated over a period of time according to one or more desired and predefined pressure profiles. For example such a profile may include modulating the negative pressure between two predetermined negative pressures P1 and P2 such that pressure is held substantially constant at P1 for a pre-determined time period T1 and then adjusted by suitable means such as varying pump work or restricting fluid flow or the like, to a new predetermined pressure P2 where the pressure may be held substantially constant for a further predetermined time period T2. Two, three or four or more predetermined pressure values and respective time periods may be optionally utilized. Other embodiments may employ more complex amplitude/frequency wave forms of pressure flow profiles may also be provided e.g. sinusoidal, sore tooth, systolic-diastolic or the like.

As illustrated in FIGS. 15A-B a lower surface 2101 of the wound dressing 2100, which, again, can be any wound dressing embodiment disclosed herein including without limitation dressing embodiment 100 or have any combination of features of any number of wound dressing embodiments disclosed herein, can be provided by an optional wound contact layer 2102. The wound contact layer 2102 can be a polyurethane layer or polyethylene layer or other flexible layer which is perforated, for example via a hot pin process, laser ablation process, ultrasound process or in some other way or otherwise made permeable to liquid and gas. The wound contact layer has a lower surface 2101 and an upper surface 2103. The perforations 2104 are through holes in the wound contact layer which enables fluid to flow through the layer. The wound contact layer helps prevent tissue ingrowth into the other material of the wound dressing. The perforations are small enough to meet this requirement but still allow fluid through. For example, perforations formed as slits or holes having a size ranging from 0.025 mm to 1.2 mm are considered small enough to help prevent tissue ingrowth into the wound dressing while allowing wound exudate to flow into the dressing. The wound contact layer helps hold the whole wound dressing together and helps to create an air tight seal around the absorbent pad in order to maintain negative pressure at the wound. The wound contact layer also acts as a carrier for an optional lower and upper adhesive layer (not shown). For example, a lower pressure sensitive adhesive may be provided on the underside surface 2101 of the wound dressing whilst an upper pressure sensitive adhesive layer may be provided on the upper surface 2103 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized this helps adhere the wound dressing to the skin around a wound site.

A layer 2105 of porous material can be located above the wound contact layer. This porous layer, or transmission layer, 2105 allows transmission of fluid including liquid and gas away from a wound site into upper layers of the wound dressing. In particular, the transmission layer 2105 ensures that an open air channel can be maintained to communicate negative pressure over the wound area even when the absorbent layer has absorbed substantial amounts of exudates. The layer should remain open under the typical pressures that will be applied during negative pressure wound therapy as described above, so that the whole wound site sees an equalized negative pressure. The layer 2105 is formed of a material having a three dimensional structure. For example, a knitted or woven spacer fabric (for example Baltex 7970 weft knitted polyester) or a non-woven fabric could be used. Other materials could of course be utilized, and examples of such materials are described below with respect to FIGS. 37-41.

In some embodiments, the transmission layer comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 100 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized.

The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer helps lock the liquid away or itself wicks the liquid onwards towards the cover layer where it can be transpired.

Preferably, to improve the liquid flow across the transmission layer (that is to say perpendicular to the channel region formed between the top and bottom spacer layers, the 3D fabric is treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 2110 of absorbent material is provided above the transmission layer 2105. The absorbent material which may be a foam or non-woven natural or synthetic material and which may optionally include or be super-absorbent material forms a reservoir for fluid, particularly liquid, removed from the wound site and draws those fluids towards a cover layer 2140. With reference to FIGS. 15A and 15B, a masking or obscuring layer 2107 can be positioned beneath the cover layer 2140. In some embodiments, the masking layer 2107 can have any of the same features, materials, or other details of any of the other embodiments of the masking layers disclosed herein, including but not limited to having any viewing windows or holes. Additionally, the masking layer 2107 can be positioned adjacent to the cover layer, or can be positioned adjacent to any other dressing layer desired. In some embodiments, the masking layer 2107 can be adhered to or integrally formed with the cover layer. In some embodiments the masking layer 2107 may optionally contain a hole (not shown) directly adjacent to the port 2150 to improve air flow through the layer.

The material of the absorbent layer also prevents liquid collected in the wound dressing from flowing in a sloshing manner. The absorbent layer 2110 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 2110 may typically be manufactured from ALLEVYN™ foam, Freudenberg 114-224-4 and/or Chem-Posite™ 11C-450.

In some embodiments, the absorbent layer is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. Also, all regions of the absorbent layer are provided with liquid.

The wicking action also assists in bringing liquid into contact with the upper cover layer to aid increase transpiration rates of the dressing.

The wicking action also assists in delivering liquid downwards towards the wound bed when exudation slows or halts. This delivery process helps maintain the transmission layer and lower wound bed region in a moist state which helps prevent crusting within the dressing (which could lead to blockage) and helps maintain an environment optimized for wound healing.

In some embodiments, the absorbent layer may be an air-laid material. Heat fusible fibers may optionally be used to assist in holding the structure of the pad together. It will be appreciated that rather than using super-absorbing particles or in addition to such use, super-absorbing fibers may be utilized according to certain embodiments of the present disclosure. An example of a suitable material is the Product Chem-Posite™ 11 C available from Emerging Technologies Inc (ETi) in the USA.

Optionally, according to some embodiments of the present disclosure, the absorbent layer may include synthetic stable fibers and/or bi-component stable fibers and/or natural stable fibers and/or super-absorbent fibers. Fibers in the absorbent layer may be secured together by latex bonding or thermal bonding or hydrogen bonding or a combination of any bonding technique or other securing mechanism. In some embodiments, the absorbent layer is formed by fibers which operate to lock super-absorbent particles within the absorbent layer. This helps ensure that super-absorbent particles do not move external to the absorbent layer and towards an underlying wound bed. This is particularly helpful because when negative pressure is applied there is a tendency for the absorbent pad to collapse downwards and this action would push super-absorbent particle matter into a direction towards the wound bed if they were not locked away by the fibrous structure of the absorbent layer.

The absorbent layer may comprise a layer of multiple fibers. Preferably, the fibers are strand-like and made from cellulose, polyester, viscose or the like. Preferably, dry absorbent particles are distributed throughout the absorbent layer ready for use. In some embodiments, the absorbent layer comprises a pad of cellulose fibers and a plurality of super absorbent particles. In additional embodiments, the absorbent layer is a non-woven layer of randomly orientated cellulose fibers.

Super-absorber particles/fibers may be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc.

Preferably, the particles of superabsorber are very hydrophilic and grab the fluid as it enters the dressing, swelling up on contact. An equilibrium is set up within the dressing core whereby moisture passes from the superabsorber into the dryer surrounding area and as it hits the top film the film switches and the fluid vapor starts to be transpired. A moisture gradient is established within the dressing to continually remove fluid from the wound bed and ensure the dressing does not become heavy with exudate.

Preferably the absorbent layer includes at least one through hole located so as to underly the suction port. As illustrated in FIGS. 15A-B a single through hole can be used to produce an opening underlying the port 2150. It will be appreciated that multiple openings could alternatively be utilized. Additionally should more than one port be utilized according to certain embodiments of the present disclosure one or multiple openings may be made in the super-absorbent layer in registration with each respective port. Although not essential to certain embodiments of the present disclosure the use of through holes in the super-absorbent layer provide a fluid flow pathway which is particularly unhindered and this is useful in certain circumstances.

Where an opening is provided in the absorbent layer the thickness of the layer itself will act as a stand-off separating any overlying layer from the upper surface (that is to say the surface facing away from a wound in use) of the transmission layer 2105. An advantage of this is that the filter of the port is thus decoupled from the material of the transmission layer. This helps reduce the likelihood that the filter will be wetted out and thus will occlude and block further operation.

Use of one or more through holes in the absorption layer also has the advantage that during use if the absorbent layer contains a gel forming material, such as superabsorber, that material as it expands to absorb liquid, does not form a barrier through which further liquid movement and fluid movement in general cannot pass. In this way each opening in the absorbent layer provides a fluid pathway between the transmission layer directly to the wound facing surface of the filter and then onwards into the interior of the port.

A gas impermeable, but moisture vapor permeable, cover layer 2140 can extend across the width of the wound dressing, which can be any wound dressing embodiment disclosed herein including without limitation dressing embodiment 100 or have any combination of features of any number of wound dressing embodiments disclosed herein. The cover layer, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the cover layer and a wound site where a negative pressure can be established. The cover layer 2140 is sealed to the wound contact layer 2102 in a border region 2200 around the circumference of the dressing, ensuring that no air is drawn in through the border area, for example via adhesive or welding techniques. The cover layer 140 protects the wound from external bacterial contamination (bacterial barrier) and allows liquid from wound exudates to be transferred through the layer and evaporated from the film outer surface. The cover layer 2140 typically comprises two layers; a polyurethane film and an adhesive pattern spread onto the film. The polyurethane film is moisture vapor permeable and may be manufactured from a material that has an increased water transmission rate when wet.

The absorbent layer 2110 may be of a greater area than the transmission layer 2105, such that the absorbent layer overlaps the edges of the transmission layer 2105, thereby ensuring that the transmission layer does not contact the cover layer 2140. This provides an outer channel 2115 of the absorbent layer 2110 that is in direct contact with the wound contact layer 2102, which aids more rapid absorption of exudates to the absorbent layer. Furthermore, this outer channel 2115 ensures that no liquid is able to pool around the circumference of the wound cavity, which may otherwise seep through the seal around the perimeter of the dressing leading to the formation of leaks.

In order to ensure that the air channel remains open when a vacuum is applied to the wound cavity, the transmission layer 2105 must be sufficiently strong and non-compliant to resist the force due to the pressure differential. However, if this layer comes into contact with the relatively delicate cover layer 2140, it can cause the formation of pin-hole openings in the cover layer 2140 which allow air to leak into the wound cavity. This may be a particular problem when a switchable type polyurethane film is used that becomes weaker when wet. The absorbent layer 2110 is generally formed of a relatively soft, non-abrasive material compared to the material of the transmission layer 2105 and therefore does not cause the formation of pin-hole openings in the cover layer. Thus by providing an absorbent layer 2110 that is of greater area than the transmission layer 2105 and that overlaps the edges of the transmission layer 2105, contact between the transmission layer and the cover layer is prevented, avoiding the formation of pin-hole openings in the cover layer 2140.

The absorbent layer 2110 is positioned in fluid contact with the cover layer 2140. As the absorbent layer absorbs wound exudate, the exudate is drawn towards the cover layer 2140, bringing the water component of the exudate into contact with the moisture vapor permeable cover layer. This water component is drawn into the cover layer itself and then evaporates from the top surface of the dressing. In this way, the water content of the wound exudate can be transpired from the dressing, reducing the volume of the remaining wound exudate that is to be absorbed by the absorbent layer 2110, and increasing the time before the dressing becomes full and must be changed. This process of transpiration occurs even when negative pressure has been applied to the wound cavity, and it has been found that the pressure difference across the cover layer when a negative pressure is applied to the wound cavity has negligible impact on the moisture vapor transmission rate across the cover layer.

An orifice 2145 is provided in the cover film 2140 to allow a negative pressure to be applied to the dressing 2100. A suction port 2150 is sealed to the top of the cover film 2140 over the orifice 2145, and communicates negative pressure through the orifice 2145. A length of tubing 2220 may be coupled at a first end to the suction port 2150 and at a second end to a pump unit (not shown) to allow fluids to be pumped out of the dressing. The port may be adhered and sealed to the cover film 2140 using an adhesive such as an acrylic, cyanoacrylate, epoxy, UV curable or hot melt adhesive. The port 2150 is formed from a soft polymer, for example a polyethylene, a polyvinyl chloride, a silicone or polyurethane having a hardness of 30 to 90 on the Shore A scale.

An aperture or through-hole 2146 is provided in the absorbent layer 2110 beneath the orifice 2145 such that the orifice is connected directly to the transmission layer 2105. This allows the negative pressure applied to the port 2150 to be communicated to the transmission layer 2105 without passing through the absorbent layer 2110. This ensures that the negative pressure applied to the wound site is not inhibited by the absorbent layer as it absorbs wound exudates. In other embodiments, no aperture may be provided in the absorbent layer 2110, or alternatively a plurality of apertures underlying the orifice 2145 may be provided.

As shown in FIG. 15A, one embodiment of the wound dressing 2100 comprises an aperture 2146 in the absorbent layer 2100 situated underneath the port 2150. In use, for example when negative pressure is applied to the dressing 2100, a wound facing portion of the port 150 may thus come into contact with the transmission layer 2105, which can thus aid in transmitting negative pressure to the wound site even when the absorbent layer 2110 is filled with wound fluids. Some embodiments may have the cover layer 2140 be at least partly adhered to the transmission layer 2105. In some embodiments, the aperture 2146 is at least 1-2 mm larger than the diameter of the wound facing portion of the port 2150, or the orifice 2145.

A filter element 2130 that is impermeable to liquids, but permeable to gases is provided to act as a liquid barrier, and to ensure that no liquids are able to escape from the wound dressing. The filter element may also function as a bacterial barrier. Typically the pore size is 0.2 μm. Suitable materials for the filter material of the filter element 2130 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film 2140 over the orifice 2145. For example, the filter element 2130 may be molded into the port 2150, or may be adhered to both the top of the cover layer 2140 and bottom of the port 2150 using an adhesive such as, but not limited to, a UV cured adhesive.

It will be understood that other types of material could be used for the filter element 2130. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the disclosure, filter element 2130 comprises a support layer and an acrylic co-polymer membrane formed on the support layer. Preferably the wound dressing 2100 according to certain embodiments of the present disclosure uses microporous hydrophobic membranes (MHMs). Numerous polymers may be employed to form MHMs. For example, PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 2130 may also include an odor absorbent material, for example activated charcoal, carbon fiber cloth or Vitec Carbotec-RT Q2003073 foam, or the like. For example, an odor absorbent material may form a layer of the filter element 2130 or may be sandwiched between microporous hydrophobic membranes within the filter element.

The filter element 2130 thus enables gas to be exhausted through the orifice 2145. Liquid, particulates and pathogens however are contained in the dressing.

In FIG. 15B, an embodiment of the wound dressing 2100 is illustrated which comprises spacer elements 2152, 2153 in conjunction with the port 2150 and the filter 2130. With the addition of such spacer elements 2152, 2153, the port 2150 and filter 2130 may be supported out of direct contact with the absorbent layer 2110 and/or the transmission layer 2105. The absorbent layer 2110 may also act as an additional spacer element to keep the filter 2130 from contacting the transmission layer 2105. Accordingly, with such a configuration contact of the filter 2130 with the transmission layer 2105 and wound fluids during use may thus be minimized. As contrasted with the embodiment illustrated in FIG. 15A, the aperture 2146 through the absorbent layer 2110 may not necessarily need to be as large or larger than the port 2150, and would thus only need to be large enough such that an air path can be maintained from the port to the transmission layer 2105 when the absorbent layer 2110 is saturated with wound fluids.

In particular for embodiments with a single port 2150 and through hole, it may be preferable for the port 2150 and through hole to be located in an off-center position as illustrated in FIGS. 15A-B and in FIG. 16. Such a location may permit the dressing 2100 to be positioned onto a patient such that the port 2150 is raised in relation to the remainder of the dressing 2100. So positioned, the port 2150 and the filter 2130 may be less likely to come into contact with wound fluids that could prematurely occlude the filter 2130 so as to impair the transmission of negative pressure to the wound site.

Figure 25:
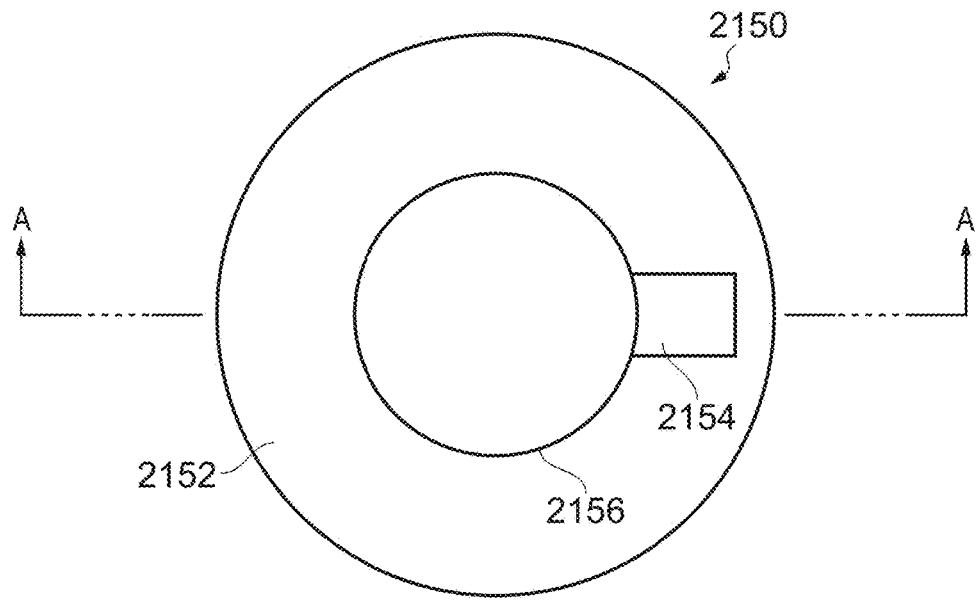
FIG. 25 illustrates a top view of a suction port.

FIG. 25 shows a plan view of a suction port 2150 according to some embodiments of the disclosure. The suction port comprises a sealing surface 2152 for sealing the port to a wound dressing, a connector portion 2154 for connecting the suction port 2150 to a source of negative pressure, and a hemispherical body portion 2156 disposed between the sealing surface 2152 and the connector portion 2154. Sealing surface 2152 comprises a flange that provides a substantially flat area to provide a good seal when the port 2150 is sealed to the cover layer 2140. Connector portion 2154 is arranged to be coupled to the external source of negative pressure via a length of tube 2220.

According to some embodiments, the filter element 2130 forms part of the bacterial barrier over the wound site, and therefore it is important that a good seal is formed and maintained around the filter element. However, it has been determined that a seal formed by adhering the filter element 2130 to the cover layer 2140 is not sufficiently reliable. This is a particular problem when a moisture vapor permeable cover layer is used, as the water vapor transpiring from the cover layer 2140 can affect the adhesive, leading to breach of the seal between the filter element and the cover layer.

Thus, according to some embodiments of the disclosure an alternative arrangement for sealing the filter element 2130 to stop liquid from entering the connector portion 2154 is employed.

Figure 26:
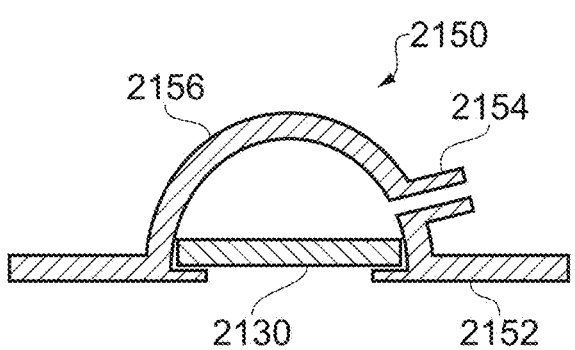
FIG. 26 illustrates a suction port including a filter element.

FIG. 26 illustrates a cross section through the suction port 2150 of FIG. 25 according to some embodiments of the disclosure, the line A-A in FIG. 25 indicating the location of the cross section. In the suction port of FIG. 26, the suction port 2150 further comprises filter element 2130 arranged within the body portion 2156 of the suction port 2150. A seal between the suction port 2150 and the filter element 2130 is achieved by molding the filter element within the body portion of the suction port 2150.

Figure 27:
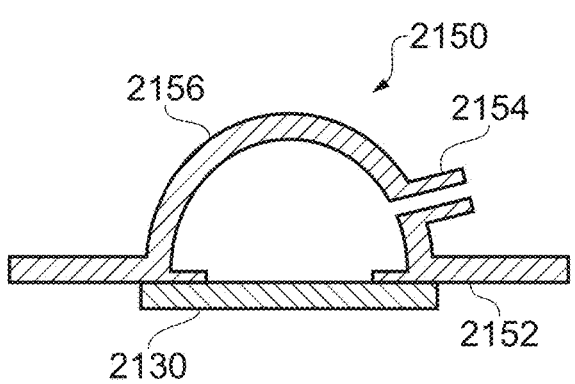
FIG. 27 illustrates a further suction port including a filter element.

FIG. 27 illustrates a cross section through the suction port 2150 of FIG. 25 according to some embodiments of the disclosure that can be used with any dressing embodiment disclosed herein. In the suction port of FIG. 27, the filter element 2130 is sealed to the sealing surface 2152 of the suction port 2150. The filter element may be 2D sealed to the sealing surface using an adhesive or by welding the filter element to the sealing surface.

By providing the filter element 2130 as part of the suction port 2150, as illustrated in FIGS. 26 and 27, the problems associated with adhering the filter element to the cover layer 2140 are avoided allowing a reliable seal to be provided. Furthermore, providing a sub-assembly having the filter element 2130 included as part of the suction port 2150 allows for simpler and more efficient manufacture of the wound dressing 2100.

While the suction port 2150 has been described in the context of the wound dressing 2100 of FIG. 15, it will be understood that the embodiments of FIGS. 26 and 27 are applicable to any wound dressing for applying a negative pressure to a wound disclosed herein or otherwise, wherein wound exudate drawn from the wound is retained within the dressing. According to some embodiments of the disclosure, the suction port 2150 may be manufactured from a transparent material in order to allow a visual check to be made by a user for the ingress of wound exudate into the suction port 2150.

The wound dressing 2100 and its methods of manufacture and use as described herein may also incorporate features, configurations and materials described in the following patents and patent applications that are all incorporated by reference in their entireties herein: U.S. Pat. Nos. 7,524,315, 7,708,724, and 7,909,805; U.S. Patent Application Publication Nos. 2005/0261642, 2007/0167926, 2009/0012483, 2009/0254054, 2010/0160879, 2010/0160880, 2010/0174251, 2010/0274207, 2010/0298793, 2011/0009838, 2011/0028918, 2011/0054421, and 2011/0054423; as well as U.S. application Ser. No. 12/941,390, filed Nov. 8, 2010, Ser. No. 29/389,782, filed Apr. 15, 2011, and Ser. No. 29/389,783, filed Apr. 15, 2011. From these incorporated by reference patents and patent applications, features, configurations, materials and methods of manufacture or use for similar components to those described in the present disclosure may be substituted, added or implemented into embodiments of the present application.

In operation the wound dressing 2100 is sealed over a wound site forming a wound cavity. A pump unit (illustrated in FIG. 42 and described in further detail below) applies a negative pressure at a connection portion 2154 of the port 2150 which is communicated through the orifice 2145 to the transmission layer 2105. Fluid is drawn towards the orifice through the wound dressing from a wound site below the wound contact layer 2102. The fluid moves towards the orifice through the transmission layer 2105. As the fluid is drawn through the transmission layer 2105 wound exudate is absorbed into the absorbent layer 2110.

Turning to FIG. 16 which illustrates a wound dressing 2100 in accordance with an embodiment of the present disclosure one can see the upper surface of the cover layer 2140 which extends outwardly away from a centre of the dressing into a border region 2200 surrounding a central raised region 2201 overlying the transmission layer 2105 and the absorbent layer 2110. As indicated in FIG. 16 the general shape of the wound dressing is rectangular with rounded corner regions 2202. It will be appreciated that wound dressings according to other embodiments of the present disclosure can be shaped differently such as square, circular or elliptical dressings, or the like.

The wound dressing 2100 may be sized as necessary for the size and type of wound it will be used in. In some embodiments, the wound dressing 2100 may measure between 20 and 40 cm on its long axis, and between 10 to 25 cm on its short axis. For example, dressings may be provided in sizes of 10×20 cm, 10×30 cm, 10×40 cm, 15×20 cm, and 15×30 cm. In some embodiments, the wound dressing 2100 may be a square-shaped dressing with sides measuring between 15 and 25 cm (e.g., 15×15 cm, 20×20 cm and 25×25 cm). The absorbent layer 2110 may have a smaller area than the overall dressing, and in some embodiments may have a length and width that are both about 3 to 10 cm shorter, more preferably about 5 cm shorter, than that of the overall dressing 2100. In some rectangular-shape embodiments, the absorbent layer 2110 may measure between 10 and 35 cm on its long axis, and between 5 and 10 cm on its short axis. For example, absorbent layers may be provided in sizes of 5.6×15 cm or 5×10 cm (for 10×20 cm dressings), 5.6×25 cm or 5×20 cm (for 10×30 cm dressings), 5.6×35 cm or 5×30 cm (for 10×40 cm dressings), 10×15 cm (for 15×20 cm dressings), and 10×25 cm (for 15×30 cm dressings). In some square-shape embodiments, the absorbent layer 2110 may have sides that are between 10 and 20 cm in length (e.g., 10×10 cm for a 15×15 cm dressing, 15×15 cm for a 20×20 cm dressing, or 20×20 cm for a 25×25 cm dressing). The transmission layer 2105 is preferably smaller than the absorbent layer, and in some embodiments may have a length and width that are both about 0.5 to 2 cm shorter, more preferably about 1 cm shorter, than that of the absorbent layer. In some rectangular-shape embodiments, the transmission layer may measure between 9 and 34 cm on its long axis and between 3 and 5 cm on its short axis. For example, transmission layers may be provided in sizes of 4.6×14 cm or 4×9 cm (for 10×20 cm dressings), 4.6×24 cm or 4×19 cm (for 10×30 cm dressings), 4.6×34 cm or 4×29 cm (for 10×40 cm dressings), 9×14 cm (for 15×20 cm dressings), and 9×24 cm (for 15×30 cm dressings). In some square-shape embodiments, the transmission layer may have sides that are between 9 and 19 cm in length (e.g., 9×9 cm for a 15×15 cm dressing, 14×14 cm for a 20×20 cm dressing, or 19×19 cm for a 25×25 cm dressing).

It will be understood that according to embodiments of the present disclosure the wound contact layer is optional. This layer is, if used, porous to water and faces an underlying wound site. A transmission layer 2105 such as an open celled foam, or a knitted or woven spacer fabric is used to distribute gas and fluid removal such that all areas of a wound are subjected to equal pressure. The cover layer together with the filter layer forms a substantially liquid tight seal over the wound. Thus when a negative pressure is applied to the port 2150 the negative pressure is communicated to the wound cavity below the cover layer. This negative pressure is thus experienced at the target wound site. Fluid including, air and wound exudate is drawn through the wound contact layer and transmission layer 2105. The wound exudate drawn through the lower layers of the wound dressing is dissipated and absorbed into the absorbent layer 2110 where it is collected and stored. Air and moisture vapor is drawn upwards through the wound dressing through the filter layer and out of the dressing through the suction port. A portion of the water content of the wound exudate is drawn through the absorbent layer and into the cover layer 2140 and then evaporates from the surface of the dressing.

As discussed above, when a negative pressure is applied to a wound dressing sealed over a wound site, in some dressing embodiments disclosed herein, fluids including wound exudate are drawn from the wound site and through the transmission layer 2105 toward the orifice 2145. Wound exudate is then drawn into the absorbent layer 2110 where it is absorbed. However, some wound exudate may not be absorbed and may move to the orifice 2145. Filter element 2130 provides a barrier that stops any liquid in the wound exudate from entering the connection portion 2154 of the suction port 2150. Therefore, unabsorbed wound exudate may collect underneath the filter element 2130. If sufficient wound exudate collects at the filter element, a layer of liquid wilt form across the surface of filter element 2130 and the filter element will become blocked as the liquid cannot pass through the filter element 2130 and gases will be stopped from reaching the filter element by the liquid layer. Once the filter element becomes blocked, negative pressure can no longer be communicated to the wound site, and the wound dressing must be changed for a fresh dressing, even though the total capacity of the absorbent layer has not been reached.

In a preferred embodiment, the port 2150, along with any aperture 2146 in the absorbing layer 2110 situated below it, generally aligns with the mid-longitudinal axis A-A illustrated in FIG. 16. Preferably, the port 2150 and any such aperture 2146 are situated closer to one end of the dressing, contrasted with a central position. In some embodiments, the port may be located at a corner of the dressing 2100, which again can be any dressing embodiment disclosed herein including without limitation dressing embodiment 100. For example, in some rectangular embodiments, the port 2150 may be located between 4 and 6 cm from the edge of the dressing, with the aperture 146 located 2 to 3 cm from the edge of the absorbent layer. In some square embodiments, the port 2150 may be located between 5 to 8 cm from the corner of the dressing, with the aperture 2146 located 3 to 5 cm from the corner of the absorbent layer.

Certain orientations of the wound dressing may increase the likelihood of the filter element 130 becoming blocked in this way, as the movement of the wound exudate through the transmission layer may be aided by the effect of gravity. Thus, if due to the orientation of the wound site and wound dressing, gravity acts to increase the rate at which wound exudate is drawn towards the orifice 2145, the filter may become blocked with wound exudate more quickly. Thus, the wound dressing would have to be changed more frequently and before the absorbent capacity of the absorbent layer 2110 has been reached.

In order to avoid the premature blocking of the wound dressing 2100 by wound exudate drawn towards the orifice 2145 some embodiments of the disclosure include at least one element configured to reduce the rate at which wound exudate moves towards the orifice 2145. The at least one element may increase the amount of exudate that is absorbed into the absorbent layer before reaching the orifice. 2145 and/or may force the wound exudate to follow a longer path through the dressing before reaching the orifice 2145, thereby increasing the time before the wound dressing becomes blocked.

Figure 17:
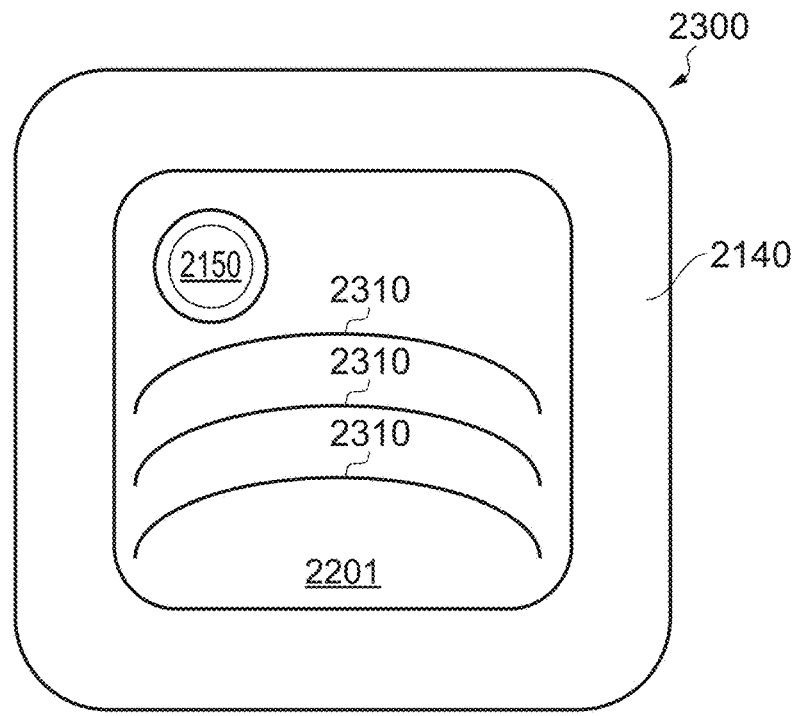
FIG. 17 illustrates a top view of an embodiment of a wound dressing embodiment, which can be any dressing embodiment disclosed herein, including baffle elements.

FIG. 17 shows a plan view of a wound dressing including baffle elements that reduce the rate at which wound exudate moves towards the orifice according to one embodiment of the disclosure. The wound dressing illustrated in FIG. 17 is similar to that shown in FIGS. 15 and 16, but includes a number of baffle elements 2310 disposed across the central raised region 2201. The baffle elements 2310 form barriers in the central region of the dressing, which arrest the movement of wound exudate towards the orifice.

Embodiments of baffle elements that may be used in the wound dressing described herein are preferably at (east partly flexible, so as to permit the wound dressing to flex and conform with the skin of the patient surrounding the wound site. When so present in the wound dressing, the baffle elements are preferably constructed so as to at least partially prevent liquid from flowing directly to the wound dressing port or orifice and its associated filter, if so provided. The baffle elements thus increase the distance that liquids may require to reach the port, which may help in absorbing these fluids into the absorbent or superabsorbent material of the wound dressing.

According to some embodiments of the disclosure, the baffle element may comprise a sealing region in which the absorbent layer 2110 and transmission layer 2105 are absent and cover layer 2140 is sealed to the wound contact layer 2101. Thus, the baffle element presents a barrier to the motion of the wound exudate, which must therefore follow a path that avoids the baffle element. Thus the time taken for the wound exudate to reach the orifice is increased.

In some embodiments, the baffle elements may be an insert of a substantially non-porous material, for example a closed-cell polyethylene foam, placed inside the dressing. In some cases, it may be preferable to place such an inserted baffle element in a sealing region where one or more of the absorbent layer 2110 and/or transmission layer 2105 are absent. A sealant, for example a viscous curing sealant such as a silicone sealant, could be placed or injected as a thin strip so as to form a baffle element that is substantially liquid impermeable. Such a baffle element could be placed or infected into a region of the transmission layer 2105 and/or absorbent layer 2110, or also a sealing region where the absorbent layer 2110 and/or transmission layer 2105 are absent.

Figure 20:
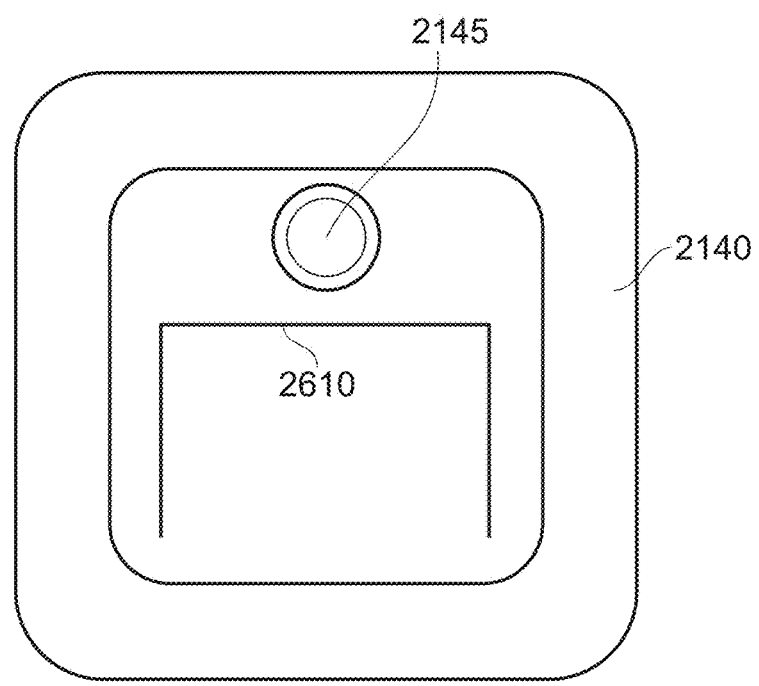
FIG. 20 illustrates a top view of an embodiment of a wound dressing, which can be any dressing embodiment disclosed herein, including a single baffle element.

FIG. 20 illustrates a wound dressing, which can be any embodiment of a wound dressing disclosed herein, including a baffle element according to a further embodiment of the disclosure. A single baffle element 2610 provides a cup shaped barrier between the bulk of the absorbent layer 2110 and the orifice 2145. Thus wound exudate that is initially drawn from the wound site within the region defined by the baffle element 2610, must follow a path around the outside of the cup shaped barrier to reach the orifice 2145. As will be recognized, the baffle element 2610 reduces the effect of gravity on reducing the time taken for the wound exudate to move to the orifice 2145, as for most orientations of the wound dressing at least a part of the path taken by the wound exudate will be against the force of gravity.

The embodiments of FIGS. 17 and 20 have been described with respect to a wound dressing having a structure as shown in FIG. 15. However, it will be understood that the baffle elements could equally be applied to a wound dressing in which the transmission layer 2105 was absent.

Figure 18:
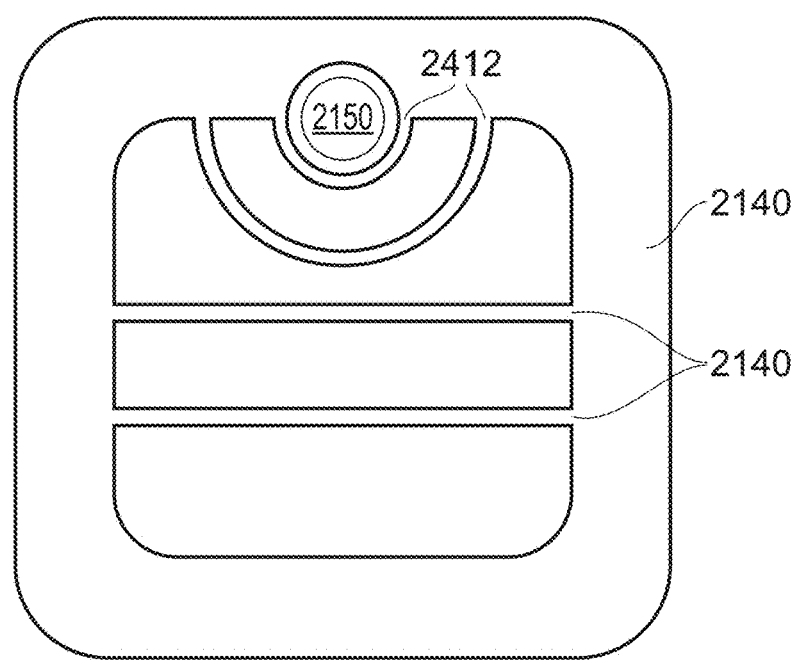
FIG. 18 illustrates a top view of a further wound dressing embodiment, which can be any dressing embodiment disclosed herein, including baffle elements.

FIG. 18 shows a plan view of a wound dressing including the at least one element according to one embodiment of the disclosure in which a number of baffle elements 2410 are provided that extend across the width of the central region 2201 of the wound dressing, with further baffle elements 2412 formed in a semi-circular path around the orifice 2145.

Figure 19:
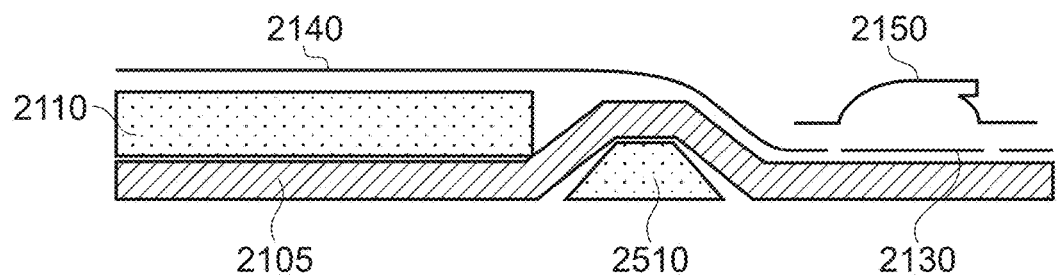
FIG. 19 illustrates a baffle element according to one embodiment.

FIG. 19 illustrates the configuration of baffle elements 2410 according to some embodiments of the disclosure. The baffle element comprises a channel of absorbent material 2510 underlying the transmission layer 2105. A channel in the absorbent layer 2110 is located over the baffle element 2410 so that the transmission layer is in contact with the cover layer 2140 in the region of the baffle element 2410. Thus, wound exudate that is moving along a lower surface of the transmission layer 2105, and has therefore not been drawn into absorbent layer 2110, will come into contact with and be absorbed by the channel of absorbent material 2510.

Alternatively, or additionally, baffle elements may comprise one or more channels provided in the surface of the transmission layer 2105 underlying and abutting the absorbent layer 2110. In use, when negative pressure is applied to the wound dressing, the absorbent layer 2110 will be drawn into the channel. The channel in the transmission layer may have a depth substantially equal to the depth of the transmission layer, or may have a depth less than the depth of the transmission layer. The dimensions of the channel may be chosen to ensure that the channel is filled by the absorbent layer 2110 when negative pressure is applied to the wound dressing. According to some embodiments, the channel in the transmission layer comprises a channel of absorbent material in the transmission layer 2105.

Figure 28A:
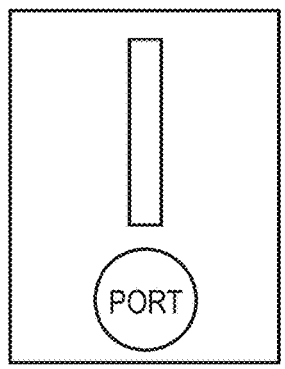
Figure 28B:
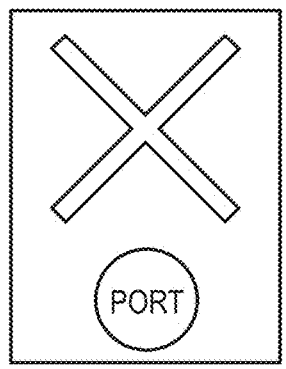
Figure 28C:
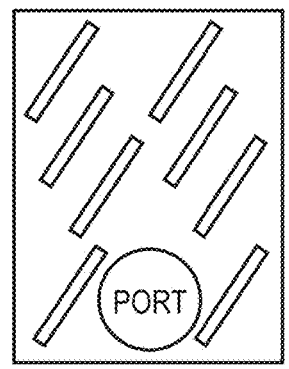
Figure 28D:
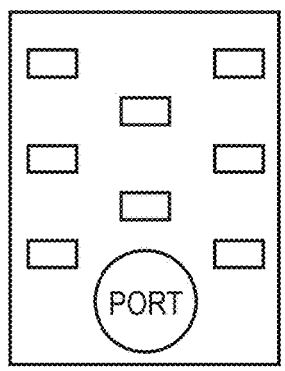
Figure 28E:
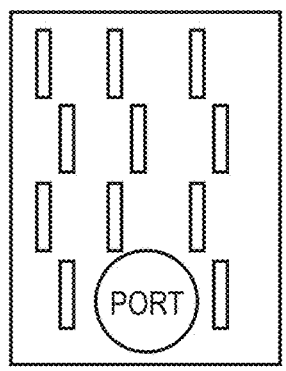

The baffle elements may be formed into a range of shapes and patterns, for example FIGS. 28A to 28L illustrate wound dressings having a number of different exemplifying configurations of baffle elements. FIG. 28A illustrates a linear baffle element in a vertical configuration aligned in the direction of the port or orifice. FIG. 28B illustrates an X-shaped baffle element. FIGS. 28C-E illustrate embodiments of wound dressings with multiple baffle elements, aligned in a generally diagonal, horizontal, or vertical manner.

Figure 28F:
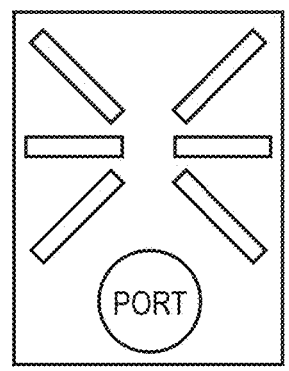
Figure 28G:
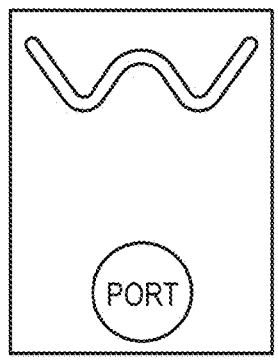
Figure 28H:
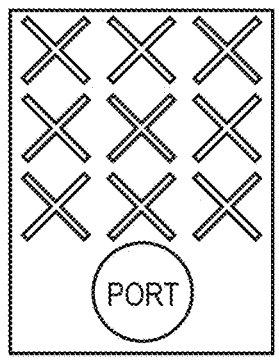
Figure 28I:
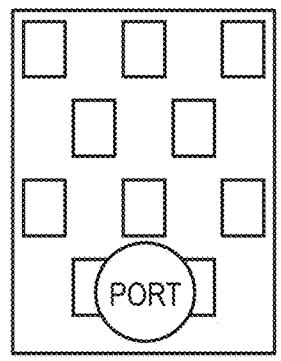
Figure 28J:
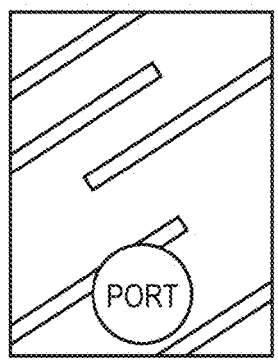
Figure 28K:
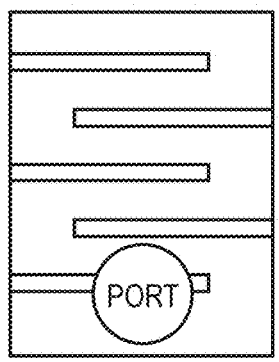
Figure 28L:
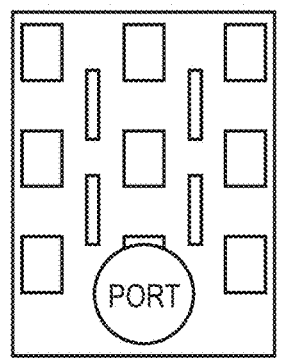

FIG. 28F illustrates baffle elements arranged in a six-armed starburst configuration, with a center portion left open. FIG. 28G illustrates a W-shaped baffle element on the wound dressing in a position distal to the port or orifice. In FIG. 28H, an 3-by-3 array of X-shaped baffle elements is provided on the wound dressing, although it will be understood that more or less X-shaped baffle elements may be used. FIG. 28I shows an embodiment with a plurality of rectangular bathe elements, and wherein one or more baffle elements are located underneath the port in the wound dressing. FIGS. 28J-K illustrate wound dressing embodiments with longer diagonal and horizontal baffle elements. In FIG. 28L, rectangular baffle elements are present on this embodiment of a wound dressing, wherein the baffle elements are of different sizes.

According to some embodiments of the disclosure, the at least one element comprises an array of vias, or troughs, in the transmission layer 2105. FIG. 29 illustrates a transmission layer 2105 that is perforated with diamond shaped vias 2210. The vias 2210 are arranged such that no linear pathway exists through the pattern of vias that does not intersect with one or more of the vias 2210.

When negative pressure is applied to the wound dressing, the absorbent layer 2110 is drawn into the vias 2210, increasing the area of the absorbent layer that comes into contact with wound exudate being drawn through the transmission layer 2105. Alternatively, the vias 2210 may be filled with further absorbent material for absorbing wound exudate being drawn through the transmission layer 2105. The vias may extend through the depth of the transmission layer 2105, or may extend through only part of the transmission layer.

Wound exudate moving through the transmission layer 2105 under the influence of gravity will fall through the transmission layer in a substantially linear manner. Any such linear pathways will, at some point, intersect with one of the vias 2210, and thus the exudate will be brought into contact with absorbent material within the vias 2210. Wound exudate coming into contact with absorbent material will be absorbed, stopping the flow of the wound exudate through the transmission layer 2105, and reducing the amount of unabsorbed wound exudate that may otherwise pool around the orifice. It will be appreciated that the vias are not limited to diamond shapes, and that any pattern of vias may be used. Preferably, the vias will be arranged to ensure that all linear paths through the transmission layer 2105 intersect with at least one via. The pattern of vias may be chosen to minimize the distance that wound exudate is able to travel though the transmission layer before encountering a via and being absorbed.

Figure 21:
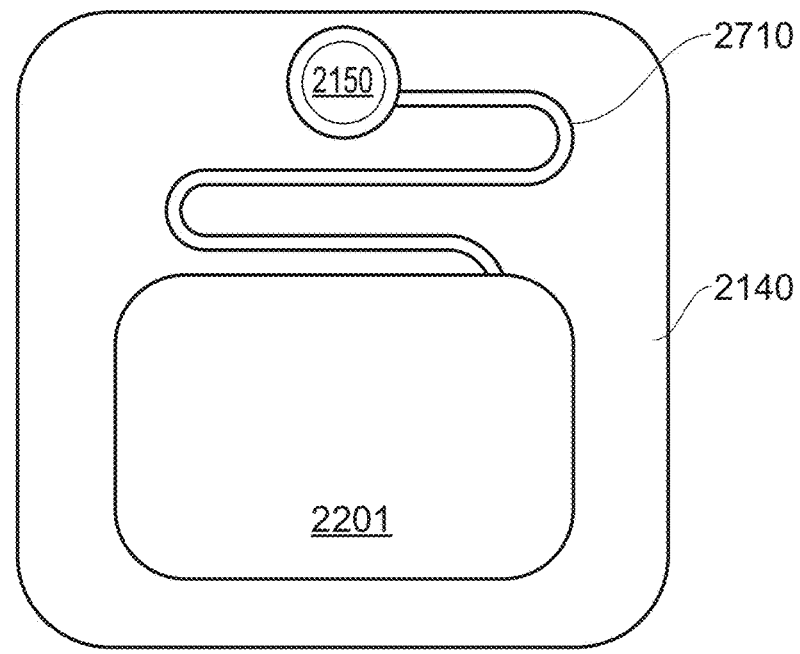
FIG. 21 illustrates a top view of an embodiment of a wound dressing, which can be any dressing embodiment disclosed herein, including an air channel.

FIG. 21 illustrates a wound dressing in accordance with some embodiments of the disclosure in which the at least one element comprises an air channel 2710 connecting the central region 2201 of the wound dressing to the orifice 2145. In the embodiment of FIG. 21, the air channel 2710 extends from an edge region of the transmission layer 2105 and connects the transmission layer to the orifice 2145.

In use, wound exudate is drawn towards the orifice 2145 by the application of negative pressure at the suction port 2150. However, the air channel 2710 present a relatively long serpentine path to be followed by the wound exudate before it reaches the orifice 2145. This long path increases the time that negative pressure can be applied to the dressing before wound exudate traverses the distance between the transmission layer and the orifice and blocks the filter element 2130, thereby increasing the time the dressing can be in use before it must be replaced.

Figure 22:
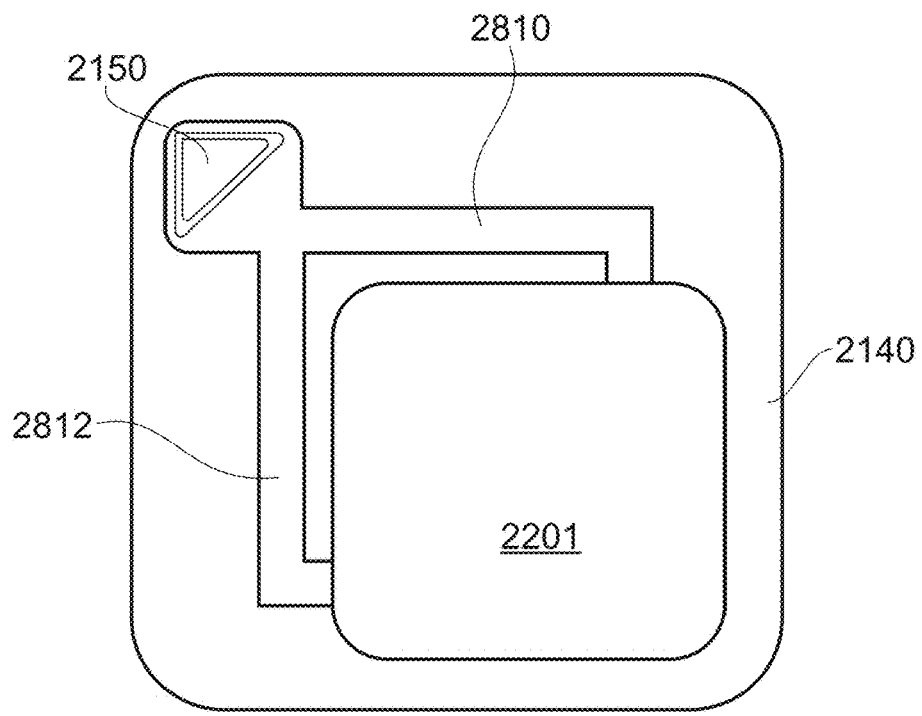
FIG. 22 illustrates a top view of an embodiment of a wound dressing, which can be any dressing embodiment disclosed herein, including two air channels.

FIG. 22 illustrates a wound dressing in accordance with one embodiment of the disclosure in which the at least one element comprises air channels 2810 and 2812 connecting the central region 2201 of the wound dressing to the orifice 2145. Channels 2810 and 2812 are coupled to the transmission layer at substantially opposite corners of the central region 2201.

The wound dressing shown in FIG. 22 reduces the effect of gravity on the time taken for the orifice to become blocked. If the wound dressing is in an orientation in which wound exudate moves under the influence of gravity towards the edge region of the transmission layer connected to air channel 2810, the effect of gravity will be to move wound exudate away from the edge region of the transmission layer coupled to air channel 2812, and vice versa. Thus, the embodiment of FIG. 22 provides alternative air channels for coupling the negative pressure to the transmission layer such that, should one air channel become blocked a remaining air channel should remain open and able to communicate the negative pressure to the transmission layer 2105, thereby increasing the time before negative pressure can no longer be applied to the wound dressing and the dressing must be changed.

Further embodiments of the disclosure may comprise greater numbers of air channels connecting the transmission layer 2105 to the orifice.

According to some embodiments of the disclosure, two or more orifices may be provided in the cover layer 2140 for applying the negative pressure to the wound dressing. The two or more orifices can be distributed across the cover layer 2140 such that if one orifice becomes blocked by wound exudate due to the wound dressing being in a particular orientation, at least one remaining orifice would be expected to remain unblocked. Each orifice is in fluid communication with a wound chamber defined by the wound dressing, and is therefore able to communicate the negative pressure to the wound site.

Figure 23:
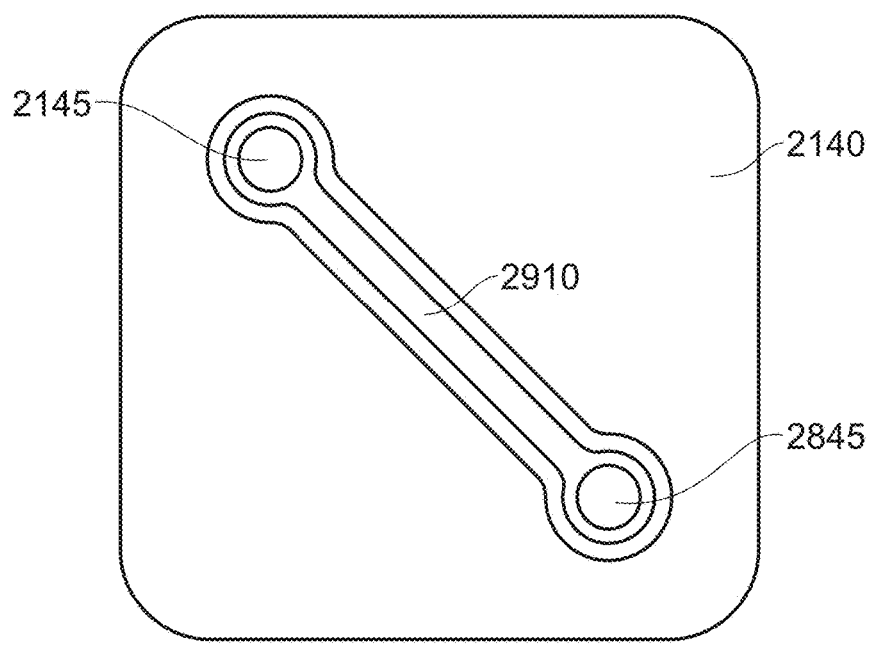
FIG. 23 illustrates a top view of an embodiment of a wound dressing, which can be any dressing embodiment disclosed herein, including two orifices in a cover layer coupled through a fluid communication passage.

FIG. 23 illustrates a wound dressing in accordance with a further embodiment of the disclosure. The wound dressing of FIG. 23 is similar to that of FIGS. 15A-B but includes two orifices 2145 and 2845 provided in the cover layer 2140. A fluid communication passage connects the two orifices such that a negative pressure applied to one of the orifices is communicated to the remaining orifice via the fluid communication passage. The orifices 2145, 2845 are located in opposite corner regions of the cover layer 2140. The fluid communication passage is formed using a flexible molding 2910 on the upper surface of the cover layer 2140. It will be appreciated that the flexible molding may be formed from other suitable means for example a strip of transmission or open porous foam layer placed on the cover layer 2140 between the orifices 2145 and 2845 and a further film welded or adhered over the strip thus sealing it to the cover layer and forming a passageway through the foam. A conduit may then be attached in a known manner to the sealing film for application of negative pressure.

In use, the wound dressing having two orifices is sealed over a wound site to form a wound cavity and an external source of negative pressure is applied to one of the orifices 2145, 2845, and the negative pressure will be communicated to the remaining orifice via the fluid communication passage. Thus, the negative pressure is communicated via the two orifices 2145, 845 to the transmission layer 2105, and thereby to the wound site. If one of the orifices 2145, 2845 becomes blocked due to wound exudate collecting at the orifice under the influence of gravity, the remaining orifice should remain clear, allowing negative pressure to continue to be communicated to the wound site. According to some embodiments, the transmission layer 2105 may be omitted, and the two orifices will communicate the negative pressure to the wound site via the absorbent layer 2110.

Figure 24:
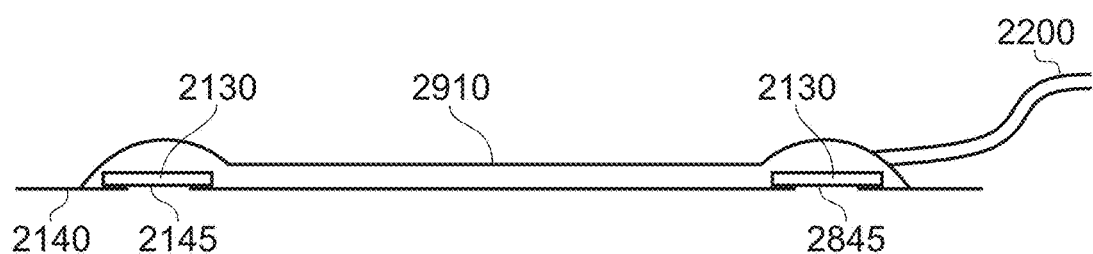
FIG. 24 illustrates an embodiment of the fluid communication passage.

FIG. 24 illustrates a side view of the fluid communication passage of the embodiment of FIG. 23. Molding 2910 is sealed to the top surface of the cover layer 2140, and covering orifices 2145 and 2845. Gas permeable liquid impermeable filter elements 2130 are provided at each orifice. The molding 2910 is coupled to an external source of negative pressure via a tube element 2220.

According to some embodiments, a single filter element may be used extending underneath the length of the fluid communication passage and the two orifices. While the above example embodiment has been described as having two orifices, it will be understood that more than two orifices could be used, the fluid communication passage allowing the negative pressure to be communicated between the orifices.

FIG. 30 illustrates an alternative arrangement in which a single elongate orifice 2350 is provided in the cover layer 2140. First and second ends 2355, 2356 of the orifice 2350 are located in opposite corner regions of the cover layer 2140. A flexible molding 2360 is sealed around the orifice 2350 and allows negative pressure to be communicated through the cover layer 2140 along the length of the orifice

2350. The flexible molding 2360 may be formed by any suitable means as described above in relation to flexible molding 2910.

In use, the wound dressing is sealed over a wound site to form a wound cavity and an external source of negative pressure is applied to the orifice. If, due to the orientation of the wound dressing, wound exudate moves under the influence of gravity to collect around one end 2355 of the orifice 2350, a portion of the orifice 2350 near to the end 2355 will become blocked. However, a portion of the orifice near to the remaining end 2356 should remain clear, allowing continued application of negative pressure to the wound site.

As still further options the dressing can contain antimicrobial e.g. nanocrystalline silver agents on the wound contact layer and/or silver sulphur diazine in the absorbent layer. These may be used separately or together. These respectively kill micro-organisms in the wound and micro-organisms in the absorption matrix. As a still further option other active components, for example, pain suppressants, such as ibuprofen, may be included. Also agents which enhance cell activity, such as growth factors or that inhibit enzymes, such as matrix metalloproteinase inhibitors, such as tissue inhibitors of metalloproteinase (TIMPS) or zinc chelators could be utilized. As a still further option odor trapping elements such as activated carbon, cyclodextrine, zeolite or the like may be included in the absorbent layer or as a still further layer above the filter layer.

FIG. 31 illustrates a first, upper surface 3700 and a further, lower surface 3702 of a transmission layer 2105 according to an embodiment of the present disclosure. In the embodiment illustrated in FIG. 31 fibers 3703 of a woven layer extend between the first surface 3700 and the further surface 3702. It will be appreciated that according to further embodiments of the present disclosure if a foam layer is used as a transmission layer 2105 the connected strands forming the foam will act as spacer elements. As illustrated in FIG. 31 in a relaxed mode of operation, that is to say when in use, no negative pressure is applied to the wound dressing or negative pressure is applied to the wound dressing but no external force acts on the wound dressing then the fibers 3703 extend substantially perpendicular to the upper and lower surfaces keeping the surfaces in a spaced apart substantially parallel configuration.

FIG. 32 illustrates the transmission layer 2105 when an external force is exerted on the outside of the dressing. The external force can be a compressive force indicated by arrow A and/or a lateral force illustrated by arrow B in FIG. 32. As indicated either a compressive force or a lateral force acts to cause the fibers 3703 to lean to one side. This causes the upper and lower surfaces to become laterally offset with respect to each other as well as causing the thickness of the layer to reduce from a separation distance r indicated in FIG. 31 in a relaxed mode of operation to a compression distance c illustrated in FIG. 32. The reduction in thickness effectively provides some "give" in the dressing even when the dressing is subject to negative pressure. It will be appreciated that the forces acting on the dressing may occur throughout the whole of the surface area of the dressing or only in one or more particular regions. In such a situation regions of the dressing can be in a relaxed mode of operation and further regions can be in a compressed mode of operation. As illustrated in FIG. 32 when a force is exerted on the transmission layer the fibers separating the upper and lower surfaces tend to lean to one side sharing a common lean angle.

Throughout this specification reference will be made to a relaxed mode of operation and a forced mode of operation.

It is to be understood that the relaxed mode of operation corresponds to a natural state of the material either when no negative pressure is applied or when negative pressure is applied. In either situation no external force, caused for example by motion of a patient or an impact is in evidence. By contrast a forced mode of operation occurs when an external force whether compressive, lateral or other is brought to bear upon the wound dressing. Such forces can cause serious damage/prevent healing or a wound.

FIG. 33 illustrates how certain embodiments of the present disclosure can also operate to offset load forces. As illustrated in FIG. 33 if a force is exerted over a contact area 3900 in an upper surface 3700 of the transmission layer 2105 then this force is transmitted across and through the transmission layer and is exerted over a larger dissipation area 3901 against an underlying wound site. In the case of use of a 3D knit as a transmission layer this is because the relatively stiff spacer elements provide at least some lateral stiffness to the layer.

FIG. 34 illustrates the transmission layer 2105 and absorbent layer 2110 of some embodiments in more detail. The absorbent layer 2110 is located proximate to the upper surface 3700 of the transmission layer 2105 and is unbonded thereto according to certain embodiments of the present disclosure. When unbonded the absorbent layer 2110 is also able to move laterally with respect to the underlying transmission layer when a lateral or shear force is applied to the wound dressing. Also the absorbent layer is able to further compress when a compressive force illustrated in FIG. 35 acts on the wound dressing. As illustrated in FIG. 35 the absorbent layer 2110 decreases in thickness under a compressive force from a non-compressed thickness x illustrated in FIG. 34 to a compressed distance y illustrated in FIG. 35. The compressive force also acts to offset the upper and lower surfaces of the transmission layer as described above thus enhancing the "give" of the dressing. The ability for an upper surface 4201 to translate laterally with respect to a lower surface 4202 of the absorbent layer under a lateral or shearing force exerted on the wound dressing is illustrated in more detail in FIG. 36. This lateral motion causes the thickness x of the absorbent layer 2110 to reduce and the upper surface and lower surface of the absorbent layer to be offset with respect to each other. This effect can itself be sufficient to prevent shear forces exerted on the whole or part of the wound dressing from being transferred to an underlying wound bed. As can the corresponding effect in the transmission layer. However a combination enhances the cushioning effect. If the wound bed comprises a skin graft region the reduction of shear forces can be particularly advantageous.

It is to be noted that in use the dressing may be used "up-side down", at an angle or vertical. References to upper and lower are thus used for explanation purposes only.

FIG. 37 illustrates a cross-section, of a portion of an embodiment of a dressing shown in FIGS. 15A-16. In particular, FIG. 37 illustrates a magnified view of the wound contact layer 2102 which includes a lower surface 2101 and multiple perforations 2104 formed as through holes. An upper surface 2104 of the wound contact layer abuts a first layer 2300 of the transmission layer 2105. A further, upper, layer 2301 of the transmission layer 2105 is spaced apart from the first layer. The first and further layers of the transmission layer are kept apart in a spaced apart relationship by multiple mono-filament fiber spacers 2302 which act as resilient flexible pillars separating the two layers of the transmission layer. The upper layer 2301 of the transmission layer is adjacent a lower surface of the absorbent 2110 which, for example, is formed as a pad of fibrous cellulose material interspaced with super-absorbent particulate matter.

FIG. 38 illustrates the lower layer of the 3D fabric transmission layer in more detail. The 3D fabric layer 2105 is formed as a lower and upper knitted layer given a loft by the knitted structure. Rows of the knitted stitches may be referred to as a course of stitches. Columns of stitches may be referred to as a whale. A single monofilament fiber is knitted into the 3D fabric to form the multiple separating strands.

As illustrated in FIG. 38 there are apertures or openings formed between interlocked stitches in the lower layer of the transmission layer 2105. In use, wound exudate including liquid and semi-solid e.g. viscous slurry, suspensions of biological debris or the like and solid material will pass upwards through the perforations 2104 in the wound contact layer and through the openings in the inter knitted structure of the first layer 2300 of the transmission layer. The openings between the interconnected stitches have an average open area ranging from around 2250 microns to 450 microns. The particular open area in the first layer of the transmission layer will be determined by the materials and method of manufacture of the lower layer. FIG. 39 illustrates how an open area of openings in the further layer above the first layer (that is to say further away from the wound) can include openings which have a greater open area than the openings in the lower layer. In this way as wound exudate which includes semi-solid and solid matter moves from the wound bed at the wound site upwards into the wound dressing any particulate matter which is of a size small enough to pass through the relative small openings 2400 in the lower layer will certainly be able to pass through the larger area openings 2501 in the upper area. This helps avoid debris in the form of solid material collecting in the interstitial region between the monofilament fibers between the upper and lower layer. As shown in FIG. 39, the upper layer 2301 may include openings 2500 similar to the openings 2400 in the lower layer 2300. However, during the knitting process the upper surface is knitted so that larger open area openings 2501 are interspersed across the whole surface of the upper layer. As illustrated in FIG. 39 the larger open area openings 2501 can have an open range considerably larger (shown between 2700 to 800 microns). The lower layer 2300 thus acts to some extent as a filtering layer having openings 2400 which enable gas and liquid to pass freely therethrough but to prevent solid and semi-solid particulate matter which is too large from passing in to the interstitial region in the transmission layer 2105. This helps keep a flowpath along the transmission layer open.

By providing openings in an upper layer in the transmission layer which have a greater open area than any openings in the lower area build-up of solid particulate matter in the interstitial region between the upper and lower layers of the transmission layer is avoided since any solid or semi-solid matter will flow along the channel and eventually be enabled to pass upwards through the larger openings where the material is taken up by the super-absorber/absorbent material.

The absorbent layer 2110 holds liquid collected during the application of negative pressure therapy. By having this layer in fluid communication with, and preferably in contact with, the layer of the transmission layer, the region of the transmission layer 2105 is kept at a moist environment. This helps avoid build-up and crusting of the exudate during use.

FIG. 40 illustrates an alternative material which could be utilized as the transmission layer in a wound dressing. In particular, FIG. 40 illustrates a lower surface of a 3D knit material which may be utilized as the transmission layer. Openings 2600 are formed in the surface which enables wound exudate and air to pass from the wound through a wound contact layer which would be located on the surface shown in FIG. 20 and through those openings. FIG. 41 illustrates an upper surface of the material shown in FIG. 40 and illustrates how larger openings 2700 may be formed in the upper surface.

Whilst certain embodiments of the present disclosure have so far been described in which the transmission layer is formed as a 3D knit layer, e.g., two layers spaced apart by a monofilament layer, it will be appreciated that certain embodiments of the present disclosure are not restricted to the use of such a material. In some embodiments, as an alternative to such a 3D knit material one or more layers of a wide variety of materials could be utilized. In each case, according to embodiments of the present disclosure, the openings presented by layers of the transmission layer are wider and wider as one moves away from the side of the dressing which, in use will be located proximate to the wound. In some embodiments, the transmission layer may be provided by multiple layers of open celled foam. In some embodiments, the foam is reticulated open cell foam. Preferably, the foam is hydrophilic or able to wick aqueous based fluids. The pore size in each layer is selected so that in the foam layer most proximate to the wound side in use the pores have a smallest size. If only one further foam layer is utilized that includes pore sizes which are greater than the pore sizes of the first layer. This helps avoid solid particulate being trapped in the lower layer which thus helps maintain the lower layer in an open configuration in which it is thus able to transmit air throughout the dressing. In certain embodiments, two, three, four or more foam layers may be included. The foam layers may be integrally formed, for example, by selecting a foam having a large pore size and then repeatedly dipping this to a lesser and lesser extent into material which will clog the pores or alternatively, the transmission layer formed by the multiple foam layers may be provided by laminating different types of foam in a layered arrangement or by securing such layers of foam in place in a known manner.

According to certain embodiments of the present disclosure, the transmission layer is formed by multiple layers of mesh instead of foam or 3D knit materials. For example, fine gauze mesh may be utilized for a wound facing side of the transmission layer and a Hessian mesh having a larger pore size may be located on a distal side of the gauze mesh facing away from the wound in use. The one, two, three or more layers of mesh can be secured together in an appropriate manner, such as being stitched or adhered together or the like. The resultant mat of fibers provides a transmittal layer through which air can be transmitted in the dressing but by selecting the opening sizes in the meshes as one moves through the dressing away from the wound contact side, the accumulation of solid particulate matter in lower layers can be avoided.

FIG. 42 illustrates an embodiment of a TNP wound treatment comprising a wound dressing 2100 in combination with a pump 2800. As stated above, the wound dressing 2100 can be any wound dressing embodiment disclosed herein including without limitation dressing embodiment 100 or have any combination of features of any number of wound dressing embodiments disclosed herein. Here, the dressing 2100 may be placed over a wound as described previously, and a conduit 2220 may then be connected to the port 2150, although in some embodiments the dressing 2100 may be provided with at least a portion of the conduit 2220 preattached to the port 2150. Preferably, the dressing 2100 is provided as a single article with all wound dressing elements (including the port 2150) pre-attached and integrated into a single unit. The wound dressing 2100 may then be connected, via the conduit 2220, to a source of negative pressure such as the pump 2800. The pump 2800 can be miniaturized and portable, although larger conventional pumps may also be used with the dressing 2100. In some embodiments, the pump 2800 may be attached or mounted onto or adjacent the dressing 2100. A connector 2221 may also be provided so as to permit the conduit 2220 leading to the wound dressing 2100 to be disconnected from the pump, which may be useful for example during dressing changes.

Figure 43A:
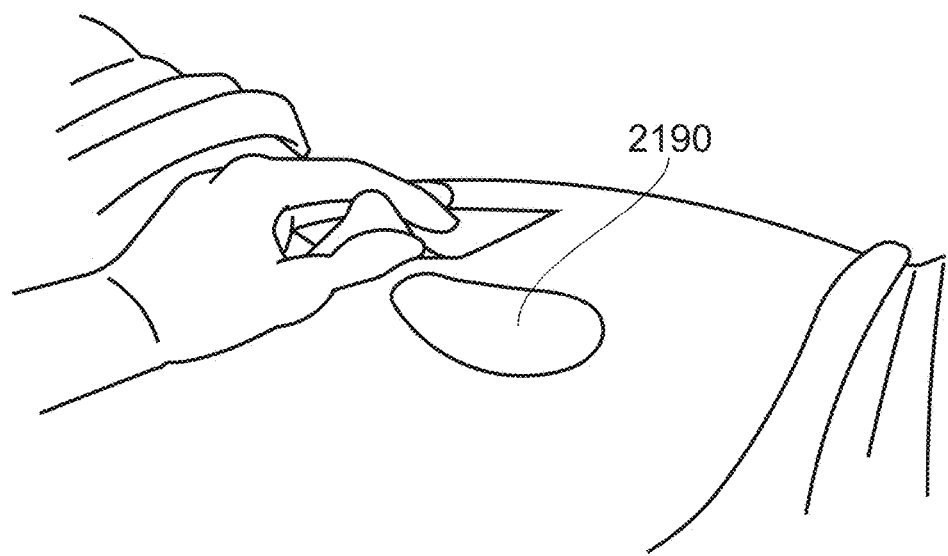

FIGS. 43A-D illustrate the use of an embodiment of a TNP wound treatment system being used to treat a wound site on a patient. FIG. 43A shows a wound site 2190 being cleaned and prepared for treatment. Here, the healthy skin surrounding the wound site 2190 is preferably cleaned and excess hair removed or shaved. The wound site 2190 may also be irrigated with sterile saline solution if necessary. Optionally, a skin protectant may be applied to the skin surrounding the wound site 2190. If necessary, a wound packing material, such as foam or gauze, may be placed in the wound site 2190. This may be preferable if the wound site 2190 is a deeper wound.

Figure 43B:
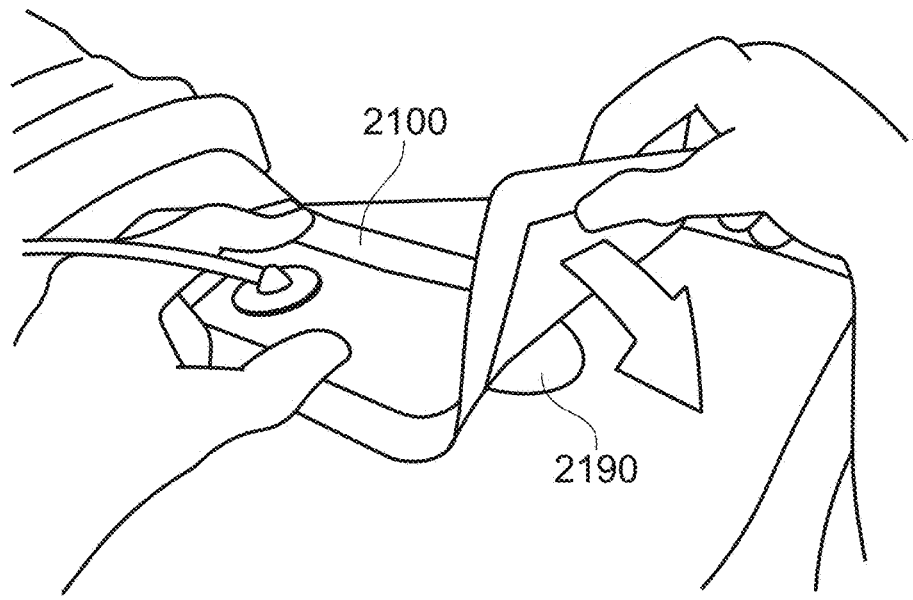

After the skin surrounding the wound site 2190 is dry, and with reference now to FIG. 43B, the wound dressing 2100 may be positioned and placed over the wound site 2190. Preferably, the wound dressing 2100 is placed with the wound contact layer 2102 over and/or in contact with the wound site 2190. In some embodiments, an adhesive layer is provided on the lower surface 2101 of the wound contact layer 2102, which may in some cases be protected by an optional release layer to be removed prior to placement of the wound dressing 2100 over the wound site 2190. Preferably, the dressing 2100 is positioned such that the port 2150 is in a raised position with respect to the remainder of the dressing 2100 so as to avoid fluid pooling around the port. In some embodiments, the dressing 2100 is positioned so that the port 2150 is not directly overlying the wound, and is level with or at a higher point than the wound. To help ensure adequate sealing for TNP, the edges of the dressing 2100 are preferably smoothed over to avoid creases or folds.

Figure 43C:
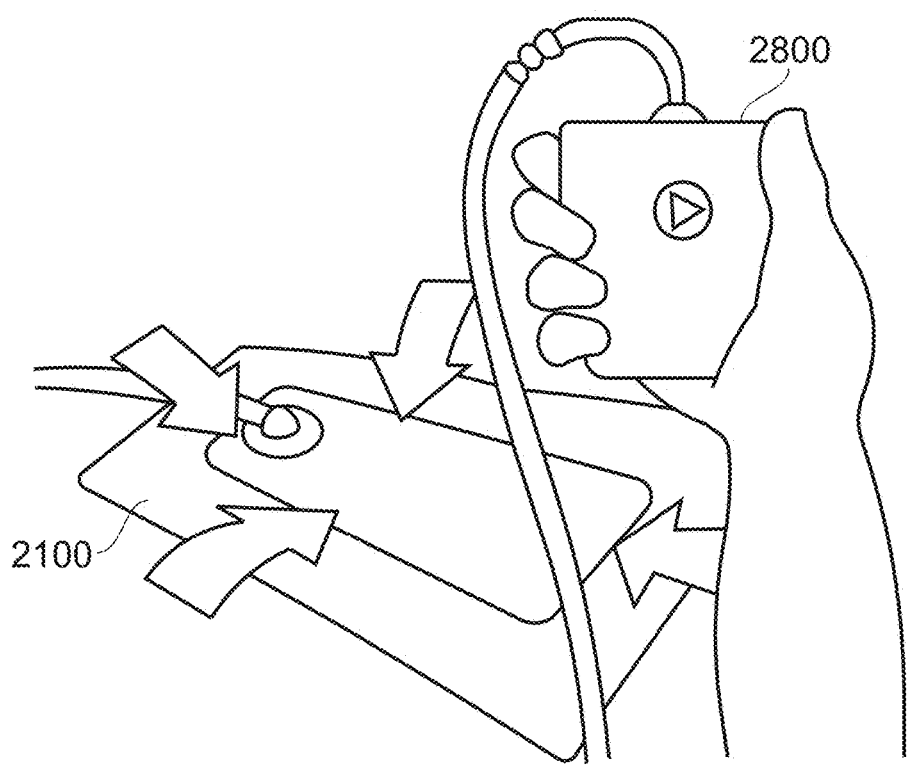

With reference now to FIG. 43C, the dressing 2100 is connected to the pump 2800. The pump 2800 is configured to apply negative pressure to the wound site via the dressing 2100, and typically through a conduit. In some embodiments, and as described above in FIG. 42, a connector may be used to join the conduit from the dressing 2100 to the pump 2800. Upon the application of negative pressure with the pump 2800, the dressing 2100 may in some embodiments partially collapse and present a wrinkled appearance as a result of the evacuation of some or all of the air underneath the dressing 2100. In some embodiments, the pump 2800 may be configured to detect if any leaks are present in the dressing 2100, such as at the interface between the dressing 2100 and the skin surrounding the wound site 2190. Should a leak be found, such leak is preferably remedied prior to continuing treatment.

Figure 43D:
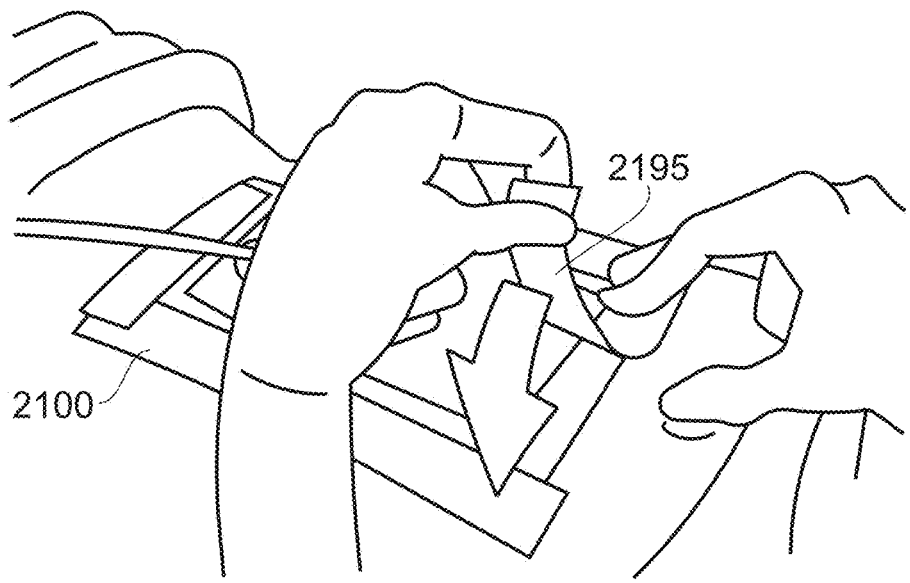

Turning to FIG. 43D, additional fixation strips 2195 may also be attached around the edges of the dressing 2100. Such fixation strips 2195 may be advantageous in some situations so as to provide additional sealing against the skin of the patient surrounding the wound site 2190. For example, the fixation strips 2195 may provide additional sealing for when a patient is more mobile. In some cases, the fixation strips 2195 may be used prior to activation of the pump 2800, particularly if the dressing 2100 is placed over a difficult to reach or contoured area.

Treatment of the wound site 2190 preferably continues until the wound has reached a desired level of healing. In some embodiments, it may be desirable to replace the dressing 2100 after a certain time period has elapsed, or if the dressing is full of wound fluids. During such changes, the pump 2800 may be kept, with just the dressing 2100 being changed.

With the some embodiments of the present disclosure, a wound dressing is provided that helps improve patient concordance with instructions for use, helps improve patients" quality of life, and also helps a clinician observe and monitor a patient's wound.

It will be clear to a person skilled in the art that features described in relation to any of the embodiments described above can be applicable interchangeably between the different embodiments. The embodiments described above are examples to illustrate various features of the present invention or inventions.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the present disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A wound dressing for providing protection at a wound site, comprising:
   a wound contact layer;
   an absorbent layer for absorbing wound exudate, the absorbent layer positioned above the wound contact layer and comprising a border region extending around its radially outer perimeter and a central region within the border region;
   a cover layer positioned above the absorbent layer; and
   an obscuring element positioned between the absorbent layer and the cover layer for at least partially obscuring a view of wound exudate absorbed by the absorbent layer in use, the obscuring element comprising a layer for at least partial masking of wound exudate, wherein the obscuring element layer is provided over the central region of the absorbent layer and not over the border region of the absorbent layer, and wherein the border region of the absorbent layer is directly adjacent to the cover layer such that wound exudate reaching the border region is visible through the cover layer.

2. The wound dressing of claim 1, wherein the obscuring element is translucent.

3. The wound dressing of claim 1, wherein the obscuring element is a masking layer.

4. The wound dressing of claim 1, wherein the absorbent layer comprises a plurality of non-woven randomly oriented fibers, and wherein the plurality of non-woven randomly oriented fibers spread wound exudate absorbed in a central region of the absorbent layer outward to the border region of the absorbent layer.

5. The wound dressing of claim 1, wherein the obscuring element comprises an indicator for indicating the need to change the dressing.

6. The wound dressing of claim 1, further comprising a plurality of openings in the obscuring element for allowing fluid to move therethrough.

7. The wound dressing of claim 1, wherein the obscuring element comprises, or is coated with, a material having size-exclusion properties for selectively permitting or preventing passage of molecules of a predetermined size or weight, the molecules comprising proteins.

8. The wound dressing of claim 1, wherein the obscuring element comprises, or is coated with, a hydrophilic material.

9. The wound dressing of claim 1, wherein the obscuring element comprises a three-dimensional knitted spacer fabric.

10. The wound dressing of claim 1, wherein the cover layer is a translucent film having a moisture vapour permeability of 500 g/m²/24 hours or more.

11. The wound dressing of claim 10, wherein the translucent film is a bacterial barrier.

12. The wound dressing of claim 1, wherein the wound contact layer carries an adhesive portion on a lower surface thereof, the adhesive portion for forming a substantially fluid tight seal over the wound site.

13. The wound dressing of claim 1, wherein the obscuring element is configured to at least partially mask light radiation having wavelength of 600 nm and less.

14. The wound dressing of claim 1, wherein the obscuring element is configured to reduce light absorption by 50% or more.

15. The wound dressing of claim 1, wherein the obscuring element is configured to yield a CIE L* value of 50 or more, and optionally 70 or more.

16. The wound dressing of claim 1, wherein the obscuring element and the absorbent layer are provided as a single layer.

17. The wound dressing of claim 1, wherein the dressing is shaped to include a number of lobes.

18. The wound dressing of claim 17, wherein the absorbent layer comprises a first shape including the number of lobes, wherein the border region extends around radially outer edges of the lobes of the absorbent layer, wherein the obscuring element comprises a second shape including the number of lobes.

19. The wound dressing of claim 18, wherein the second shape is smaller than the first shape such that the obscuring element is not provided over the radially outer edges of the lobes of the absorbent layer.

20. The wound dressing of claim 19, wherein the positioning of the obscuring element enables visibility of wound exudate reaching the radially outer edges of the lobes of the absorbent layer.

21. The wound dressing of claim 1, further comprising a porous layer positioned between the wound contact layer and the absorbent layer, the porous layer configured to draw exudate away from the wound site.

22. The wound dressing of claim 1, further comprising an odour control element dispersed within or adjacent the absorbent layer.

23. The wound dressing of claim 1, wherein the dressing further comprises an odour control element and a foam layer, wherein the odour control element is provided as a layer sandwiched between the foam layer and the absorbent layer.

* * * * *

UNITED STATES PATENT AND TRADEMARK OFFICE
CERTIFICATE OF CORRECTION

PATENT NO. : 10,130,519 B2
APPLICATION NO. : 15/219886
DATED : November 20, 2018
INVENTOR(S) : Ella Lynn Mumby It is certified that error appears in the above-identified patent and that said Letters Patent is hereby corrected as shown below:

In the Specification

In Column 1, Line 57, change "Carbon®," to --carbon®,--.

In Column 12, Line 21, change "their as" to --their--.

In Column 13, Line 63, change "chosen" to --chosen.--.

In Column 14, Line 5, change "prevention" to --prevention.--.

In Column 17, Line 27, change "AlleyvnTM" to --AllevynTM--.

In Column 24, Line 56, change "judged," to --judged--.

In Column 30, Line 26, change "pen-wound" to --peri-wound--.

In Column 38, Line 35, change "Versapore™" to --Versapor™--.

In Column 40, Line 19, change "2D sealed" to --sealed--.

In Column 42, Line 25, change "wilt" to --will--.

In Column 43, Line 15 (Approx.), change "(east" to --least--.

In Column 44, Line 50, change "bathe" to --baffle--.

In Column 47, Line 25, change "cyclodextrine," to --cyclodextrin,--.

In Column 48, Line 54, change "cross-section," to --cross-section--.

Signed and Sealed this
Second Day of April, 2019

Andrei Iancu
*Director of the United States Patent and Trademark Office*